US012734078B2

(12) United States Patent
Erickson et al.

(10) Patent No.: US 12,734,078 B2
(45) Date of Patent: Sep. 15, 2026

(54) MOISTURE MANAGEMENT LOWER TORSO GARMENTS AND METHODS

(71) Applicant: HBI Branded Apparel Enterprises, LLC, Winston-Salem, NC (US)

(72) Inventors: Rachel Erickson, Winston-Salem, NC (US); Tasha Perry, Winston-Salem, NC (US); Sherry E. Kimel, Winston-Salem, NC (US); Kimberly Yontz, Winston-Salem, NC (US)

(73) Assignee: HBI Branded Apparel Enterprises, LLC, Winston-Salem, NC (US)

( * ) Notice: Subject to any disclaimer, the term of this patent is extended or adjusted under 35 U.S.C. 154(b) by 0 days.

(21) Appl. No.: 19/182,775

(22) Filed: Apr. 18, 2025

(65) Prior Publication Data

US 2025/0325414 A1 Oct. 23, 2025

Related U.S. Application Data

(60) Provisional application No. 63/636,055, filed on Apr. 18, 2024.

(51) Int. Cl.

| | |
|---|---|
| ***A61F 13/496*** | (2006.01) |
| *A41B 9/00* | (2006.01) |
| *A61F 13/15* | (2006.01) |

(52) U.S. Cl.

CPC .................... *A61F 13/4963* (2013.01); *A61F 2013/15121* (2013.01)

(58) Field of Classification Search

CPC ................... A61F 13/4963; A61F 2013/15121

See application file for complete search history.

(56) References Cited

U.S. PATENT DOCUMENTS

| | | | | |
|---|---|---|---|---|
| 2,033,456 | A | 3/1936 | Cunningham | |
| 2,255,931 | A * | 9/1941 | Kloster | A41B 9/02 2/404 |
| 2,438,310 | A | 3/1948 | Ashe et al. | |
| 2,664,889 | A * | 1/1954 | Bailey | A41B 9/02 2/403 |
| 2,838,761 | A | 6/1958 | Title | |

(Continued)

FOREIGN PATENT DOCUMENTS

| | | | |
|---|---|---|---|
| AU | 2010229644 | B2 | 7/2013 |
| AU | 2013288292 | B2 | 11/2016 |

(Continued)

OTHER PUBLICATIONS

Combined Search and Examination Report under Sections 17 and 18(3) for corresponding Great Britain Application No. 2505951.0, mailed Oct. 23, 2025, 9 pages.

*Primary Examiner* — Robert H Muromoto, Jr.

(74) *Attorney, Agent, or Firm* — Husch Blackwell LLP

(57) ABSTRACT

A garment is provided. The garment includes a body provided in the form of a front lower torso portion and a rear lower torso portion, a waist opening, left and right leg openings, and a pouch disposed at least in part in the front lower torso portion. The pouch includes a first pouch panel and a second pouch panel. Each of the first and second pouch panels includes a first fabric layer coupled to a second fabric layer. The first fabric layer of the first pouch panel and the second pouch panel are designed to transport liquid away from a lower torso region of a wearer.

20 Claims, 17 Drawing Sheets

(56) References Cited

U.S. PATENT DOCUMENTS 3,517,666 A * 6/1970 Atlee .................... A41B 9/02 2/403
3,595,034 A 7/1971 Safrit
4,326,302 A * 4/1982 Lowe .................... A61F 5/4401 2/405
4,338,938 A * 7/1982 Seavitt .............. A61F 13/49004 604/385.15
4,344,999 A 8/1982 Gohlke
4,397,646 A * 8/1983 Daniels .............. A61F 13/49004 604/385.15
4,516,975 A * 5/1985 Mitchell ................ A61F 13/62 604/385.15
4,555,245 A * 11/1985 Armbruster ............. A61F 13/72 2/403
4,690,681 A * 9/1987 Haunschild ........... A61F 13/496 604/396
4,698,849 A 10/1987 Mitchell et al.
4,880,424 A * 11/1989 Rautenberg ............. A61F 13/66 2/919
4,961,736 A * 10/1990 McCloud .......... A61F 13/49004 604/397
4,961,985 A 10/1990 Henn et al.
5,029,345 A * 7/1991 Angheluta ............. A41B 9/023 2/403
5,081,716 A 1/1992 Lehenbauer et al.
5,087,253 A * 2/1992 Cooper ................ A61F 5/4401 604/385.15
5,098,419 A * 3/1992 Gold ...................... A61F 13/49 2/401
5,122,407 A * 6/1992 Yeo ...................... A61F 13/512 442/76
5,210,882 A 5/1993 Moretz et al.
5,291,617 A 3/1994 Moretz et al.
5,454,799 A * 10/1995 Lakiss-Smith .... A61F 13/49004 604/358
5,591,151 A * 1/1997 Hasse .................. A61F 13/496 604/394
5,948,707 A 9/1999 Crawley et al.
6,401,250 B1 6/2002 McNabb
6,427,620 B1 8/2002 Crawford
6,959,564 B2 11/2005 Miller, III
7,024,892 B2 4/2006 Blakely
7,310,824 B2 12/2007 Walsh
7,322,966 B1 1/2008 Deerin
7,356,851 B2 4/2008 Spruill
7,437,774 B2 10/2008 Baron et al.
7,533,423 B2 5/2009 Rudolph
7,546,751 B2 6/2009 Lutz
7,669,248 B2 3/2010 Toratani
7,686,792 B2 3/2010 Bell et al.
7,752,681 B2 7/2010 Michel
7,827,623 B2 11/2010 Kurata
7,958,571 B2 * 6/2011 Kitsch .................... A41B 9/023 2/403
7,959,618 B2 * 6/2011 Hermansson ......... A61F 13/496 604/385.24
8,039,685 B2 10/2011 Mason, Jr. et al.
8,083,880 B2 12/2011 Kurata
8,123,735 B2 2/2012 Deerin
8,127,575 B2 * 3/2012 Burrow .................. A41D 31/12 66/202
8,146,176 B2 4/2012 Rudolph
8,211,078 B2 7/2012 Noel
8,360,816 B2 1/2013 Michel
8,388,590 B2 3/2013 Mason, Jr. et al.
8,460,265 B1 * 6/2013 Calender ........... A61F 13/49006 604/385.15
8,528,114 B2 9/2013 Baiany
8,546,641 B2 10/2013 Roe
8,597,222 B2 12/2013 Lucero et al.
8,702,668 B2 4/2014 Noel
8,726,414 B2 5/2014 Baron et al.
8,732,865 B2 5/2014 Ishikawa et al.
8,759,605 B2 6/2014 Roe
8,808,263 B2 8/2014 Roe et al.
8,898,812 B2 12/2014 Thompson et al.
8,932,273 B2 1/2015 Roe et al.
8,935,813 B2 1/2015 O'Leary
8,938,816 B2 1/2015 Söderström
8,968,266 B2 3/2015 Kumar
9,011,398 B2 4/2015 Johnston et al.
9,011,402 B2 4/2015 Roe et al.
9,011,403 B2 4/2015 De Bruin et al.
9,107,459 B2 8/2015 Mayer et al.
9,192,524 B2 11/2015 Orchard, IV et al.
9,192,526 B2 11/2015 De Bruin et al.
9,198,805 B2 12/2015 Gray et al.
9,198,806 B2 12/2015 Vignali et al.
9,198,807 B2 12/2015 Evenson et al.
9,226,862 B2 1/2016 Orchard, IV et al.
9,241,516 B2 1/2016 Sokolowski et al.
9,289,330 B2 3/2016 Mason, Jr. et al.
9,301,551 B2 4/2016 Bäck et al.
9,308,131 B2 4/2016 Evenson et al.
9,320,307 B2 4/2016 Berns et al.
9,345,272 B2 5/2016 Hurd
9,380,821 B2 7/2016 Martin
9,486,017 B2 11/2016 Liu
9,557,143 B2 1/2017 Howland
9,560,890 B2 2/2017 Friedrich
9,566,196 B2 2/2017 Carlucci et al.
9,566,197 B2 2/2017 Carlucci et al.
9,579,238 B2 2/2017 Noel
9,624,608 B2 4/2017 Martin et al.
9,655,388 B2 5/2017 Michel
9,675,499 B2 6/2017 Evenson et al.
9,687,031 B2 6/2017 Turner
9,700,077 B2 7/2017 Baron et al.
9,713,351 B2 7/2017 Wexler
9,713,352 B2 7/2017 Demarest
9,801,421 B2 10/2017 Turner
9,833,022 B2 12/2017 Mayer et al.
9,931,250 B2 4/2018 Carlucci et al.
9,968,139 B2 5/2018 Callahan
9,980,861 B2 5/2018 Deerin
9,993,034 B2 6/2018 Callahan
10,021,921 B2 7/2018 James
10,104,918 B2 10/2018 Hurd
10,123,580 B2 11/2018 Carter et al.
10,123,920 B2 11/2018 Lankhof et al.
10,154,702 B1 12/2018 Neary et al.
10,165,813 B2 1/2019 Martin
10,231,885 B2 3/2019 Hovey
10,244,798 B2 4/2019 Wexler
10,273,606 B2 4/2019 Turner
10,327,489 B2 6/2019 Pezzimenti
10,398,610 B2 9/2019 Robles et al.
10,401,125 B2 9/2019 Howland
10,426,206 B2 10/2019 Davis et al.
10,441,479 B2 10/2019 Griffiths
10,448,679 B1 10/2019 Roddis et al.
10,455,868 B2 10/2019 Duffy et al.
10,463,085 B2 11/2019 McGargill
10,463,097 B2 11/2019 Baron et al.
10,517,335 B2 12/2019 Berns et al.
10,531,696 B2 1/2020 Achtymichuk
10,555,841 B2 2/2020 Png et al.
10,568,781 B2 2/2020 Noel
10,595,568 B2 3/2020 Parkinson
10,617,160 B2 4/2020 Spruill et al.
10,660,373 B2 5/2020 Martin
10,674,777 B2 6/2020 Fisher
10,750,793 B1 8/2020 Theodoridis
10,767,297 B2 9/2020 Lin et al.
10,786,024 B2 9/2020 Pezzimenti
10,786,052 B2 9/2020 Brandt et al.
10,834,983 B2 11/2020 Cherry et al.
10,888,470 B2 1/2021 Riha-Scott et al.
10,897,941 B1 1/2021 Smoter
10,905,178 B2 2/2021 Sokolowski et al.
10,959,465 B2 3/2021 Melendez et al.
RE48,511 E 4/2021 Thompson et al.

(56) References Cited

U.S. PATENT DOCUMENTS 10,966,468 B2* 4/2021 Waitz .................... A41B 9/004
10,980,289 B2 4/2021 Ng
10,980,299 B1 4/2021 Neary et al.
10,986,877 B2 4/2021 Kimel et al.
10,993,848 B2 5/2021 Hardie et al.
10,993,852 B2 5/2021 Boll et al.
11,058,155 B2 7/2021 Roddis et al.
11,076,651 B2 8/2021 Baron et al.
11,096,430 B2 8/2021 Otashevich et al.
11,129,755 B2 9/2021 Hardie et al.
11,134,733 B2 10/2021 Miller et al.
11,136,697 B2 10/2021 Minor et al.
11,147,327 B2 10/2021 Andre
11,207,225 B2 12/2021 Kajanthan et al.
11,229,241 B2 1/2022 Adams
11,234,466 B2 2/2022 Mayer et al.
11,234,468 B2 2/2022 Melendez et al.
11,272,744 B2 3/2022 Shaughnessy et al.
11,291,258 B2 4/2022 Fisher
11,324,265 B2 5/2022 Holmes
11,330,847 B2 5/2022 Etienne
11,350,681 B1 6/2022 Muhlenfeld et al.
11,357,269 B2 6/2022 Ewell
11,388,943 B2 7/2022 Berns et al.
11,419,369 B1 8/2022 Duke
11,523,641 B2 12/2022 Williams
11,540,572 B2 1/2023 Horbatuck
11,648,159 B2 5/2023 Zink et al.
11,752,049 B2 9/2023 Kajanthan et al.
11,766,077 B2 9/2023 Fernando et al.
11,896,063 B2 2/2024 Hanson Allen et al.
12,343,240 B2* 7/2025 Sepello ............. A61F 13/49003
2004/0082927 A1* 4/2004 Littleton .................. A41B 9/02 604/359
2006/0070163 A1 4/2006 Beck et al.
2007/0294803 A1 12/2007 Furgerson et al.
2008/0052802 A1 3/2008 Bryan
2008/0060113 A1 3/2008 Walsh
2009/0025115 A1 1/2009 Duffy et al.
2011/0250409 A1 10/2011 Marte et al.
2013/0312154 A1 11/2013 Koga et al.
2014/0039432 A1* 2/2014 Dunbar ............. A61F 13/15577 604/394
2014/0041097 A1 2/2014 Toratani
2015/0290049 A1* 10/2015 Riha-Scott ............. A41B 9/001 604/387
2017/0202287 A1 7/2017 Walter et al.
2018/0020746 A1 1/2018 Wyner et al.
2018/0064188 A1 3/2018 Hardy et al.
2018/0132545 A1 5/2018 Fromer et al.
2018/0146717 A1 5/2018 Ballone et al.
2018/0249775 A1 9/2018 Pitchforth et al.
2018/0310632 A1 11/2018 Hanson Allen et al.
2018/0318142 A1 11/2018 Gagliardo
2018/0343932 A1 12/2018 Gosse et al.
2018/0352883 A1 12/2018 Schlee et al.
2019/0000155 A1 1/2019 Saunders et al.
2019/0125003 A1 5/2019 Hanson Allen et al.
2019/0133216 A1 5/2019 Durham
2019/0150539 A1 5/2019 Hiney
2019/0191791 A1 6/2019 Patterson
2019/0209395 A1 7/2019 Hovey
2019/0320738 A1 10/2019 Kiuchi et al.
2020/0000155 A1* 1/2020 Etienne ................. A61F 13/505
2020/0022436 A1 1/2020 Baron et al.
2020/0113747 A1 4/2020 Larson et al.
2020/0170309 A1 6/2020 Ewell
2020/0170851 A1 6/2020 Png et al.
2020/0214376 A1 7/2020 Cherry et al.
2020/0222256 A1 7/2020 Chong
2020/0237021 A1 7/2020 Adams
2020/0246203 A1 8/2020 Tulk et al.
2020/0323278 A1 10/2020 Roddis et al.
2020/0337912 A1 10/2020 Kwan
2020/0397063 A1* 12/2020 Biodrowski ........... A41B 9/004
2021/0017703 A1 1/2021 Farmer et al.
2021/0030605 A1 2/2021 Kajanthan et al.
2021/0100698 A1 4/2021 Langdon et al.
2021/0106069 A1 4/2021 Aiello
2021/0161735 A1 6/2021 Lankhof et al.
2021/0195964 A1 7/2021 Melendez et al.
2021/0212395 A1 7/2021 Neary et al.
2021/0219628 A1 7/2021 Rendone
2021/0235773 A1 8/2021 Kimel et al.
2021/0235792 A1 8/2021 Rea
2021/0236345 A1* 8/2021 Glaug ............... A61F 13/49012
2021/0251303 A1 8/2021 Collins et al.
2021/0251818 A1 8/2021 Roe et al.
2021/0274869 A1 9/2021 McNally et al.
2021/0282469 A1 9/2021 Siriwardena
2021/0290447 A1 9/2021 Sepello et al.
2021/0298369 A1 9/2021 Polstein et al.
2021/0361498 A1 11/2021 Schoenborn et al.
2021/0368892 A1 12/2021 Meng et al.
2021/0401068 A1 12/2021 Callahan
2022/0030960 A1 2/2022 Almog
2022/0039483 A1 2/2022 Agou
2022/0053841 A1 2/2022 Roddis et al.
2022/0079275 A1 3/2022 Miller et al.
2022/0160552 A1 5/2022 Carpenter
2022/0167686 A1 6/2022 Shaughnessy et al.
2022/0248777 A1 8/2022 Gilbert
2022/0257430 A1 8/2022 Miller et al.
2022/0287380 A1 9/2022 Nicholson
2022/0295909 A1 9/2022 Melendez et al.
2022/0304866 A1 9/2022 Strasemeier et al.
2022/0304867 A1 9/2022 Giovanni et al.
2022/0304869 A1 9/2022 Arizti et al.
2022/0312875 A1 10/2022 Berns et al.
2022/0330622 A1 10/2022 Hanson Allen et al.
2022/0338564 A1 10/2022 Muhlenfeld et al.
2022/0354710 A1* 11/2022 Sepello ............. A61F 13/15268
2022/0378116 A1 12/2022 Morris, V et al.
2022/0408848 A1 12/2022 Krupa
2023/0059401 A1 2/2023 Mellos
2023/0082418 A1 3/2023 Mellos
2023/0094829 A1 3/2023 Kim et al.
2023/0180870 A1 6/2023 Yao
2023/0218016 A1 7/2023 Mackenzie
2023/0225437 A1 7/2023 Carlino et al.
2023/0338206 A1 10/2023 Welch et al.
2023/0372166 A1 11/2023 Robles et al.
2023/0390127 A1 12/2023 Kajanthan et al.
2023/0397674 A1 12/2023 Fernando et al.
2024/0000622 A1 1/2024 Stanley et al.
2024/0122271 A1* 4/2024 Perry ................... A41B 17/005
2024/0358558 A1* 10/2024 Orr ................... A61F 13/49003
2025/0325059 A1* 10/2025 Erickson .............. A41D 31/305

FOREIGN PATENT DOCUMENTS

AU 2019204873 A8 8/2019
AU 2018317934 A1 2/2020
CA 2827795 C 12/2014
CA 2961668 C 7/2018
CA 2945296 C 2/2019
CA 3073436 A1 2/2019
CA 3073971 A1 3/2019
CA 2942869 C 10/2019
CA 3115963 A1 4/2020
EP 1600067 B1 12/2012
EP 2043580 B1 9/2014
EP 2879534 B1 3/2017
EP 3128970 A4 11/2017
EP 2872095 B1 11/2018
EP 3439495 A1 2/2019
EP 3677425 A4 3/2021
EP 3668466 A4 4/2021
EP 3674074 A4 5/2021
EP 3849539 A1 7/2021
EP 3860379 A1 8/2021
NZ 626874 A 8/2014
WO 1999016616 A1 4/1999
WO 2001034080 A2 5/2001

(56) References Cited

FOREIGN PATENT DOCUMENTS

WO 2001066851 A1 9/2001
WO 2003013291 A2 2/2003
WO 2004098327 A1 11/2004
WO 2005039336 A1 5/2005
WO 2006032096 A1 3/2006
WO 2006073719 A2 7/2006
WO 2006113371 A2 10/2006
WO 2007086110 A1 8/2007
WO 2008002431 A2 1/2008
WO 2008093435 A1 8/2008
WO 2009048504 A2 4/2009
WO 2009084079 A1 7/2009
WO 2010082677 A1 7/2010
WO 2012090265 A1 7/2012
WO 2012154251 A1 11/2012
WO 2013123504 A1 8/2013
WO 2013159017 A1 10/2013
WO 2014135988 A2 9/2014
WO 2015082902 A1 6/2015
WO 2017091414 A1 6/2017
WO 2018022625 A1 2/2018
WO 2019070197 A1 4/2019
WO 2020056313 A1 3/2020
WO 2020085091 A1 4/2020
WO 2020086330 A1 4/2020
WO 2020178836 A1 9/2020
WO 2020212988 A1 10/2020
WO 2020214540 A1 10/2020
WO 2020243734 A1 12/2020
WO 2021054922 A1 3/2021
WO 2021092237 A1 5/2021
WO 2021112695 A1 6/2021
WO 2021150656 A1 7/2021
WO 2021168513 A1 9/2021
WO 2021168546 A1 9/2021
WO 2021177992 A1 9/2021
WO 2021183598 A1 9/2021
WO 2021211086 A1 10/2021
WO 2022060629 A1 3/2022
WO 2022067392 A1 4/2022
WO 2022115851 A1 6/2022
WO 2022186249 A1 9/2022
WO 2022197245 A1 9/2022
WO 2022203987 A1 9/2022
WO 2022203988 A1 9/2022
WO 2022203989 A1 9/2022
WO 2022226551 A1 10/2022
WO 2022235734 A1 11/2022
WO 2022246494 A1 12/2022
WO 2022246495 A1 12/2022
WO 2023009416 A1 2/2023
WO 2023023777 A1 3/2023
WO 2023091094 A1 5/2023
WO 2023168238 A1 9/2023
WO 2024006643 A1 1/2024

* cited by examiner

MOISTURE MANAGEMENT LOWER TORSO GARMENTS AND METHODS

CROSS-REFERENCE TO RELATED APPLICATIONS

This application claims priority under 35 U.S.C. § 119 to U.S. Provisional Application No. 63/636,055, filed Apr. 18, 2024, the entirety of which is hereby incorporated by reference.

FIELD OF DISCLOSURE

The present disclosure relates generally to an undergarment and, more particularly, to a lower torso undergarment providing moisture management to a wearer.

BACKGROUND

Fluid excretions such as perspiration and urination are natural physiological occurrences that serve important functions, including thermoregulation, waste elimination, and others. However, for many individuals, managing undesired or excessive moisture in the lower torso region can be a persistent concern. For example, perspiration can be concentrated around the lower torso region. Further, the lower torso is also subject to other sources of moisture, such as drips of urine, which can occur after urination. The accumulation of moisture—whether from perspiration, residual urine, or other sources—can lead to discomfort, skin irritation, hygiene concerns, perceptible odors, and other undesirable outcomes, all of which may cause embarrassment or inconvenience.

When purchasing undergarments, consumers may consider a variety of criteria such as fit, appearance, price, and performance. Increasingly, however, many consumers are prioritizing a garment's ability to effectively manage moisture. To address this issue, manufacturers have explored a variety of fabrics, materials, chemical treatments, etc. designed to manage moisture. However, the challenge of designing a lower torso garment that effectively manages moisture (e.g., perspiration, urine, etc.) while maintaining the desired level of in-wear comfort remains, particularly in male undergarments. Current solutions suffer from poor fit (e.g., being either too loose or overly restrictive), or rely on excessive fabric thickness to absorb moisture, which can lead to moisture becoming trapped within the garment, exacerbating the wearer's discomfort. Whether dealing with perspiration, drips of urine, or other sources of moisture, there is a long-standing need for a garment, particularly a lower torso garment or an undergarment, that provides effective moisture management without compromising comfort or fit and without adding unnecessary bulk.

SUMMARY

The garments of the present disclosure are designed to provide improved moisture management and overcome many of the shortcomings and limitations of existing products. The garments of the present disclosure provide improved moisture management by incorporating moisture-absorbent or moisture-adsorbent zones (e.g., a moisture-absorbent pouch) that contact areas of the body that generate or are susceptible to greater amounts of moisture (e.g., perspiration, urine, etc.).

In one aspect, a garment is provided. The garment includes a body having a front lower torso portion and a rear lower torso portion, a waist opening, left and right leg openings, and a pouch disposed at least in part in the front lower torso portion. The pouch includes a first pouch panel and a second pouch panel. Each of the first and second pouch panels includes a first fabric layer coupled to a second fabric layer. The first fabric layer of each of the first pouch panel and the second pouch panel is designed to transport liquid away from a lower torso region of a wearer.

In some instances, the liquid comprises urine.

In certain instances, the pouch extends to and is coupled to the rear lower torso portion.

In some instances, the garment further includes a gusset positioned between the pouch and the rear torso portion. The gusset is coupled to the pouch and the rear lower torso portion.

In certain instances, the garment further includes a rear panel positioned at least partially on the rear lower torso portion. The rear panel is imparted with moisture management properties.

In some instances, each of the first pouch panel and the second pouch panel consists of the first fabric layer and the second fabric layer.

In certain instances, a chemical treatment imparts the second pouch layer with moisture-resistant properties.

In some instances, a technical back of the first fabric layer of the first pouch panel is positioned adjacent to the technical back of the second fabric layer of the first pouch panel, and wherein a technical face of the first fabric layer of the first pouch panel includes a plurality of pores designed to transport moisture. In some such instances, the moisture may be transported through the first fabric layer via capillary action.

In certain instances, the body includes a first fabric, the second fabric layer of the first pouch panel and the second pouch panel includes a second fabric, and the first and second fabrics include the same fabric blend. In some such instances, the first fabric layer of the first pouch panel and the first fabric layer of the second pouch panel includes a third fabric, and the third fabric includes a synthetic fabric blend imparted with a fabric weight of about 240 grams per square meter to about 295 grams per square meter. In other such instances, the first fabric layer of the first pouch panel and the first fabric layer of the second pouch panel includes a third fabric, and the third fabric includes a synthetic fabric blend imparted with a fabric weight of about 135 grams per square meter to about 185 grams per square meter.

In another aspect, a lower torso garment is provided. The lower torso garment includes a body provided in the form of front and rear lower torso portions coupled together to define a waist opening and a pouch disposed at least partially in the front lower torso portion. The pouch includes a fly panel assembly arranged to be adjacent to a body of a wearer when the garment is worn in its intended configuration, a cover panel assembly positioned adjacent to the fly panel assembly, and a fly opening at least partially defined by the fly panel assembly and the cover panel assembly. The pouch is imparted with moisture management properties.

In some instances, a portion of the fly panel assembly is decoupled from the garment, and a portion of the cover panel assembly is decoupled from the garment.

In certain instances, the pouch is coupled to the body via a first pouch seam, a second pouch seam, and a third pouch seam. The first pouch seam and the second pouch seam couple two or more fabric layers of the pouch together, the first pouch seam and the second pouch seam couple the fly panel assembly and the cover panel assembly to the front lower torso portion, and the third pouch seam couples the pouch to a gusset or the rear lower torso portion.

In some instances, the fly panel assembly includes at least one fabric layer comprising a moisture-absorbent mesh and at least one fabric layer comprising a blend of hydrophobic and hydrophilic materials.

In certain instances, at least one of the fly panel assembly and the cover panel assembly is treated with one or more agents selected from a group consisting of a wicking agent, a soil release agent, an odor control agent, a water-repelling agent, a water-resistant agent, an antibacterial agent, an antimicrobial agent, a hygiene agent, and combinations thereof.

In some instances, the fly panel assembly and the cover panel assembly each includes a technical face and a technical back. The technical face of the fly panel assembly is imparted with a first texture to facilitate moisture transport, and the technical back of the fly panel assembly is imparted with a second texture different from the first texture.

In certain instances, the fly panel assembly and the cover panel assembly each includes a first fabric layer configured to transport moisture away from the wearer's body, a second fabric layer at least partially visible when the exterior of the garment is viewed, and a third fabric layer positioned between the first and second fabric layers. The third fabric layer is provided in substantially the same form as the first fabric layer.

In some instances, the fly panel assembly includes a first fabric layer configured to transport moisture away from the body of the wearer, a second fabric layer positioned proximate to an exterior of the garment, and a third fabric layer positioned between the first and second fabric layers, the third fabric layer provided in substantially the same form as the first fabric layer.

In some instances, a first seam couples the fly panel assembly to the front lower torso portion, a second seam disposed opposite of the first seam couples a first fabric layer and a second fabric layer of the fly panel assembly together, and the second seam is proximate to the fly opening. In addition, a third seam couples the cover panel assembly to the front lower torso portion. In some such instances, the second seam is provided in the form of a fold-over seam, and the fold-over seam is coupled to the third seam.

In a further aspect, a boxer-brief is provided. The boxer-brief includes a body provided in the form of front and rear lower torso portions defining an interior of the body, a waist opening, left and right leg portions coupled to the front and rear lower torso portions, and a pouch positioned at least partially within the front lower torso portion and coupled to the body. The pouch is configured to impart moisture management properties to the garment. The pouch is defined by a first panel arranged adjacent to the interior of the body and a second panel positioned adjacent to the first panel. The first panel includes a first fabric layer designed to transport moisture and a second fabric layer that is imparted with moisture-resistant properties. The first fabric layer of the first panel is positioned adjacent to a wearer's body when the garment is worn in an intended configuration. The second panel includes a third fabric layer designed to transport moisture and a fourth fabric layer that is imparted with moisture-resistant properties. The fourth fabric layer is provided on an exterior surface of the garment when the garment is worn in the intended configuration.

In one aspect, a moisture management garment is provided. The garment comprises a body including a front lower torso portion and a rear lower torso portion, a waist opening, left and right leg portions, and a pouch disposed at least in part in the front lower torso portion and coupled to the left and right leg portions and to the front lower torso portion. The pouch comprises a first, wearer-facing fabric layer and a second fabric layer disposed beneath the first, wearer-facing fabric layer. The first, wearer-facing fabric layer adsorbs moisture, and the second fabric layer repels moisture.

In another aspect, another moisture management garment is provided. The garment comprises a body provided in the form of front and rear lower torso portions, a waist opening, left and right leg portions coupled to the front and rear lower torso portions, and a pouch disposed at least partially in the front lower torso portion and coupled to the left and right leg portions and to the front lower torso portion. The pouch includes a first, wearer-facing fabric layer having a first wearer-facing surface, a first outward-facing surface, and a first perimeter edge and a second fabric layer disposed beneath the first, wearer-facing fabric layer, the second fabric layer having a second wearer-facing surface, a second outward-facing surface, and a second perimeter edge. At least the second fabric layer is treated with a water-resistant agent, laminated, or a combination thereof. The first perimeter edge is coupled to the second perimeter edge.

In an additional aspect, a boxer-brief is provided. The boxer-brief includes a body provided in the form of front and rear lower torso portions defining an interior of the body, a waist opening, left and right leg portions coupled to the front and rear lower torso portions, and a pouch positioned at least partially within the front lower torso portion and coupled to the body. The pouch is configured to impart moisture management properties to the garment. The pouch is defined by a first panel including a first fabric layer designed to transport moisture and a second fabric layer that is imparted with moisture-resistant properties, the first fabric layer of the first panel positioned adjacent to a wearer's body when the boxer-brief is worn in an intended configuration.

In yet another aspect, a method of manufacturing a lower torso moisture management garment is provided. The method comprises the steps of providing a body, a pair of leg portions, and a pouch and coupling the body, the pair of leg portions, and the pouch. The pouch comprises a first panel assembly and a second panel assembly, each of the first and second panel assemblies including a first, wearer-facing fabric layer and a coextensive second fabric layer disposed beneath the first, wearer-facing fabric layer. The first, wearer-facing fabric layer adsorbs moisture, and the second fabric layer repels moisture. The step of coupling the body, the pair of leg portions, and the pouch comprises coupling the first, wearer-facing fabric layer, the coextensive second fabric layer, the first and second panel assemblies, the body, and the pair of leg portions along the perimeter edges of the first, wearer-facing fabric layer and the coextensive second fabric layer.

These and other aspects and advantages of the present disclosure will become apparent to those skilled in the art after considering the following detailed description in connection with the accompanying drawings.

Figure 1:
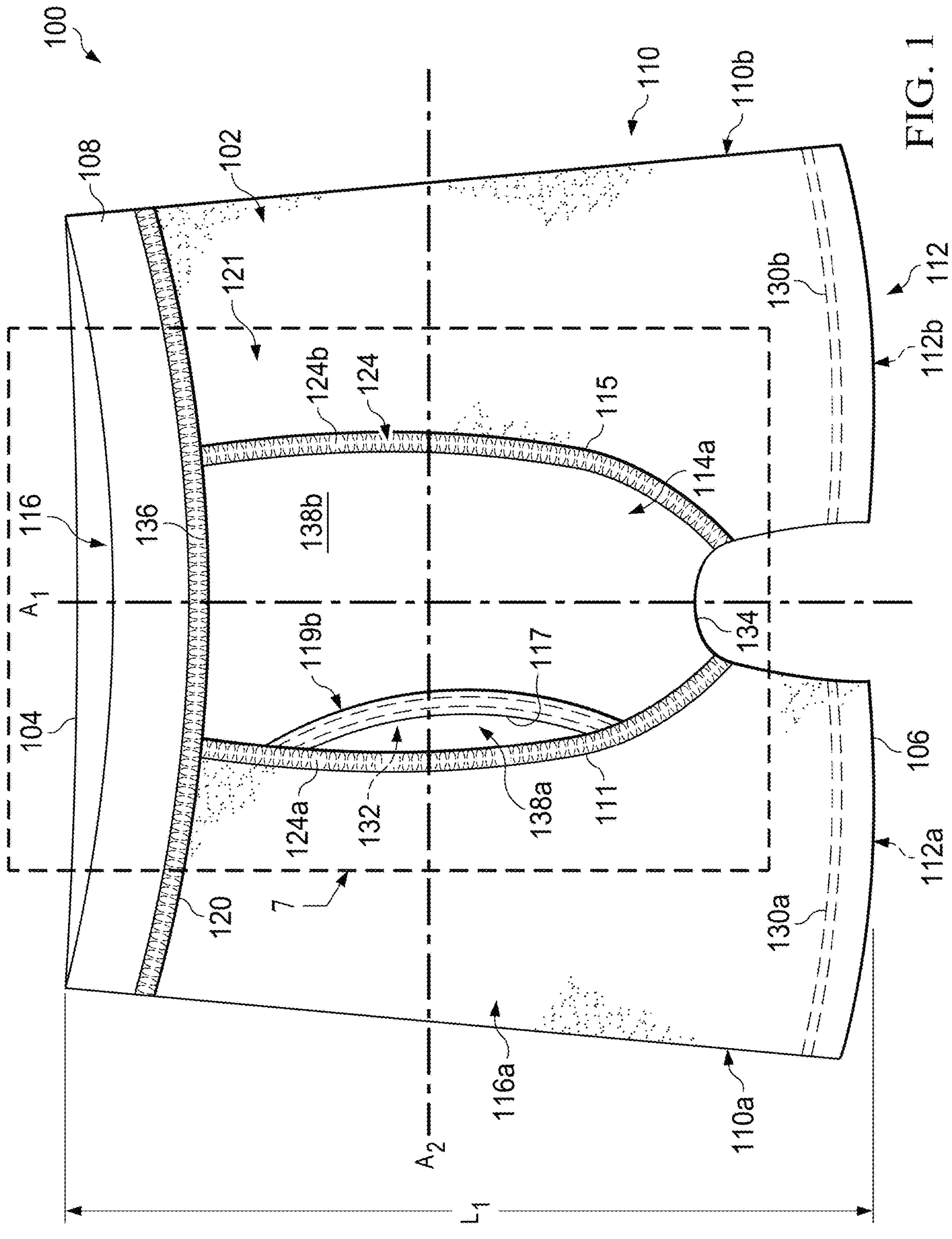
FIG. 1 is a front elevational view of a moisture management garment constructed according to the teachings of the present disclosure.

While the disclosure is susceptible to various modifications and alternative forms, a specific instance thereof is shown by way of example in the drawings and will herein be described in detail. It should be understood, however, that the drawings and detailed description presented herein are not intended to limit the disclosure to the particular instance disclosed, but to the contrary, the intention is to cover all modifications, equivalents, and alternatives falling within the spirit and scope of the present disclosure as defined by the appended claims.

DETAILED DESCRIPTION

Before any instances are described in detail, it is to be understood that the disclosure is not limited in its application to the details of construction and the arrangement of components set forth in the following description or illustrated in the following drawings, which is limited only by the claims that follow the present disclosure. The disclosure is capable of other instances, and of being practiced, or of being carried out, in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

With respect to a garment laid out flat on a horizontal planar surface, a "z-direction" is the direction orthogonal to longitudinal and lateral directions, i.e., a vertical direction relative to the horizontal planar surface.

Figure 8:
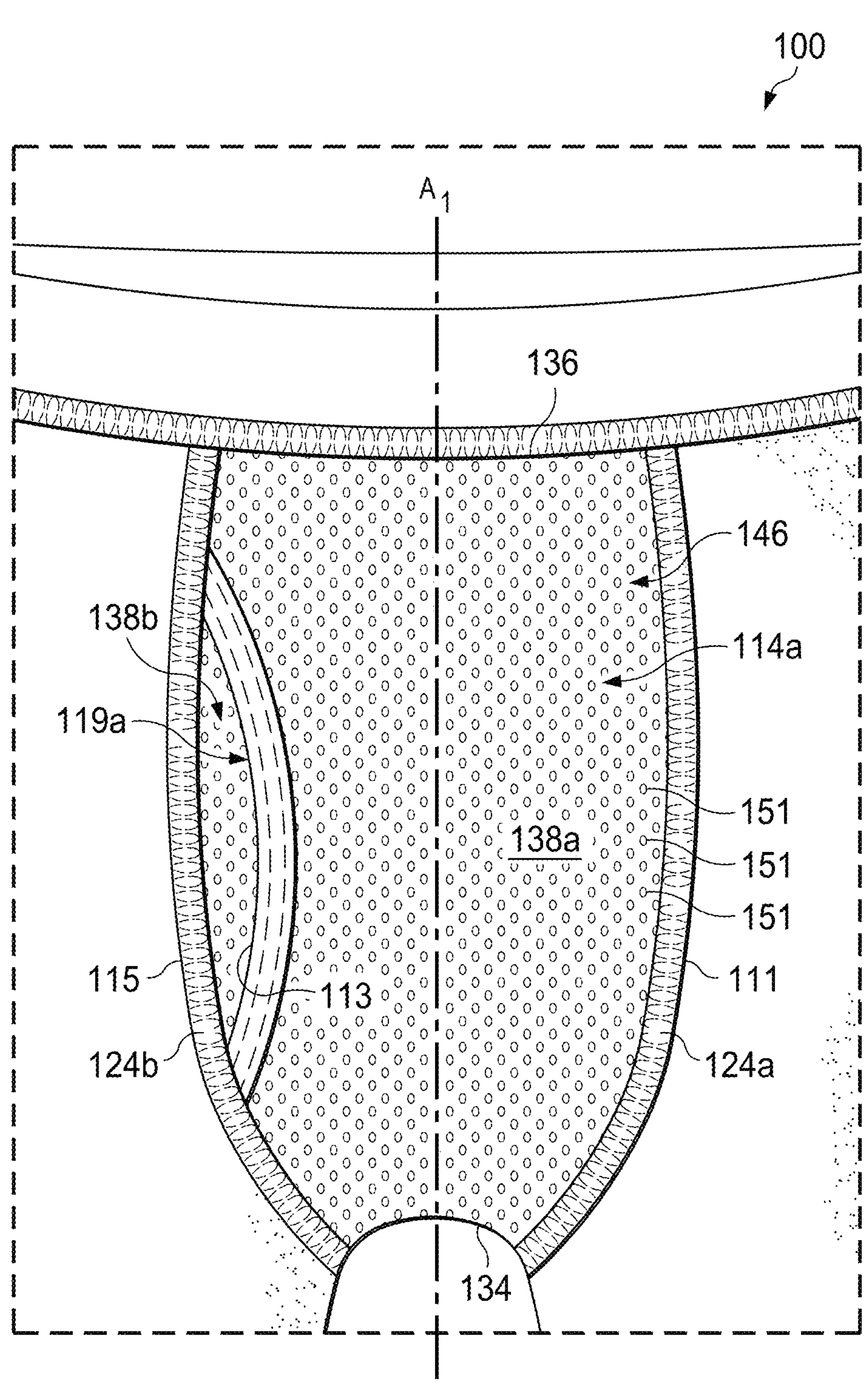
FIG. 8 is an enlarged, elevational view of a wearer-facing surface of the pouch of FIG. 7, the enlarged view created by arranging the garment of FIG. 7 in an inside-out configuration.

With respect to respective layer components in a moisture-absorbent or moisture-adsorbent zone(s) or portion(s) of a garment (e.g., a pouch), when the garment or the pouch is laid out flat on a horizontal planar surface with a wearer-facing surface facing upwardly (as shown in FIG. 8), as between first and second layer components in the moisture-absorbent or moisture-adsorbent portion, the terms "above," "superjacent," "below," "subjacent" and/or "beneath" describe the components' disposition along the z-direction relative to each other. Thus, for example, referring to FIG. 11, a wearer-facing absorbent layer is disposed "above" a water-resistant layer, and conversely, the water-resistant layer is disposed "below" the wearer-facing absorbent or adsorbent layer. "Superjacent" and "subjacent" with respect to two-layer components, mean further that the two-layer components are disposed in direct surface-to-surface contact with each other. Notwithstanding the use of the aforementioned terms, one skilled in the art would also understand that the respective layer components in a moisture-absorbent or moisture-adsorbent zone(s) or portion(s) of the garment may be otherwise arranged and/or may further be disposed proximate or adjacent to each other without being in direct surface-to-surface contact.

With respect to two opposing surfaces of a layer component of a garment, or combination of layer components, when the garment is worn in the garment's intended configuration, "wearer-facing" refers to the surface that faces the wearer's skin and "outward-facing" refers to the surface that faces away from the wearer's skin. With respect to two distinct layered components of a garment, when the garment is worn in the garment's intended configuration, the "wearer-facing" component is the component that is disposed closest to the wearer's skin and the "outward-facing" component is the component that is disposed farthest from the wearer's skin when the garment is worn normally.

The following description is presented to enable a person skilled in the art to make and use instances of the disclosure. Various modifications to the illustrated instances will be readily apparent to those skilled in the art, and the generic principles herein can be applied to other instances and applications without departing from instances of the disclosure. Thus, instances of the disclosure are not intended to be limited to instances shown but are to be accorded the widest scope consistent with the principles and features disclosed herein. The following detailed description is to be read with reference to the figures, in which like elements in different figures have like reference numerals. Skilled artisans will recognize the examples provided herein have many useful alternatives and fall within the scope of instances of the disclosure.

Additionally, while the following discussion may describe features associated with specific devices or instances, it is understood that additional devices and/or features can be used with the described systems and methods, and that the discussed devices and features are used to provide examples of possible instances, without being limited.

As discussed above, perspiration, urination, and other forms of fluid excretion are natural physiological occurrences. However, some individuals may experience occasional or frequent difficulty in controlling the release of urine from their urinary organs. For example, certain individuals may lack full control of their bladder, leading to inadvertent urine leakage throughout the day. In addition, after expelling urine from their bladder, some people may have difficulty ensuring that their urethra is fully evacuated. In such cases, residual urine in the urethra may escape as droplets over time (e.g., when donning an undergarment).

Perspiration or sweat is mostly made up of water and some salt. When one's core body temperature increases above a certain temperature, one's body begins to perspire in order to cool the body, which involves producing sweat and then evaporating the water in the sweat. Excess body heat may convert the water in the perspiration into a gas and, as the excess body heat is used to evaporate the water in the perspiration, the body begins to cool down. Urination is the process by which the body eliminates liquid waste and is primarily composed of water, urea, and various dissolved salts and toxins. When the body processes nutrients and removes metabolic byproducts, it filters excess fluids and waste through the kidneys, which produce urine. Urine is then stored in the bladder until the body signals the need for excretion. Urination serves as a vital mechanism for maintaining the body's fluid balance, removing toxins and other harmful substances, and ensuring proper physiological function. A garment may provide moisture management by adsorbing moisture (e.g., perspiration, urine, etc.) from the skin and transporting it away from the skin for evaporation.

Certain properties of a garment may be selected and optimized to provide improved moisture management. For example, at least a portion of the fabric used to make the garment may be selected and/or modified to enhance adsorption, transport, and/or evaporation of perspiration, urine, and other fluid excretions. Certain fabrics, such as polyester, may be better at adsorbing moisture, transporting moisture away for evaporation, and drying rapidly. Furthermore, within a class of fabrics, such as polyester, certain properties of the fabric and the fibers making up the fabric may affect moisture management more than others.

Without being bound by theory, it is believed that absorption, adsorption, transport, and/or evaporation of moisture (e.g., sweat, urine, etc.) may be affected by fiber properties and yarn and fabric structural parameters, as well as chemical treatment or chemical modification of the yarn or fabric. For example, fiber type, fiber size, fiber shape, yarn denier, filament count, and knit structure, among other properties, may affect absorption, adsorption, transport, and/or evaporation of sweat. More specifically, the knit structure of the fabric may be modified to increase or decrease porosity and pore size, which may affect the water vapor permeability of a fabric. There are also a number of mechanisms that may be involved in moisture management, such as capillary action, denier differential mechanisms, and other processes that may facilitate the movement of perspiration, urine, or other moisture. One or more such mechanisms, fiber types, fiber sizes, fiber shapes, yarn deniers, filament counts, knit structures, chemical treatments, and chemical modifications may be used in the fabrics of the undergarments described herein to facilitate the transport and/or dispersion of moisture such as sweat and urine.

The present disclosure describes undergarments or lower torso garments that include moisture-absorbent or moisture-adsorbent zone(s) or portion(s), for example, a moisture-absorbent or moisture-adsorbent panel or pouch (e.g., a pouch assembly). Generally, the pouch may include a first panel assembly and a second panel assembly each comprising one or more layers of fabric (e.g., at least two layers, at least three layers, at least four layers of fabric, etc.). In some instances, the panel or pouch may include at least two distinct fabric layers, such as at least one fabric layer having moisture-absorbent properties and at least one fabric layer having moisture-resistant or moisture-repellent properties. In certain instances, the pouch may only include a single pouch assembly that may include at least two distinct fabric layers. Generally, in use, the lower torso garment may be designed to cover at least a portion of a wearer's external genitalia and buttocks. In some instances, the lower torso garment may be designed to cover at least a portion of the wearer's legs (e.g., including at least a portion of the inner and outer thighs). The garment may include two leg openings, for example, a first leg opening and a second leg opening, and, in use, the first leg opening may receive one of the wearer's legs, while the second leg opening may receive the wearer's other leg.

In various instances, one or more moisture-absorbent or moisture-adsorbent portions of the lower torso garment may be strategically located to contact areas of the lower body that generate greater amounts of perspiration, urine, or moisture, for example, the genitalia, the buttocks, the inner thighs, other areas of the body, and/or portions thereof, areas of the undergarment proximate or adjacent to the genitals, and/or portions of the undergarment that may be exposed to urine during wear. The garments may be washable, reusable, and composed of any number of different materials and fabrics, including natural, synthetic, and semi-synthetic materials, such as cotton, polyester, nylon, spandex, viscose, modal, lyocell, rayon, and combinations thereof. The garments may be composed of substantially pure fabrics or materials, e.g., 100% cotton, or blends of fabrics and/or materials, e.g., 95% cotton and 5% spandex fabric. In various instances, the fabrics can be woven or knit, and be provided in various knit types, such as jersey, rib, mesh, and/or other knit textures and structures. In certain instances, the undergarments described herein may be designed to transport, adsorb, and/or absorb moisture, in which the moisture is selected from the group consisting of perspiration, urine, and seminal fluids. In some cases, the undergarments described herein may be designed to transport, adsorb, and/or absorb moisture comprising sweat and/or urine.

FIGS. 1-8 illustrate an example garment such as a garment 100 (e.g., a lower torso garment 100) that may be designed to provide moisture management and/or other benefits or properties to a wearer. In some instances, the garment 100 may be provided in the form of a mid-thigh boxer brief style undergarment. However, in other instances, the garment 100 may take on a variety of styles. For example, the garment 100 may be provided in the form of briefs, boxers, boxer-briefs, trunks, low-thigh underwear, base layer or thermal long underwear, a liner for swimwear or running shorts, and/or other garment or undergarment types. For example, the garment 100 may be provided in the form of a brief (see, e.g., a garment 200 of FIGS. 15 and 16).

A longitudinal axis $A_1$ may divide the garment 100 into two portions or halves, namely a left portion and a right portion (see FIGS. 1-4). In some instances, the left and right portions of the garment 100 may be substantially symmetrical with respect to the longitudinal axis $A_1$; however, in other instances, one or more aspects of the garment 100 may be asymmetrical with respect to the longitudinal axis $A_1$. It is understood that the longitudinal axis $A_1$ is an imaginary or hypothetical line referred to herein to describe the structure of the garment 100 more clearly. It is also understood that the longitudinal axis $A_1$ corresponds to a sagittal plane of common anatomical nomenclature. Thus, in use or wear, the left portion of the garment 100 may correspond to the left portion of a wearer's body, and the right portion of the garment 100 may correspond to the right portion of a wearer's body. It is also understood that the directional terms "left" and "right" are used for clarity and may be used interchangeably with numerical terms, such as first and second. In various instances, the garment 100 may have an upper end 104 and a lower end 106 opposing the upper end 104, and the upper and lower ends 104, 106 may be positioned along the longitudinal axis $A_1$.

A lateral axis $A_2$ may divide the garment 100 into upper and lower portions (see FIGS. 1-4). It is understood that the lateral axis $A_2$ is an imaginary or hypothetical line referred to herein to describe the structure of the garment 100 more clearly. It is also understood that the lateral axis $A_2$ is parallel to a transverse plane of common anatomical nomenclature. The lateral axis $A_2$ may be perpendicular to the longitudinal axis $A_1$ and may divide an overall length $L_1$ of the garment 100 into upper and lower portions. It is also understood that the directional terms "upper" and "lower" are used for clarity and may be used interchangeably with numerical terms, such as first and second.

Figures 5A, 5B:
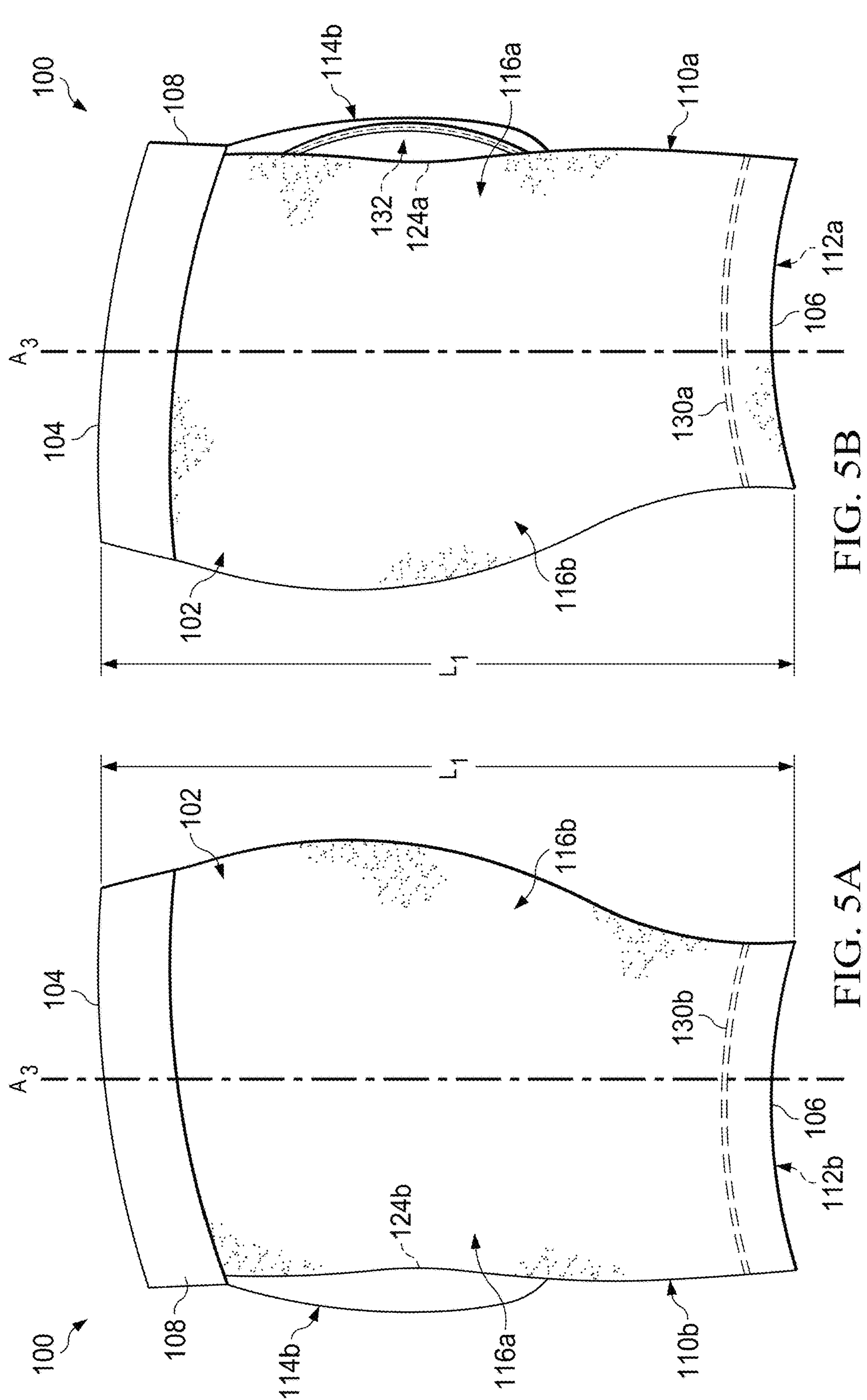
FIG. 5A is a right-side elevational view and FIG. 5B is a left-side elevational view of the moisture management garment of FIG. 3.
Figure 6A:
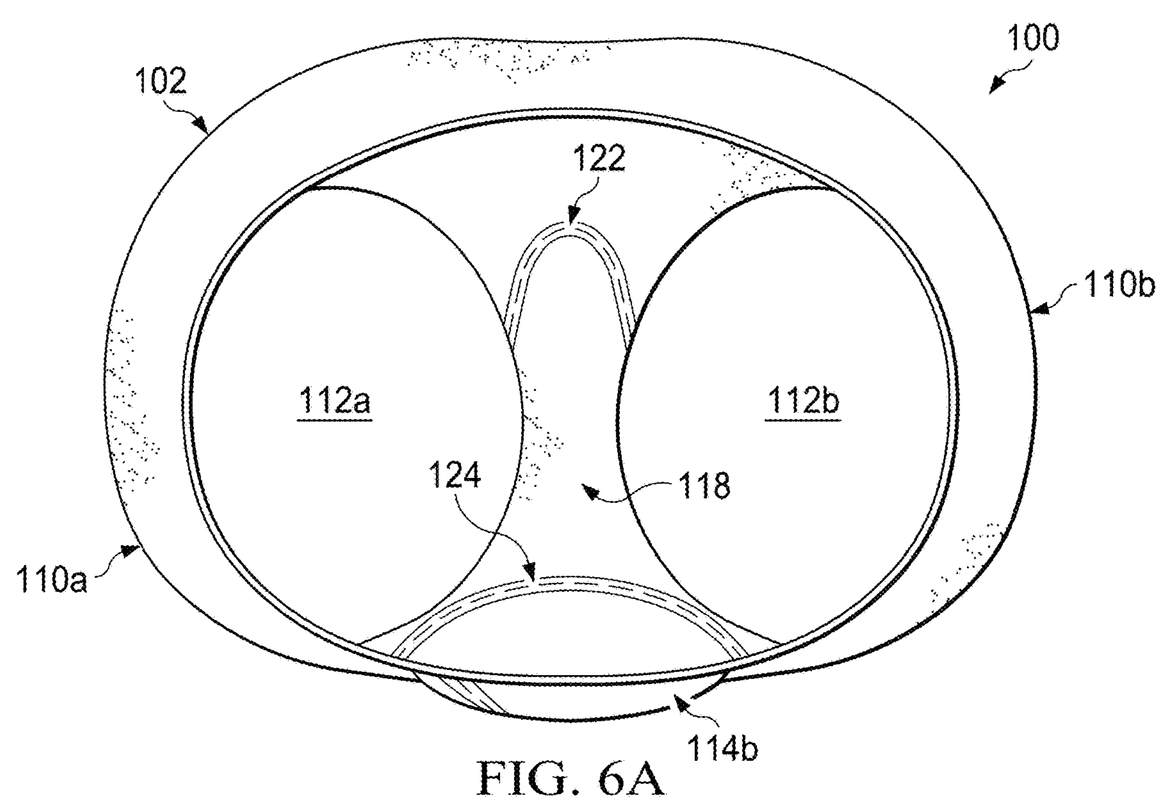
FIG. 6A is a top elevational view and FIG. 6B is a bottom elevational view of the moisture management garment of FIGS. 3 and 4.
Figure 6B:
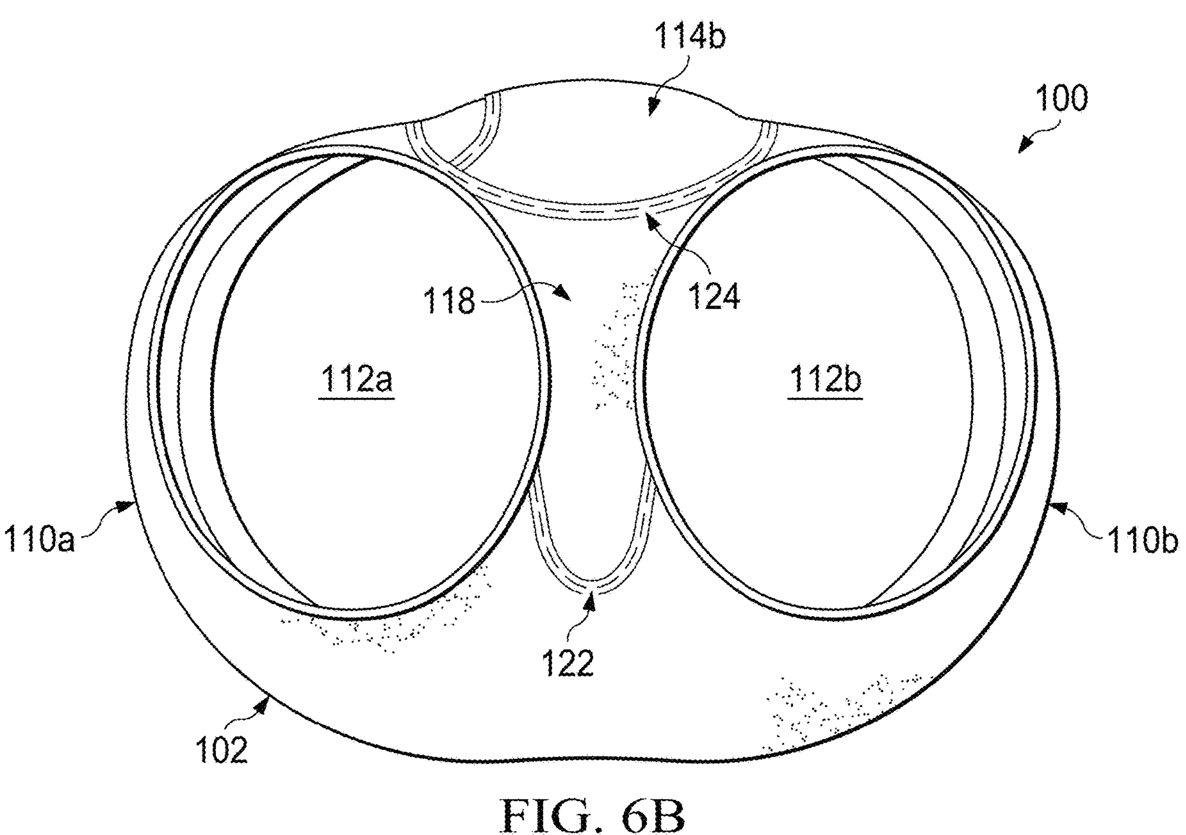
Figure 6C:
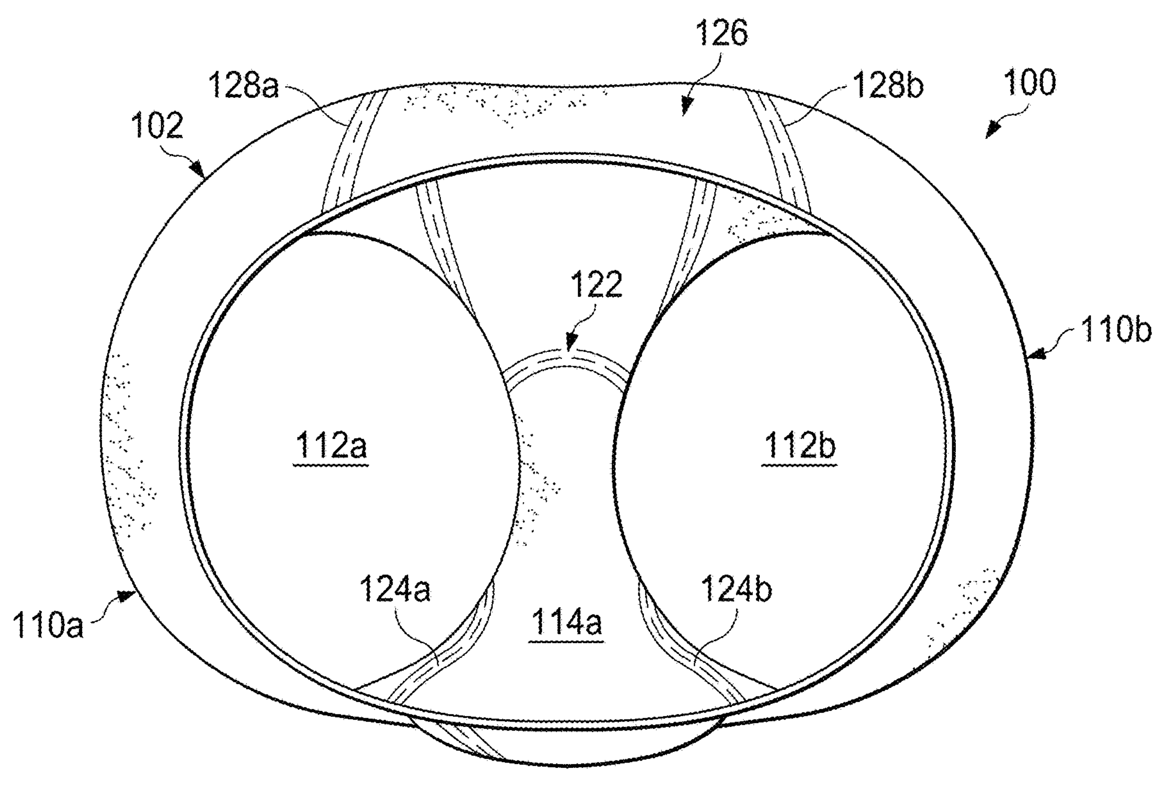
FIG. 6C is a top elevational view and FIG. 6D is a bottom elevational view of the moisture management garment of FIGS. 1 and 2.
Figure 6D:
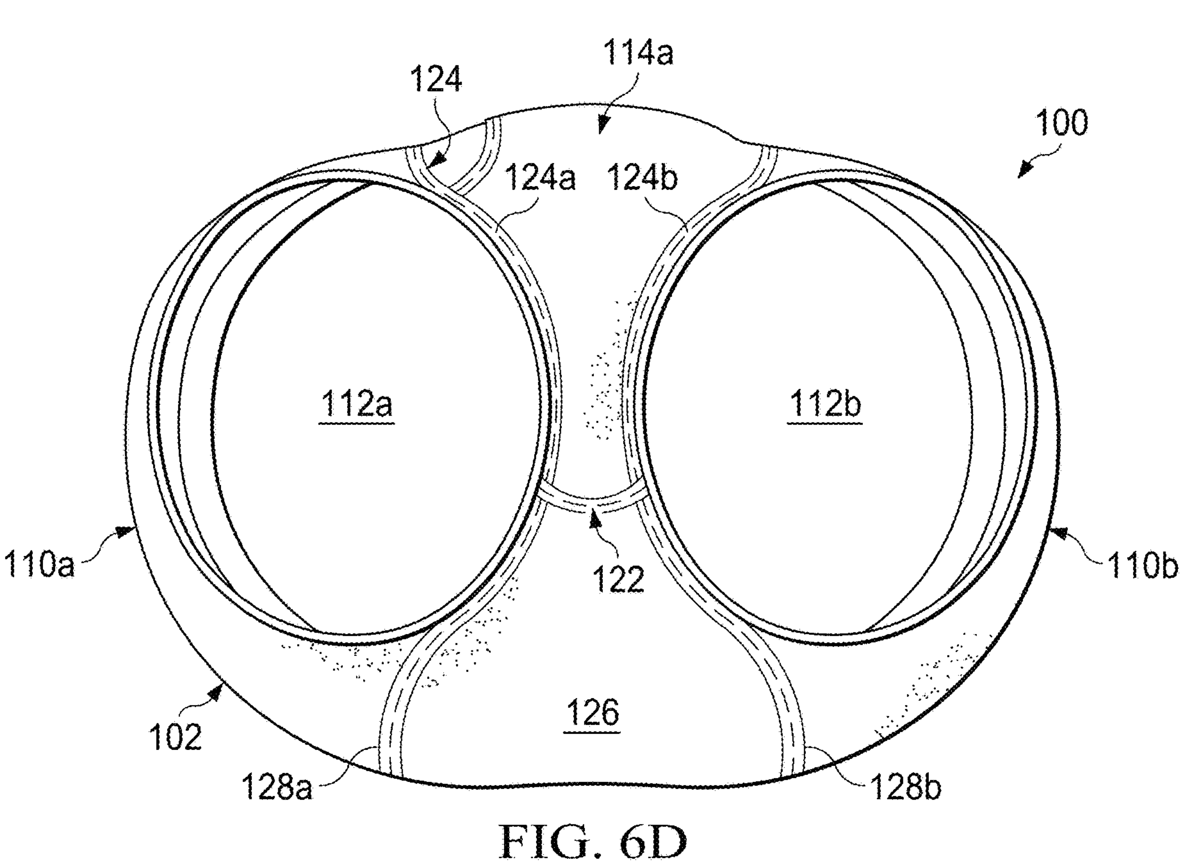

A coronal axis $A_3$ may divide the garment 100 into front and rear portions (see FIGS. 5A and 5B). It is understood that the coronal axis $A_3$ is an imaginary or hypothetical line referred to herein to describe the structure of the garment 100 more clearly. It is also understood that the coronal axis $A_3$ corresponds to a coronal plane of common anatomical nomenclature. Thus, in use, the front portion of the garment 100 corresponds to the front portion of a wearer's body and the rear portion of the garment 100 corresponds to the rear portion of a wearer's body. It is also understood that the directional terms "front" and "rear" are used for clarity and may be used interchangeably with numerical terms, such as first and second.

Figure 2:
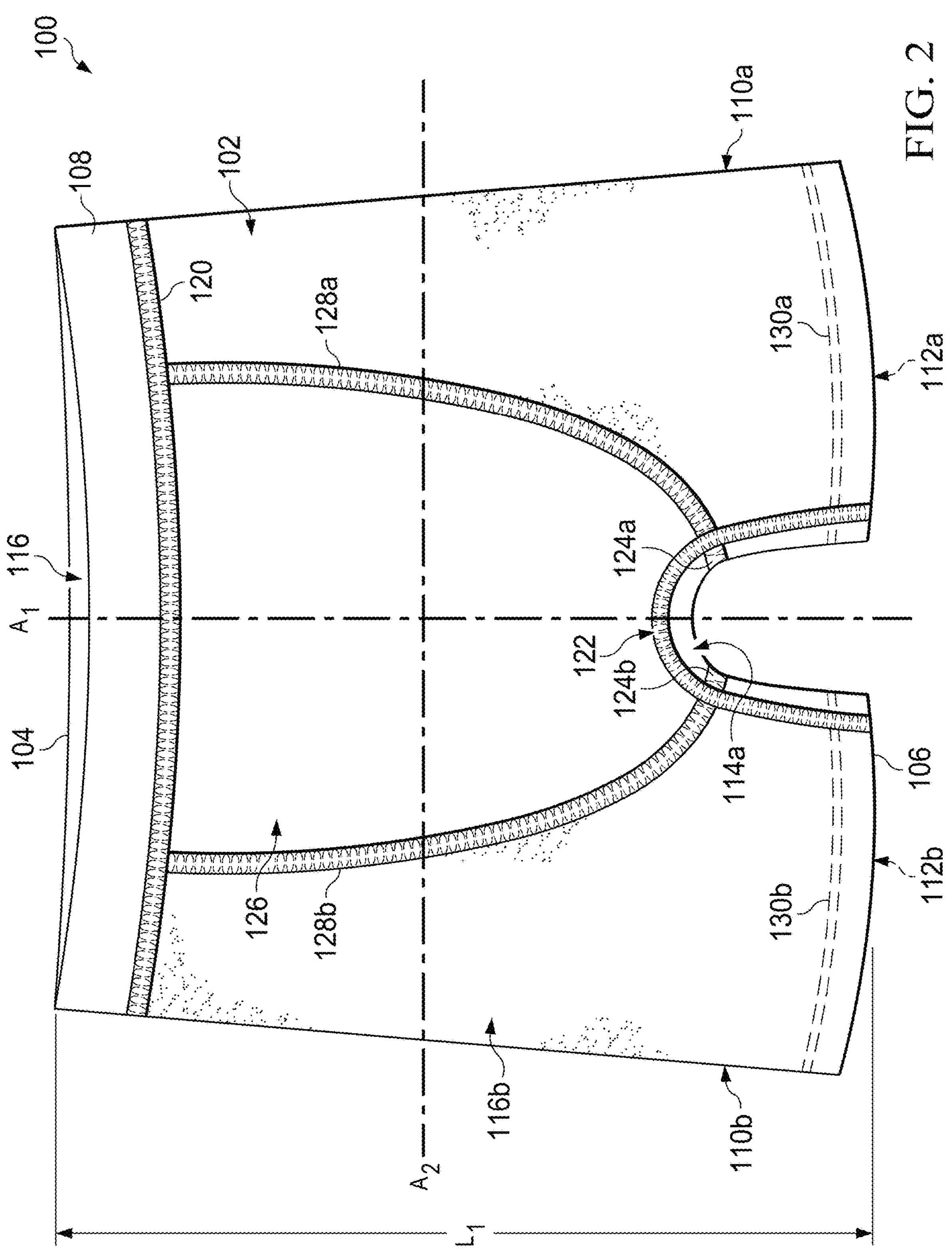
FIG. 2 is a rear elevational view of the moisture management garment of FIG. 1.

As best shown in FIGS. 1 and 2, the garment 100 may be provided in the form of a body 102 having a substantially tubular shape that, in use, partially or completely surrounds a torso of a wearer of the garment 100. For example, the upper end 104 of the garment 100 may be arranged to partially or completely encircle a waist of a wearer when the garment 100 is worn. The example garment 100 may include a waistband 108 disposed at the upper end 104 of the garment 100 and coupled to the body 102. For example, the waistband 108 may be formed integrally with the body 102 or may be coupled thereto via an adhesive agent, sewing, knitting, stitching, bonding agents, fusing, and/or other coupling mechanisms. In some instances, the waistband may include a covered elastic or a turned-back self-fabric waistband that is an extension of the body 102. The waistband 108 may define a waist opening 116 configured to receive a wearer's torso when the garment 100 is worn.

Figure 3:
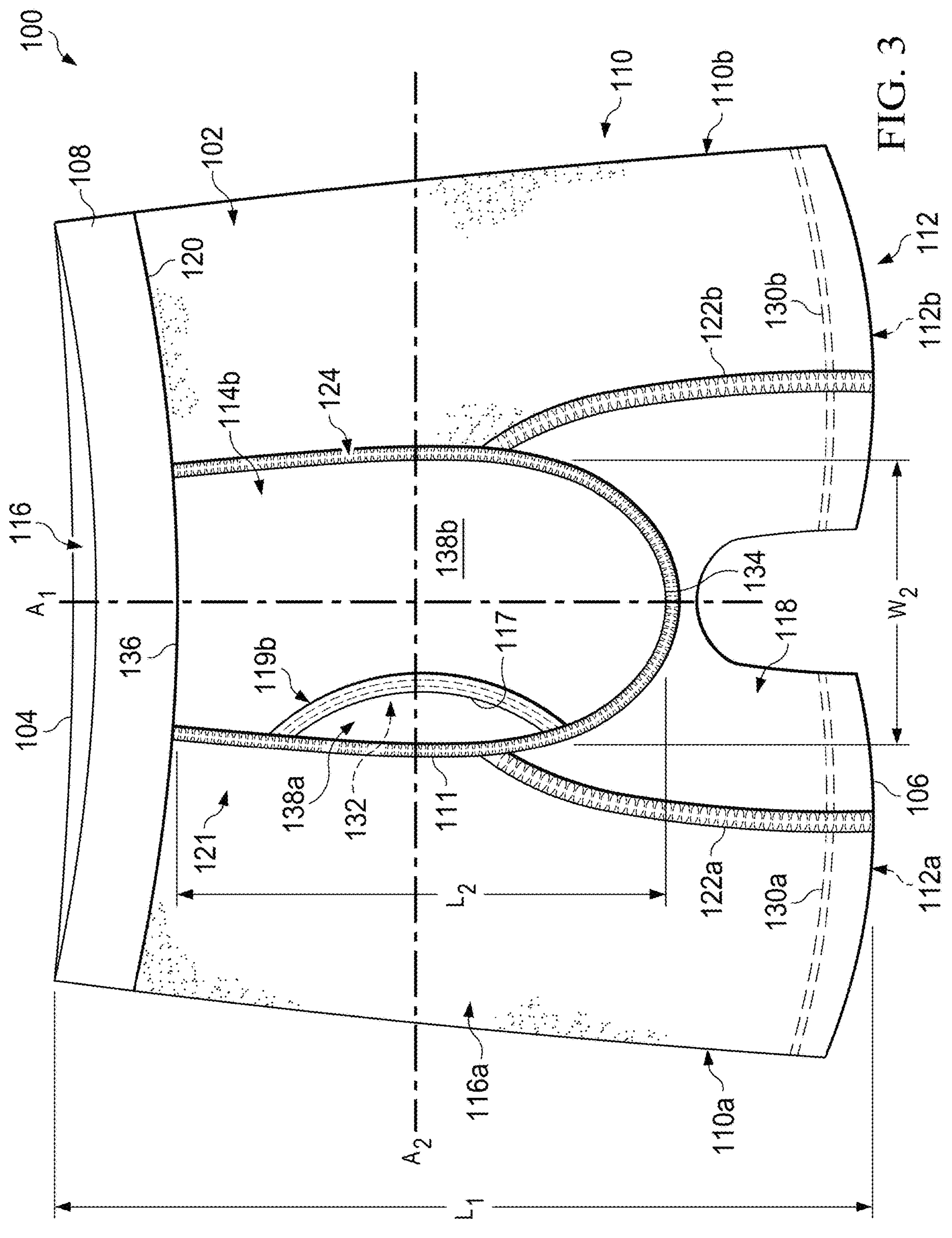
FIG. 3 is a front elevational view of another moisture management garment constructed according to the teachings of the present disclosure.
Figure 4:
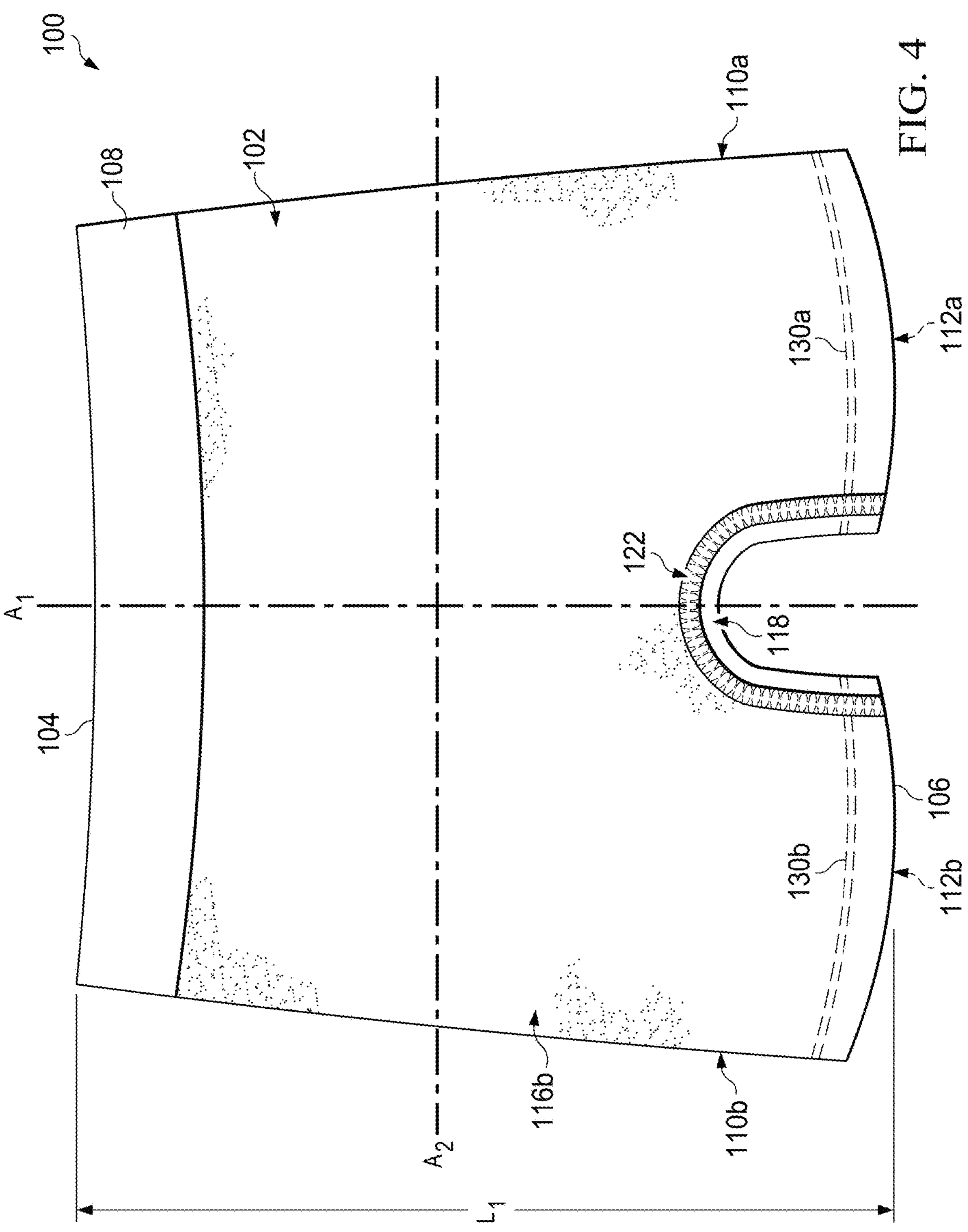
FIG. 4 is a rear elevational view of the moisture management garment of FIG. 3.

The garment 100 may include leg portions 110, including a first or right leg portion 110*a* and a second or left leg portion 110*b*, that may receive the legs of a wearer when the garment 100 is worn. The leg portions 110 may have leg openings 112, including a first or right leg opening 112*a* and a second or left leg opening 112*b*. The leg openings 112 may be disposed at a lower end 106 of the body 102 opposite the upper end 104. The garment 100 may further include at least one moisture-absorbent or moisture-adsorbent panel or pouch 114 (see FIGS. 1 and 3) and, in some instances, the garment 100 may also include a gusset (e.g., a gusset 118 as depicted in FIGS. 3 and 4). Thus, in some instances, the garment 100 may be provided in the form of a body or body 102, left and right leg portions 110*a*, 110*b*, a gusset (e.g., the gusset 118), a moisture-absorbent or moisture-adsorbent front panel 121 which may comprise or consist of the pouch 114, and a waist portion or waistband 108 (collectively referred to as the "garment portions"). Additionally, as best shown in FIGS. 5A and 5B, the garment 100 may include a front lower torso portion 116*a* and a rear lower torso portion 116*b* positioned opposite the front lower torso portion 116*a*. The front and rear lower torso portions 116*a*, 116*b* may be divided by the coronal axis $A_3$ such that the front lower torso portion 116*a* is arranged to correspond to a front of a wearer's body and the rear lower torso portion 116*b* is arranged to correspond to a back of a wearer's body when the garment 100 is worn.

It is understood that "lower torso portion(s)" includes both the front and rear lower torso portions 116*a*, 116*b*, which may be substantially similar to each other (e.g., in dimensions). It is also understood that "leg portions" includes both the left and right leg portions 110*a*, 110*b*, which may be substantially similar to each other (e.g., in dimensions), and that "leg openings" includes both the left and right leg openings 112*a*, 112*b*, which may be substantially similar to each other (e.g., in dimensions).

Generally, the garment 100 may include one or more moisture-absorbent or moisture-adsorbent portions or zones designed to provide moisture management benefits to the wearer. In some instances, the garment 100 may include one moisture-absorbent or moisture-adsorbent portion provided in the form of the pouch 114. However, in other instances, the garment 100 may include more than one moisture-absorbent or moisture-adsorbent portion which may be positioned in any suitable location on the garment 100. In addition, the moisture-absorbent or moisture-adsorbent portions or zones may be durable, washable, reversibly coupled to the garment 100, and/or irreversibly coupled to the garment 100. In addition, the moisture-absorbent or moisture-adsorbent portions or zones may be provided in any portion of the garment 100, including regions in which the wearer typically produces a relatively high amount of sweat or other bodily fluids such as urine (e.g., the wearer's external genitalia, buttocks, lower back, inner thigh, etc.).

In some instances, material(s) forming the pouch 114 may be continuous with materials forming one or more of the body 102 (e.g., the front lower torso portion 116*a* and/or the rear lower torso portion 116*b*), the leg portions 110*a*, 110*b*, the gusset 118, the waistband 108, and/or other portions of the garment 100. Alternatively, material(s) forming the absorbent or adsorbent panel or pouch 114 may be substantially formed of one or more sections or layers of material that are distinct from material(s) forming one or more other portions of the garment 100. In such instances, the pouch 114 may be coupled to one or more other portions of the garment 100 via tape, adhesion, bonding, seams, or other coupling mechanisms. In the non-limiting examples reflected in FIGS. 1 and 3, the pouch 114 may be separate and distinct from and coupled via seams (e.g., pouch seams 124) to the front lower torso portion 116*a*, the gusset 118, and/or the leg portions 110*a*, 110*b*.

The shape of the pouch 114, as well as the arrangement of the one or more layers of the pouch 114, may vary. For example, the garment 100 may include a first pouch 114*a* (e.g., as shown in FIG. 1), a second pouch 114*b* (e.g., as shown in FIG. 3), and/or other pouches imparted with different shapes, sizes, materials, and/or other properties. As used herein, general references to "the pouch 114" may refer to one or both of the first pouch 114*a* and the second pouch 114*b*. For example, the first and second pouches 114*a*, 114*b* may be substantially similar in one or more aspects, and these aspects may be described below with a general reference to the pouch 114. However, the first and second pouches 114*a*, 114*b* may differ in one or more aspects, and these aspects may be described below with particular reference to the first pouch 114*a* or the second pouch 114*b*.

The pouch 114 may be defined by a pouch first end 134 (e.g., located proximate to the leg openings 112*a*, 112*b*) and a pouch second end 136 opposing the pouch first end 134 (e.g., located proximate to the waistband 108). As shown in FIG. 3, the pouch 114 may be defined by a pouch length $L_2$ measured linearly between the pouch first and second ends 134, 136. In some instances, a left portion of the pouch 114 and a right portion of the pouch 114 may be substantially symmetrical across the longitudinal axis $A_1$. Alternatively, a left portion of the pouch 114 and a right portion of the pouch 114 may be substantially asymmetrical across the longitudinal axis $A_1$.

In some instances, the pouch 114 comprises a fly opening 132 that extends therethrough and may be configured to provide access to a wearer's external genitals when the garment 100 is worn. For example, the pouch 114 may include multiple layers of fabric or material, and the fly opening 132 may be provided in the form of or defined by a partial overlap of several (e.g., two) panels of fabric that make up the pouch 114. In the example of FIGS. 1 and 3, the pouch 114 may include a first panel 138*a* (e.g., a fly panel 138*a*) and a second panel 138*b* (e.g., a cover panel 138*b*) positioned adjacent to the first panel 138*a*. For example, the first panel 138*a* may be positioned between the second panel 138*b* and the body of a wearer when the garment 100 is in use. In other instances, the fly opening 132 may be omitted, even in instances where one or both of the first panel 138*a* and the second panel 138*b* are provided.

As an additional example, the second panel 138*b* may overlay at least a portion of the first panel 138*a* when the garment 100 is worn in the intended configuration. As a further example, the second panel 138*b* may be arranged on an exterior of the garment 100 when the garment 100 is worn in the intended configuration. In some such cases, the second panel 138*b* may only partially overlay the first panel 138*a* and a portion of the first panel 138*a* may be visible when the exterior of the garment 100 is viewed. In other such cases, the second panel 138*b* may substantially completely or completely overlay the first panel 138*a* such that the first panel 138*a* is disposed entirely within an interior of the garment 100.

In some instances, the first panel 138*a* may have a first panel coupled edge 111 (e.g., an edge of the first panel 138*a* positioned proximate to the right leg portion 110*a*), which is at least partially coupled to the body 102 of the garment 100 via a first or right pouch seam 124*a*. The first panel 138*a* may also include a first panel decoupled edge 113 (see, e.g., FIG. 8) that is at least partially uncoupled from the body 102. In some instances, a portion of the first panel decoupled edge 113 may be coupled to the body 102. In some cases, the fly opening 132 may not be provided, and substantially all or all of the first panel decoupled edge 113 may be coupled to the body 102.

Likewise, in some instances, the second panel 138*b* may have a second panel coupled edge 115 edge (e.g., an edge of the second panel 138*b* positioned proximate to the left leg portion 110*b*), which is at least partially coupled to the body 102 of the garment 100 via a second or left pouch seam 124*b*, and a second panel decoupled edge 117 that is at least partially uncoupled from the body 102. In some instances, a portion of the second panel decoupled edge 117 may be coupled to the body 102. In some cases, the fly opening 132 may not be provided, and substantially all or all of the second panel decoupled edge 117 may be coupled to the body 102.

The pouch 114 may include one or more fly bindings 119 provided in the form of a portion or region of fabric or stitching configured to reinforce, protect, or otherwise support one or more edges of the first panel 138*a* and/or the second panel 138*b*. For example, in some instances, the second panel 138*b* may include a second panel fly binding 119*b* positioned at least partially on and configured to support the second panel decoupled edge 117 (see, e.g., FIG. 1). Additionally, in some instances, the first panel 138*a* may include a first panel fly binding 119*a* positioned at least partially on and configured to support the first panel decoupled edge 113 (see FIG. 8). The second panel fly binding 119*b* and the first panel fly binding 119*a* may be provided in substantially the same form or may be provided in different forms. In some instances, the second panel fly binding 119*b* and/or the first panel fly binding 119*a* may comprise a natural fabric, a synthetic fabric, a semi-synthetic fabric, and/or combinations thereof. For example, in certain instances, the fly bindings 119*a*, 119*b* may be formed from a substantially similar fabric relative to the body 102. In certain instances, the fly bindings 119*a*, 119*b* may be provided in the form of a fold-over seam that utilizes a portion of the fabric comprising the first panel 138*a* and the second panel 138*b*, respectively. In other instances, however, the fly bindings 119*a*, 119*b* may be provided in any suitable form and may be formed from any suitable material.

Because the second panel decoupled edge 117 and the first panel decoupled edge 113 are at least partially decoupled from the body 102, the fly opening 132 may have an open configuration and a closed configuration. In the closed configuration, as shown in FIGS. 1 and 3, the second panel 138*b* may at least partially overlap the first panel 138*a* and both the second panel 138*b* and the first panel 138*a* may cover the fly opening 132. In the open configuration (not shown), however, the first panel decoupled edge 113 may be moved away from the second panel decoupled edge 117 such that the first panel decoupled edge 113 and the second panel decoupled edge 117 at least partially define the fly opening 132.

The first panel 138*a* and the second panel 138*b* may be made of the same or different materials. In some instances, one or both of the first panel 138*a* and the second panel 138*b* may be provided in the form of two or more distinct layers of fabric or material. For example, the first panel 138*a* and/or the second panel 138*b* may include at least one moisture-absorbent or moisture-adsorbent layer and at least one moisture-repellent or moisture-resistant layer, as described in further detail below with reference to FIG. 9A. In such instances, the first panel 138*a* and the second panel 138*b* may be provided in the form of a "first panel assembly" or "fly panel assembly" and a "second panel assembly" or "cover panel assembly," each including two or more layers of fabric or material. However, in other instances, the first panel 138*a* and/or the second panel 138*b* may be provided in the form of a single layer of fabric or material. In still other instances, the fly opening 132 may be omitted. For example, the pouch 114 may be provided in the form of a single panel of fabric (e.g., including a single layer or multiple layers) extending between the pouch seams 124*a*, 124*b*.

The pouch 114 may be imparted with various shapes depending on the desired aesthetic, comfort, moisture management, and/or other characteristic of the garment 100. For example, when viewing a front of the garment 100, the pouch 114 may be imparted with a U-shape, a U-shape imparted with a flat bottom, a tulip-shape, a substantially rectangular shape, an hourglass-shape, a wineglass-shape, a teardrop-shape, and/or a virtually endless number of other suitable shapes. For illustrative purposes, a first pouch 114*a* (see FIGS. 1, 2, 6C, and 6D) and a second pouch 114*b* (see FIGS. 3, 4, 6A, and 6B) are depicted and described herein. In addition, the pouch 114 may extend to the rear lower torso portion 116*b* and/or may be coupled to the gusset 118, which may impact the overall shape of the pouch 114. However, it should be understood that the pouch 114 may be provided in different forms, imparted with different shapes, etc.

As shown in FIG. 1, the first pouch 114*a* may be substantially U-shaped when viewing the front of the garment 100. For example, the first pouch 114*a* may be imparted with a U-shape having a substantially flat bottom. In such instances, the pouch seams 124*a*, 124*b* defining the shape of the first pouch 114*a* may be positioned on at least a portion of the front lower torso portion 116*a* and at least a portion of the rear lower torso portion 116*b*. Therefore, the first pouch 114*a* may be at least partially positioned on each of the front and rear lower torso portions 116*a*, 116*b*. For example, the pouch scams 124*a*, 124*b* may begin at a portion of the waistband 108 positioned on the front lower torso portion 116*a* and extend at least partially onto the rear lower torso portion 116*b* before reaching a rear seam 122, where the pouch seams 124*a*, 124*b* may terminate (see FIG. 2). Alternatively, the pouch seams 124*a*, 124*b* of the first pouch 114*a* may extend across a greater portion of the rear lower torso portion 116*b*; for example, in some instances, the pouch seams 124*a*, 124*b* may extend to a portion of the waistband 108 located on the rear lower torso portion 116*b*. A width of the first pouch 114*a* may be approximately constant along a portion or substantially all of the pouch length $L_2$. However, the first pouch 114*a* may gradually taper (e.g., decrease in width) along the longitudinal axis $A_1$ toward the pouch first end 134, or the first pouch 114*a* may be imparted with other shapes or dimensions.

In some instances, it may be advantageous for at least a portion of the first pouch 114*a* (or the second pouch 114*b*) to be positioned on the rear lower torso portion 116*b* such that a portion of the first pouch 114*a* is positioned at a lower end of the garment. For example, such an arrangement of the first pouch 114*a* (or the second pouch 114*b*) may position a portion of the first pouch 114*a* beneath the external genitals of a wearer when the garment 100 is worn in its intended configuration. In addition, the first pouch 114*a* (or the second pouch 114*b*) may be located in a crotch region of the garment 100). The force of gravity may in some instances cause moisture that is absorbed, transported, or otherwise collected by the portion of the first pouch 114*a* to travel downward, which may lead to moisture accumulating at a region of the first pouch 114*a* positioned beneath the wearer's external genitals. In addition, extending the first pouch 114*a* to the lower end of the garment 100 may also facilitate the adsorption, absorption, and/or transport of moisture that is not captured by areas of the first pouch 114*a* that are positioned above the crotch region. Thus, providing a portion of the first pouch 114*a* in the lower portion of the garment 100 may facilitate further moisture management such that moisture is prevented or restricted from accumulating in the garment 100.

Turning to FIG. 3, the second pouch 114*b* may be substantially U-shaped. In such instances, the shape of the second pouch 114*b* may be defined by a single pouch seam 124 that is positioned entirely (or substantially entirely) on the front lower torso portion 116*a*. Therefore, the second pouch 114*b* may be positioned entirely (or substantially entirely) on the front lower torso portion 116*a*. The garment of FIG. 3 may also include the rear seam 122 (see FIG. 4), however, the pouch seam 124 of the second pouch 114*b* may not be connected to the rear seam 122. In these instances, a width of the second pouch 114*b* may be approximately constant along most or substantially all of the pouch length $L_2$. However, the second pouch 114*b* may gradually taper (e.g., decrease in width) toward the pouch first end 134. Alternatively, the second pouch 114*b* may be provided in the form of a bullet-shaped or substantially rectangular body (not shown) or maybe imparted with any other suitable shape.

As shown in FIG. 3, the pouch length $L_2$ of the pouch 114, or the ratio between the pouch length $L_2$ of the pouch 114 and the overall length $L_1$ of the garment 100, may vary. While the pouch length $L_2$ is depicted in FIG. 3 relative to the second pouch 114*b*, it should be understood that the below description of the pouch length $L_2$ may apply equally to the first pouch 114*a*, the second pouch 114*b*, and/or other forms of the pouch 114. For example, the pouch length $L_2$ may be imparted with a value that is about 5% of the overall length $L_1$ to about 95% of the overall length $L_1$, although the pouch length $L_2$ may be somewhat less or even greater than these values For example, the pouch length $L_2$ may be imparted with a value that is at least about 5%, or at least about 10%, or at least about 15%, or at least about 20%, or at least about 25%, or at least about 30%, or at least about 35%, or at least about 40%, or at least about 45%, or at least about 50%, or at least about 55%, or at least about 60%, or at least about 65%, or at least about 70%, or at least about 75%, or at least about 80%, or at least about 85%, or at least about 90%, or no more than about 95% of the overall length $L_1$. Alternatively, the pouch length $L_2$ may be imparted with a value that is 5% of the overall length $L_1$ to 95% of the overall length $L_1$, although the pouch length $L_2$ may be somewhat less or even greater than these values. For example, the pouch length $L_2$ may be imparted with a value that is at least 5%, or at least 10%, or at least 15%, or at least 20%, or at least 25%, or at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or no more than 95% of the overall length $L_1$.

In some instances, the pouch 114 may be substantially completely or completely positioned on the front lower torso portion 116*a* (see FIG. 3). However, as described above with respect to the first pouch 114*a* of FIG. 1, in other instances, the pouch 114 may extend across at least a portion of the front lower torso portion 116*a* and the rear lower torso portion 116*b*. In some such instances, the pouch 114 may extend entirely between two opposing locations along the waistband 108 or along the waist seam 120 (e.g., the pouch 114 may extend between a first location along the waistband 108 positioned on the front lower torso portion 116*a* and a second location along the waistband 108 positioned on the rear lower torso portion 116*b*). Thus, in some instances, the pouch length $L_2$ may be imparted with a value that is about 95% of the overall length $L_1$ of the garment 100 to about 200% of the overall length $L_1$ of the garment 100, although the pouch length $L_2$ may be somewhat less or even greater than these values. For example, the pouch length $L_2$ may be imparted with a value that is at least about 95%, or at least about 100%, or at least about 105%, or at least about 110%, or at least about 115%, or at least about 120%, or at least about 125%, or at least about 130%, or at least about 135%, or at least about 140%, or at least about 145%, or at least about 150%, or at least about 155%, or at least about 160%, or at least about 165%, or at least about 170%, or at least about 175%, or at least about 180%, or at least about 185%, or at least about 190%, or at least about 195%, or no more than about 200% of the overall length $L_1$. Alternatively, the pouch length $L_2$ may be imparted with a value that is 95% of the overall length $L_1$ to 200% of the overall length $L_1$, although the pouch length $L_2$ may be somewhat less or even greater than these values. For example, the pouch length $L_2$ may be imparted with a value that is at least 95%, or at least 100%, or at least 105%, or at least 110%, or at least 115%, or at least 120%, or at least 125%, or at least 130%, or at least 135%, or at least 140%, or at least 145%, or at least 150%, or at least 155%, or at least 160%, or at least 165%, or at least 170%, or at least 175%, or at least 180%, or at least 185%, or at least 190%, or at least 195%, or no more than 200% of the overall length $L_1$.

Additionally, a surface area of the pouch 114 may vary relative to an overall surface area of the garment 100 or relative to a surface area of one or more other portions of the garment 100 (e.g., the body 102). For example, the garment 100 may be imparted with a first outward-facing surface area, which may be equal to the total surface area of the outward-facing surfaces of all portions of the garment 100 when the garment 100 is worn in its intended configuration. The pouch 114 may be imparted with a second outward-facing surface area, which may be configured to occupy a portion or a predetermined percentage of the first outward-facing surface area. In some instances, the second outward-facing surface area of the pouch 114 may be imparted with a value that is about 5% to about 50% of the first outward-facing surface area of the garment 100, although the second outward-facing surface area of the pouch 114 may be imparted with a value that is somewhat less or even greater than these values. For example, the second outward-facing surface area of the pouch 114 may be imparted with a value that is at least about 5%, or at least about 8%, or at least about 10%, or at least about 13%, or at least about 15%, or at least about 18%, or at least about 20%, or at least about 23%, or at least about 25%, or at least about 28%, or at least about 30%, or at least about 33%, or at least about 35%, or at least about 38%, or at least about 40%, or at least about 43%, or at least about 45%, or at least about 48%, or no more than about 50% of the first outward-facing surface area of the garment 100. Alternatively, the second outward-facing surface area of the pouch 114 may be imparted with a value that is 5% to 50% of the first outward-facing surface area of the garment 100, although the second outward-facing surface area of the pouch 114 may be imparted with a value that is somewhat less or even greater than these values. For example, the second outward-facing surface area of the pouch 114 may be imparted with a value that is at least 5%, or at least 8%, or at least 10%, or at least 13%, or at least 15%, or at least 18%, or at least 20%, or at least 23%, or at least 25%, or at least 28%, or at least 30%, or at least 33%, or at least 35%, or at least 38%, or at least 40%, or at least 43%, or at least 45%, or at least 48%, or no more than 50% of the first outward-facing surface area of the garment 100.

As another example, the garment 100 may be imparted with a first wearer-facing surface area, which may be equal to the total surface area of the wearer-facing surfaces of all portions of the garment 100 when the garment 100 is worn in its intended configuration. The pouch 114 may be imparted with a second wearer-facing surface area, which may be a portion or predetermined percentage of the first wearer-facing surface area. In some instances, the second wearer-facing surface area may be imparted with a value that is about 5% to about 35% of the first wearer-facing surface area of the garment 100, although the second wearer-facing surface area of the pouch 114 may be imparted with a value that is somewhat less or even greater than these values. For example, the second wearer-facing surface area of the pouch 114 may be imparted with a value that is at least about 5%, or at least about 8%, or at least about 10%, or at least about 13%, or at least about 15%, or at least about 18%, or at least about 20%, or at least about 23%, or at least about 25%, or at least about 28%, or at least about 30%, or at least about 33%, or no more than about 35% of the first wearer-facing surface area of the garment 100. Alternatively, the second wearer-facing surface area of the pouch 114 may be imparted with a value that is 5% to 35% of the first wearer-facing surface area of the garment 100, although the second wearer-facing surface area of the pouch 114 may be imparted with a value that is somewhat less or even greater than these values. For example, the second wearer-facing surface area of the pouch 114 may be imparted with a value that is at least 5%, or at least 8%, or at least 10%, or at least 13%, or at least 15%, or at least 18%, or at least 20%, or at least 23%, or at least 25%, or at least 28%, or at least 30%, or at least 33%, or no more than 35% of the first wearer-facing surface area of the garment 100.

It should be understood that the shape and dimensions of the pouch 114, or of portions of the pouch 114 such as the first panel 138*a* and/or the second panel 138*b*, may be different from the shapes and dimensions depicted and described herein. For example, the pouch 114 may be imparted with a variety of polygonal shapes (e.g., a substantially rectangular shape, a substantially triangular shape, etc.), irregular shapes, and/or may be defined by any combination of straight, curved, or jagged lines (e.g., stitch lines or seams).

When the garment 100 is worn or in use, a front panel 121 (see FIGS. 1 and 3) of the pouch 114 may be adjacent to and/or may be arranged to support at least a portion of the male anatomy or external male genitalia of a wearer. In addition, the gusset 118 (if provided) may be adjacent or proximate to a wearer's crotch or crotch region and/or the wearer's inner thighs. In various instances, the pouch 114, the gusset 118, and/or other portions of the garment 100 (e.g., portions proximate to a lower back or inner thigh region of a wearer's body when the garment 100 is worn) may be provided in the form of moisture-absorbent or moisture-adsorbent portions or assemblies of the garment 100 and may include one or more layers of fabric or material designed for moisture-management. For example, the pouch 114 may be provided in the form of a moisture-absorbent or moisture-adsorbent pouch 114 including two or more layers of fabrics and/or components, as described in further detail below with reference to FIGS. 9A-14. In some instances, the pouch 114 may be formed integrally with the body 102 and/or the gusset 118. However, in other instances, the pouch 114 may be coupled to the body 102, the gusset 118, and/or other portions of the garment 100 via seams, adhesion, bonding, tape, and the like.

In some instances, materials respectively forming one or more portions of the garment 100 such as the body 102, the waistband 108, the leg portions 110*a*, 110*b*, the pouch 114, the front and rear lower torso portions 116*a*, 116*b*, the gusset 118, and/or other portions of the garment 100 may be provided in substantially the same form or in different forms. For example, one or more portions or components of the garment 100 may be made from any natural, synthetic, or semi-synthetic fabrics, fibers, or materials, including blends thereof. In some instances, one or more portions of the garment 100 may include a fabric or material that comprises cotton, polyester, an elastic fabric (e.g., spandex), other materials or fabrics, or blends thereof.

As shown in FIGS. 1-4, certain portions of the garment 100 (e.g., the body 102, the leg portions 110*a*, 110*b*, the pouch 114, the gusset 118, the waistband 108, and/or other portions of the garment 100) may be coupled to certain other portions of the garment 100 via seams, adhesion, bonding, tape, and the like. For example, one or more portions of the garment 100 may be coupled together via one or more seams (e.g., chainstitched seams, lockstitched seams, overlock stitched seams, and/or other suitable seams).

As best shown in FIG. 1, in some instances, a waist seam 120 may be provided to couple at least a portion of the waistband 108 to at least a portion of the body 102 (e.g., to the front lower torso portion 116*a* and/or the rear lower torso portion 116*b*) and/or at least a portion of the pouch 114. In general, the pouch 114 may be positioned on or in the front lower torso portion 116*a* and may be coupled to at least a portion of the body 102 (e.g., to the front lower torso portion 116*a*, the leg portions 110*a*, 110*b*, or other portions of the garment 100) via one or more pouch seams 124. For example, the garment 100 may include a right pouch seam 124*a* positioned proximate to the right leg portion 110*a* and a left pouch seam 124*b* positioned proximate to the left leg portion 110*b*, and the pouch seams 124*a*, 124*b* may couple the pouch 114 to the adjacent portions of the body 102. In such instances, the pouch seams 124*a*, 124*b* may be provided as distinct, independent seams. However, in other instances, the pouch seams 124 may be provided in the form of a single, continuous seam. For example, in certain instances, the pouch 114 may be substantially U-shaped and may be coupled to the body 102 via a single, continuous pouch seam 124, as shown in FIG. 3.

In some instances, the pouch seams 124*a*, 124*b* may couple one or more of the fabric layers of the pouch 114 together. Additionally, or alternatively, the pouch seams 124*a*, 124*b* may couple the pouch 114 to the body 102 (e.g., to the front lower torso portion 116*a*, the rear lower torso portion 116*b*, the gusset 118, and/or the leg portions 110*a*, 110*b*). For example, the pouch 114 may be coupled to the leg portions 110*a*, 110*b* via the right and left pouch seams 124*a*, 124*b*, respectively. The pouch seams 124*a*, 124*b* may be provided as any type of suitable scam known in the art. In other instances, a first pouch seam 124 may be used to couple the layers of the pouch 114 together and a second pouch seam 124 may be used to couple the pouch 114 to at least a portion of the body 102, for example, the front lower torso portion 116*a*, and/or the leg portions 110*a*, 110*b*. In other examples, the layers of the pouch 114 may be coupled by bonding, adhesion, and the like, and the pouch 114 may be coupled to at least a portion of the body 102 (e.g., the front lower torso portion 116*a* and/or the leg portions 110*a*, 110*b*) via a single, continuous pouch scam 124.

The exact position and arrangement of the pouch seams 124*a*, 124*b* may affect the comfort of the garment 100, as seams provided on the wearer-facing surface of the pouch 114 may contact the wearer's skin. Placement of the pouch seams 124*a*, 124*b* around a perimeter of the pouch 114 may help improve in-wear comfort by reducing contact of the pouch seams 124*a*, 124*b* with the wearer's skin. Furthermore, the pouch seams 124*a*, 124*b* may be provided in other positions and arrangements besides those described herein. In certain instances, the pouch 114 may include one or more additional seams or features (e.g., designed to provide support to a wearer, impart the pouch 114 or the garment 100 with desired structural characteristics, etc.). For example, in some instances, the pouch 114 may include a central pouch seam (not shown) that is substantially aligned with the longitudinal axis $A_1$ and extends at least partially between pouch first and second ends 134, 136. Further, in certain instances, the pouch 114 may include a dart (not shown). For example, the dart may be located proximate to the pouch first end 134 and may be positioned in a substantially central location with respect to the pouch 114 (e.g., proximate to the longitudinal axis A1). In further instances, the pouch 114 may include further additional components or features, or one or more of the aforementioned components or features may be omitted.

As shown in FIG. 3, in some instances, at least a portion of the second pouch 114*b* may be coupled to at least a portion of the gusset 118 via the pouch seam 124. Additionally, at least a portion of the gusset 118 may be coupled to at least a portion of the body 102 (e.g., one or both of the front and rear lower torso portions 116*a*, 116*b*) and/or to at least a portion of the leg portions 110*a*, 110*b* via one or more rear seams 122. For example, in some instances, the pouch seam 124 of the second pouch 114*b* may be at least partially coupled to or may contact the rear scam 122. In some instances, the gusset 118 may form at least a portion of each of the leg portions 110*a*, 110*b*, as shown in FIGS. 3 and 4. However, in other instances, the gusset 118 may be omitted (see, e.g., FIGS. 1 and 2).

In certain instances, the garment 100 may include a rear panel 126, which may be disposed on or in the rear lower torso portion 116*b*. In some instances, the rear panel 126 may be substantially U-shaped; however, in other instances, the rear panel 126 may be imparted with any suitable shape. The rear panel 126 may be coupled to the body 102 (e.g., to the rear lower torso portion 116*b* and/or the leg portions 110*a*, 110*b*) via one or more rear panel seams 128, such as a left rear panel seam 128*a* and a right rear panel seam 128*b*, as shown in FIG. 2. In some examples, the rear panel 126 may also be coupled to the gusset 118 via the rear seam 122 and/or via the rear panel scams 128*a*, 128*b*. As shown in FIG. 2, in some instances, the rear panel seams 128*a*, 128*b* may be imparted with some degree of curvature and may extend at least partially between the waistband 108 (or the waist seam 120) and the rear seam 122 and/or the pouch seams 124*a*, 124*b*. However, in other instances, the rear panel 126 may be substantially rectangular. In such instances, the rear panel seams 128*a*, 128*b* may be substantially linear and may extend at least partially between the waistband 108 (or the waist seam 120) and the leg portion hem seams 130*a*, 130*b* (or a distal end of the leg portions 110*a*, 110*b*). In further instances, the rear panel 126 may be omitted (see, e.g., FIG. 4).

In certain instances, the rear panel 126 may be imparted with moisture management properties such that the rear panel 126 is substantially similar to the pouch 114 in one or more respects. For example, the rear panel 126 may include a fabric layer or assembly of fabric layers that is substantially similar to the first panel 138*a* and/or the second panel 138*b*. In such instances, the rear panel 126 may be imparted with a different shape, different dimensions, and/or other different characteristics as compared to the pouch 114.

In other instances, the garment 100 may be constructed in a seamless or partially seamless configuration (e.g., via circular knitting) and/or in a tubular construction. In further instances, one or more of the aforementioned seams may be repositioned, combined with one or more other seams, provided continuously with one or more other seams, or omitted from the garment 100.

The garment 100 may optionally include a right leg portion hem seam 130*a* and a left leg portion hem seam 130*b* disposed proximate or adjacent to the leg openings 112*a*, 112*b* of the leg portions 110*a*, 110*b*, respectively. In addition, the leg portion hem seams 130*a*, 130*b* may extend around at least a portion of a perimeter of each of the leg openings 112*a*, 112*b*.

Thus, the garment 100 may include one or more seams including, but not limited to, the waist seam 120, the rear seam 122, the pouch seams 124*a*, 124*b*, the rear panel seams 128*a*, 128*b*, the leg portion hem seams 130*a*, 130*b*, and/or other seams not specifically described herein. Any one or more of the aforementioned seams may be provided in the form of 3-thread overlock stitched seams, chainstitched seams, or any other suitable form of seam. In some instances, one or more seams of the garment 100 that are depicted as distinct or independent may be instead provided in the form of a continuous seam. For example, in some instances, the garment 100 includes the right pouch seam 124*a* and the left pouch seam 124*b* (see FIG. 1), while in other instances, the garment 100 includes a single pouch seam 124 that extends along a portion of or the substantial entirety of an outer edge of the pouch 114 (see FIG. 3).

In some instances, one or more of the pouch seams 124*a*, 124*b*, the rear panel seams 128*a*, 128*b*, and the rear scam 122 may be substantially similar and/or symmetrical across the longitudinal axis $A_1$. The pouch 114 may also substantially symmetrical across the longitudinal axis $A_1$. Additionally, in some instances, the longitudinal axis $A_1$ may divide the waist seam 120 into two substantially similar and/or symmetrical portions or halves across the longitudinal axis $A_1$. In some instances, materials respectively forming one or more portions of the garment 100 such as the body 102, the leg portions 110*a*, 110*b*, the pouch 114, the gusset 118, the waistband 108, and/or other portions of the garment 100 may be separate and distinct from one another, and may be coupled via seams, adhesion, bonding, tape, and the like. Such an approach may provide the designer with greater flexibility in selection of the respective materials for the body 102 (e.g., the front lower torso portion 116*a* and the rear lower torso portion 116*b*), the leg portions 110*a*, 110*b*, the pouch 114, the gusset 118, and the waistband 108, with respect to appearance, feel, weight, breathability, elongation, stretch characteristics, and cost. Alternatively, material(s) forming one or more of the body 102 (e.g., the front lower torso portion 116*a* and the rear lower torso portion 116*b*), the leg portions 110*a*, 110*b*, the pouch 114, and the gusset 118 may be continuous with material(s) forming the waistband 108, such that a garment with a substantially unitary construction is provided.

In some instances, one or more seams of the garment 100 (e.g., the pouch seams 124*a*, 124*b*) may be provided in the form of a mock safety stitch created with a 12-gauge machine. Additionally, the pouch seams 124*a*, 124*b* and/or other seams of the garment 100 may be imparted with moisture management properties. For example, in some instances, the pouch seams 124*a*, 124*b* may utilize a needle thread and a looper thread created from any natural, synthetic, or a natural-synthetic blend material. For example, the needle thread may be provided in the form of a textured, lubricated polyester thread (e.g., T18 Txt Poly thread). In certain instances, the lubricated, polyester thread may be created via an application of a lubricant coating (e.g., a silicone coating, a wax coating, a combination silicone and wax coating), a heat treatment, lubricant impregnation, and the like. The looper thread may be provided in the form of a textured polyester thread (e.g., a T18 Txt Poly thread) imparted with an anti-moisture wicking properties. In certain instances, the looper thread may be imparted with anti-moisture wicking properties via a hydrophobic coating, fiber modification, specialized dyes or finishes, and the like. Alternatively, the seams of the garment 100, including the pouch seams 124*a*, 124*b*, may be provided in any suitable form and may be formed from threads including any suitable materials and imparted with other beneficial properties.

The garment 100 may include any suitable natural, synthetic, or semi-synthetic materials or fabrics including blends or combinations of multiple materials or fabrics. In some instances, the body 102 and/or other portions of the garment 100 may be formed from a number of different materials and fabrics, such as elastomeric or stretch knitted fabric. Such fabrics can be made by varying combinations of cotton, polyester, nylon, spandex, viscose, modal, lyocell, and/or rayon fiber yarns, for example, to provide softness, comfort, and desired stretch properties. The fabrics can be knit in a variety of knit types, such as jersey, rib, mesh, and/or other knit textures and structures.

For example, the body 102 (or other portions of the garment 100) may be at least partially formed from a fabric comprising an elastic material such as spandex in an amount of at least about 1% (or at least 1% elastic material), although the body 102 may be at least partially formed from a fabric comprising somewhat less elastic material than the above amount. For example, the body 102 may be at least partially formed from fabric including at least 5% elastic material to provide flexibility to the fabric and comfort to the wearer. In some implementations, the fabric is a knit fabric having a mechanical stretch to provide a factor of stretchability to the fabric. Mechanical stretch can be defined as a knitting structure of a fabric that creates extra give through the gauge of the knitting, through texture (e.g., a rib structure), or both. For example, a fabric knit with a fine rib pattern can provide mechanical stretch to the fabric and thus to the garment 100 or to the wearer.

In some instances, one or more portions of the garment 100 (e.g., the body 102, the waistband 108, the leg portions 110*a*, 110*b*, the gusset 118, the rear panel 126, and/or other portions of the garment 100) may be composed of a fabric or material that includes at least one of cotton, polyester, and an elastic material (e.g., spandex, silicone, neoprene, and the like), although the garment 100 may also include other materials. As one non-limiting example, one or more portions of the garment 100 may include a fabric or material that includes about 20% to about 75% cotton, about 20% to about 75% polyester, and about 0.1% to about 10% elastic material (e.g., spandex). Alternatively, one or more portions of the garment 100 may include a fabric or material that includes 20% to 75% cotton, 20% to 75% polyester, and 0.1% to 10% elastic material (e.g., spandex). As a second non-limiting example, one or more portions of the garment 100 may include a fabric or material that includes about 35% to about 65% cotton, about 25% to about 45% polyester, and about 1% to about 7% elastic material (e.g., spandex). Alternatively, one or more portions of the garment 100 may include a fabric or material that includes 35% to 65% cotton, 25% to 45% polyester, and 1% to 7% elastic material (e.g., spandex). As a third non-limiting example, one or more portions of the garment 100 may include a fabric or material that includes about 50% to about 98% polyester and about 0.1% to about 15% elastic material (e.g., spandex), but may not include cotton. Alternatively, one or more portions of the garment 100 may include a fabric or material that includes 50% to 98% polyester and 0.1% to 15% elastic material (e.g., spandex), but may not include cotton. However, in other instances, the fabrics or materials forming the portions of the garment 100 may be formed from amounts of cotton, polyester, elastic material, and/or other materials that are somewhat greater than or less than the values above.

In some instances, one or more portions of the garment 100 (e.g., the body 102, the waistband 108, the leg portions 110*a*, 110*b*, the gusset 118, the rear panel 126, and/or other portions of the garment 100) may be composed of a fabric or material that includes at least about 20% cotton. For example, one or more portions of the garment 100 may include at least about 20% cotton, or at least about 25% cotton, or at least about 30% cotton, or at least about 35% cotton, or at least about 40% cotton, or at least about 45% cotton, or at least about 50% cotton, or at least about 55% cotton, or at least about 60% cotton, or at least about 65% cotton, or at least about 70% cotton, or at least about 75% cotton, or at least about 80% cotton, or at least about 85% cotton, or at least about 90% cotton, or at least about 95% cotton, or no more than about 100% cotton. Alternatively, one or more portions of the garment 100 may be composed of a fabric or material that includes at least 20% cotton. For example, one or more portions of the garment 100 may include at least 20% cotton, or at least 25% cotton, or at least 30% cotton, or at least 35% cotton, or at least 40% cotton, or at least 45% cotton, or at least 50% cotton, or at least 55% cotton, or at least 60% cotton, or at least 65% cotton, or at least 70% cotton, or at least 75% cotton, or at least 80% cotton, or at least 85% cotton, or at least 90% cotton, or at least 95% cotton, or no more than 100% cotton. However, in other instances, one or more portions of the garment may include a fabric or material that has somewhat less cotton than the values listed above.

In some instances, one or more portions of the garment 100 (e.g., the body 102, the waistband 108, the leg portions 110*a*, 110*b*, the gusset 118, the rear panel 126, and/or other portions of the garment 100) may be composed of a fabric or material that includes at least about 20% polyester. For example, one or more portions of the garment 100 may include at least about 20% polyester, or at least about 25% polyester, or at least about 30% polyester, or at least about 35% polyester, or at least about 40% polyester, or at least about 45% polyester, or at least about 50% polyester, or at least about 55% polyester, or at least about 60% polyester, or at least about 65% polyester, or at least about 70% polyester, or at least about 75% polyester, or at least 80% polyester, or at least about 85% polyester, or at least about 90% polyester, or at least about 95% polyester, or no more than about 100% polyester. Alternatively, one or more portions of the garment 100 may be composed of a fabric or material that includes at least 20% polyester. For example, one or more portions of the garment 100 may include at least 20% polyester, or at least 25% polyester, or at least 30% polyester, or at least 35% polyester, or at least 40% polyester, or at least 45% polyester, or at least 50% polyester, or at least 55% polyester, or at least 60% polyester, or at least 65% polyester, or at least 70% polyester, or at least 75% polyester, or at least 80% polyester, or at least 85% polyester, or at least 90% polyester, or at least 95% polyester, or no more than 100% polyester. However, in other instances, one or more portions of the garment 100 may include a fabric or material that has somewhat less polyester than the values listed above.

In some instances, one or more portions of the garment 100 (e.g., the body 102, the waistband 108, the leg portions 110*a*, 110*b*, the gusset 118, the rear panel 126, and/or other portions of the garment 100) may be composed of a fabric or material that includes up to about 15% of an elastic material such as spandex, silicone, neoprene, and the like. For example, one or more portions of the garment 100 may include up to about 1% elastic material, or up to about 2% elastic material, or up to about 3% elastic material, or up to about 4% elastic material, or up to about 5% elastic material, or up to about 6% elastic material, or up to about 7% elastic material, or up to about 8% elastic material, or up to about 9% elastic material, or up to about 10% elastic material, or up to about 11% elastic material, or up to about 12% elastic material, or up to about 13% elastic material, or up to about 14% elastic material, or up to about 15% elastic material. Alternatively, one or more portions of the garment 100 may be composed of a fabric or material that includes up to 15% elastic material. For example, one or more portions of the garment 100 may include up to 1% elastic material, or up to 2% elastic material, or up to 3% elastic material, or up to 4% elastic material, or up to 5% elastic material, or up to 6% elastic material, or up to 7% elastic material, or up to 8% elastic material, or up to 9% elastic material, or up to 10% elastic material, or up to 11% elastic material, or up to 12% elastic material, or up to 13% elastic material, or up to 14% elastic material, or up to 15% elastic material. However, in other instances, one or more portions of the garment 100 may include a fabric or material that comprises somewhat more elastic material than the values listed above.

Additionally, in some instances, one or more portions of the garment 100 (e.g., the body 102, the leg portions 110*a*, 110*b*, the pouch 114, the gusset 118, the waistband 108, and/or other portions of the garment 100) may be at least partially composed of a fabric or material imparted with temperature regulation, moisture wicking, and/or odor control properties. For example, the fabric may be mechanically constructed to facilitate the movement of moisture, vapor, or liquid through the fabric. In some instances, one or more portions of the garment 100 may have topical, chemical, and/or other treatments applied thereto in order to impart said portions of the garment 100 with properties such as moisture wicking, vapor transport, odor control, and/or other beneficial properties. Additionally, or alternatively, the fabric may be treated or impregnated with antimicrobial substances (e.g., silver) to impart the fabric with odor control properties. In some instances, one or more of the body 102, the leg portions 110*a*, 110*b*, the front panel 121 or pouch 114, the gusset 118, and the waistband 108 may be composed of different fabrics that are imparted with different properties, where the fabrics individually and/or collectively provide the benefits of moisture management and in-wear comfort.

Figure 7:
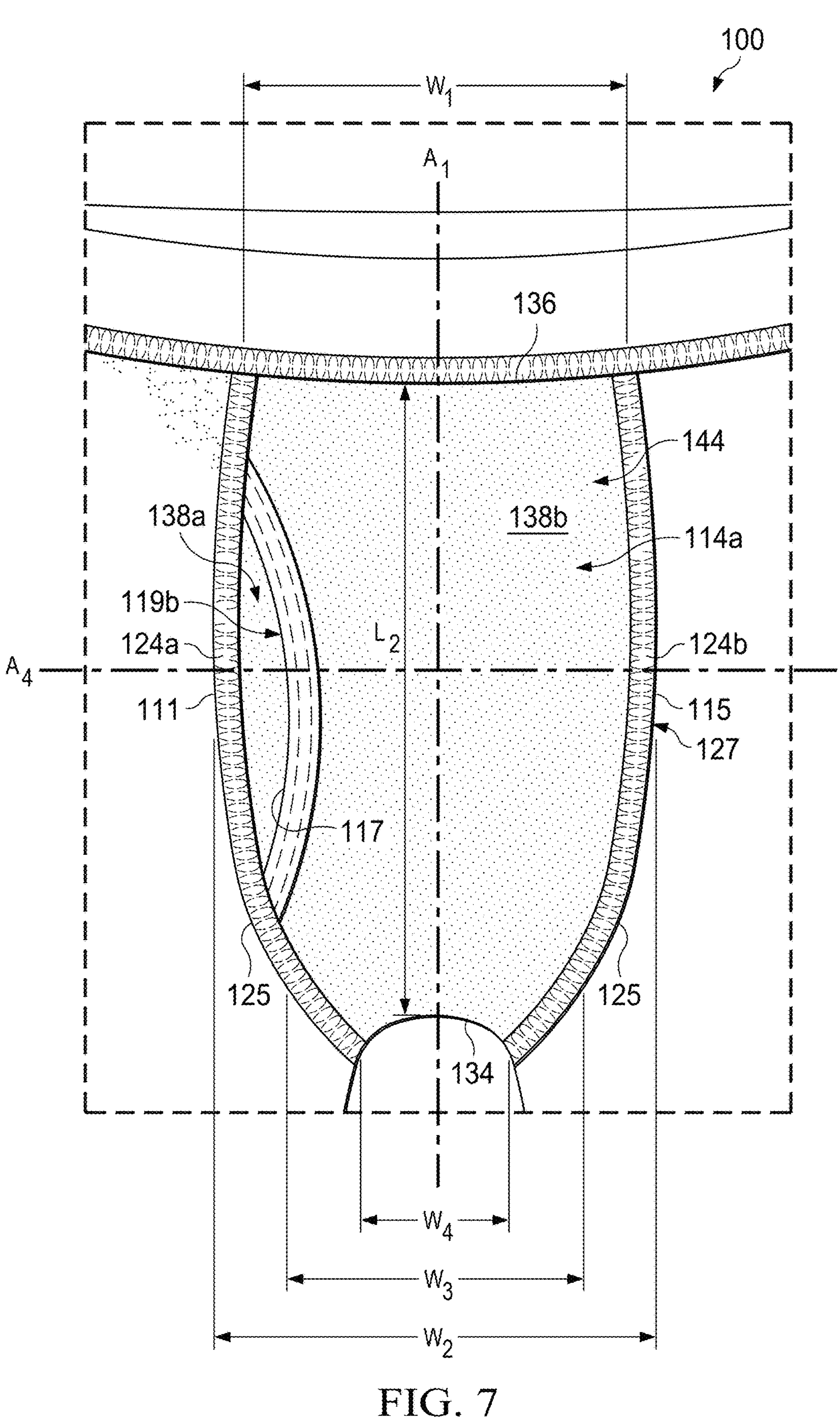
FIG. 7 is an enlarged, elevational view of an outward-facing surface of a pouch of the moisture management garment of FIG. 1, the enlarged view created from the section 7 of FIG. 1 constructed according to the teachings herein.

Turning to FIGS. 7 and 8, the pouch 114 (or one or more portions or layers thereof) may be configured to absorb moisture, adsorb moisture, wick moisture, transport moisture away from a wearer's skin, and/or inhibit moisture from contacting or staining the outward-facing surface of the garment 100. Additionally, the pouch 114 may be designed to improve in-wear comfort, for example, by reducing the thickness and/or the footprint or surface area of the pouch 114 (e.g., as compared to undergarment-like diaper or incontinence products). Further, the pouch 114 may include multiple layers, and, in some instances, the layers of the pouch 114 may have substantially the same dimensions (e.g., length and width) and may be referred to as "coextensive." Alternatively, one or more of the layers may be longer and/or wider than the other layer(s) (i.e., the dimensions of at least one layer of the one or more layers may be different from the other layers of the one or more layers) or may differ from the other layer(s) in one or more aspects. For example, the first panel 138*a* and the second panel 138*b* may be substantially coextensive but may differ somewhat in shape and/or size (e.g., due to the at least partially decoupled left edge of the second panel 138*b*).

Referring first to FIG. 7, the pouch 114 may include multiple distinct panels or layers of fabric or material. For example, the pouch 114 may be provided in the form of the first panel 138*a* and the second panel 138*b* and, in some instances, the first panel 138*a* and the second panel 138*b* may each include one or more layers and/or sublayers of fabric or material. However, in other instances, the pouch 114 may consist of a single panel or layer of fabric or may include more than two panels or layers of fabric.

In some instances, the pouch 114 may be imparted with a substantially V-shaped construction including rounded stems 125 that terminate at or proximate to the pouch first end 134. However, in other instances, the pouch 114 may be imparted with other shapes or structures. In some instances, a width of the pouch 114 may vary (e.g., taper or fluctuate) along at least a portion of the pouch length $L_2$ (see FIG. 3). For example, a midpoint 127 of the pouch length $L_2$ of the pouch 114 may be positioned along the pouch length $L_2$ between the pouch first end 134 and the pouch second end 136. In some instances, the midpoint 127 may be located approximately halfway between the pouch first and second ends 134, 136; however, in other instances, the midpoint 127 may be positioned somewhat closer to either the pouch first end 134 or the pouch second end 136. In certain instances, the midpoint 127 may correspond to a maximum or a local maximum width of the pouch 114, and the width of the pouch 114 may taper (e.g., decrease) between the midpoint 127 and the pouch first end 134 and between the midpoint 127 and the pouch second end 136.

For example, the pouch 114 may be defined by a first width $W_1$ positioned at or proximate to the pouch second end 136 and a second width $W_2$ positioned at or proximate to the midpoint 127. The second width $W_2$ may be greater than the first width $W_1$. For example, the second width $W_2$ may correspond to a maximum width of the pouch 114. In such instances, the width of the pouch 114 may increase continuously along the pouch length $L_2$ between the first width $W_1$ and the second width $W_2$. Alternatively, the width of the pouch 114 may increase discontinuously along the pouch length $L_2$ between the first width $W_1$ and the second width $W_2$ (e.g., a rate of change of the width of the pouch 114 may vary). However, in other instances, the first and second widths $W_1$, $W_2$ may be substantially the same and the width of the pouch 114 between the midpoint 127 and the pouch second end 136 may be substantially constant, or the first width $W_1$ may be somewhat greater than the second width $W_2$. In further instances, the pouch 114 may be substantially rectangular in shape, and the width of the pouch 114 may be substantially constant along the entirety (or the majority) of the pouch length $L_2$.

The pouch 114 may also be defined by a third width $W_3$ positioned between the midpoint 127 and the pouch first end 134. In some instances, the third width $W_3$ may be less than the second width $W_2$. For example, in some instances, the third width $W_3$ may be substantially equal to the first width $W_1$, while in other instances, the third width $W_3$ may be greater than or less than the first width $W_1$. In addition, the width of the pouch 114 may vary along the pouch length $L_2$ between the second width $W_2$ and the third width $W_3$. For example, the width of the pouch 114 may decrease continuously or discontinuously along the pouch length $L_2$ between the second width $W_2$ and the third width $W_3$ (e.g., a rate of change of the width of the pouch 114 between the second width $W_2$ and the third width $W_3$ may be substantially constant or may vary).

The pouch 114 may further be defined by a fourth width $W_4$ positioned between the third width $W_3$ and the pouch first end 134. The fourth width $W_4$ may be less than the first width $W_1$, the second width $W_2$, and/or the third width $W_3$. Alternatively, the fourth width $W_4$ may be substantially equal to the first width $W_1$, the second width $W_2$, and/or the third width $W_3$. In other instances, the fourth width $W_4$ may be greater than the first width $W_1$, the second width $W_2$, and/or the third width $W_3$. In addition, the width of the pouch 114 may vary along the pouch length $L_2$ between the third width $W_3$ and the fourth width $W_4$. For example, the width of the pouch 114 may decrease continuously or discontinuously along the pouch length $L_2$ between the third width $W_3$ and the fourth width $W_4$ (e.g., a rate of change of the width of the pouch 114 between the third width $W_3$ and the fourth width $W_4$ may be substantially constant or may vary).

In further instances, the width of the pouch 114 may be substantially constant along the pouch length $L_2$ such that the first, second, third, and fourth widths $W_1$, $W_2$, $W_3$, $W_4$ are substantially equal to each other, or the pouch 114 may be imparted with any other suitable shape or structure.

While FIG. 7 depicts an outward-facing surface 144 of the garment 100 or pouch 114 (e.g., a surface that is visible when the garment 100 is worn in the intended configuration), FIG. 8 depicts an associated wearer-facing surface 146 of the garment 100 or pouch 114. The outward-facing surface 144 may be substantially flat and untextured whereas, in some instances, the wearer-facing surface 146 may be imparted with a texture, material, surface treatment, or other characteristic designed to facilitate moisture transport and/or removal. For example, the wearer-facing surface 146 may in some instances include a plurality of pores 151 or other features designed to facilitate absorbance, adsorbance, and/or transport of moisture, as described in further detail below with reference to FIG. 10A.

Figure 9A:
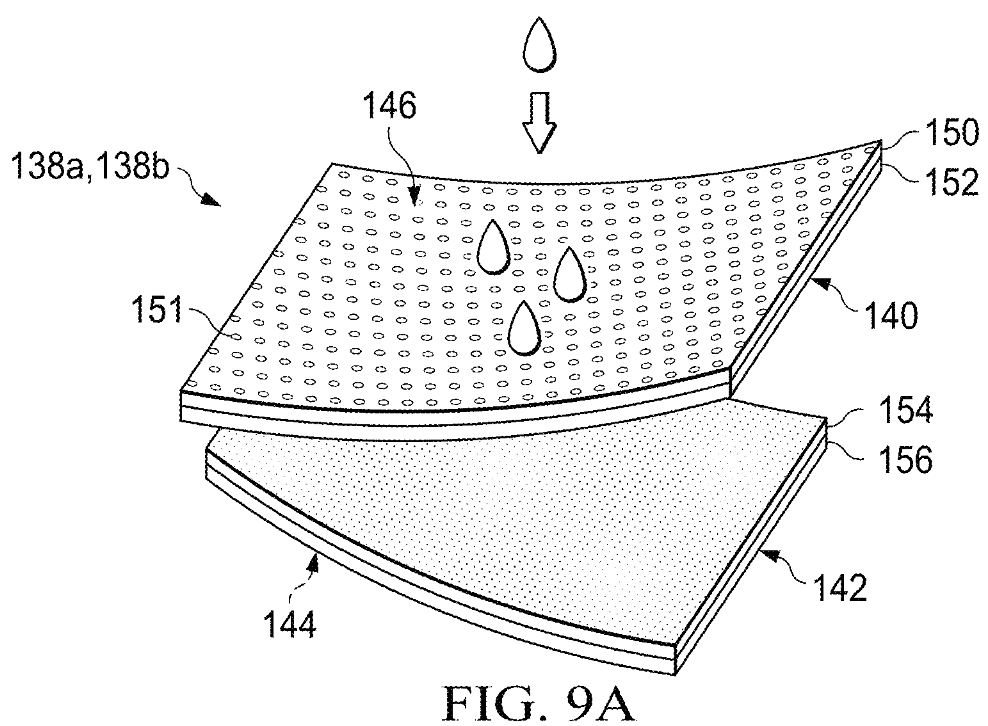
FIG. 9A is a schematic, exploded view of fabric layers provided in an example panel of a pouch as depicted in any of FIGS. 1-8.
Figure 9B:
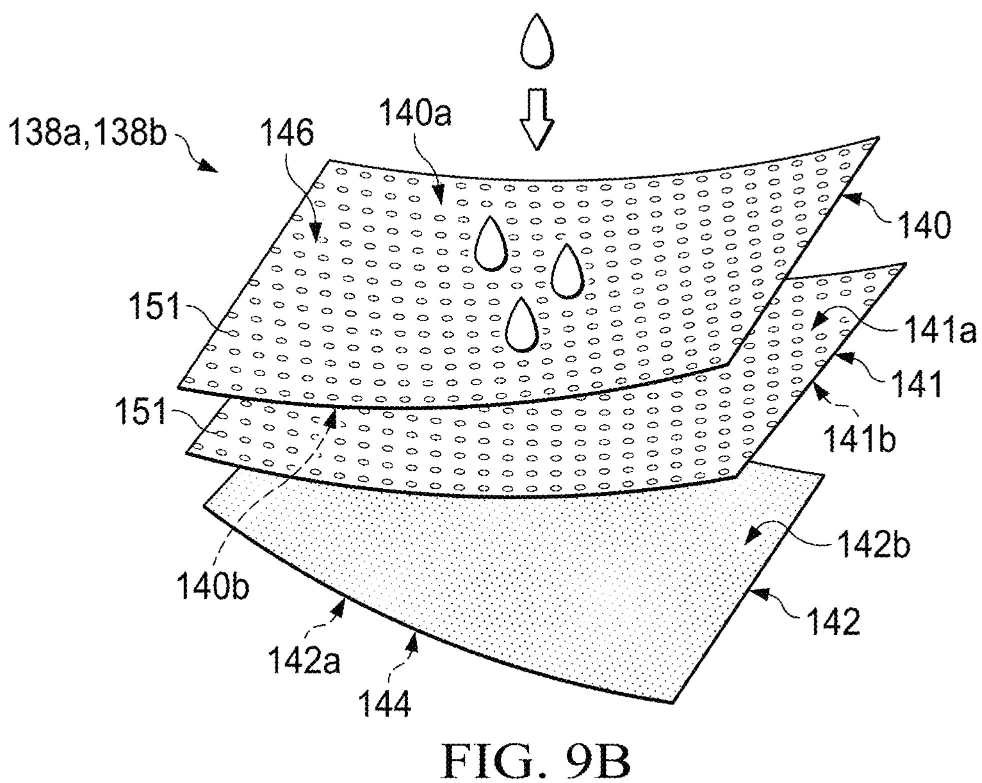
FIG. 9B is another schematic, exploded view of fabric layers provided in another example panel of a pouch as depicted in any of FIGS. 1-8.

Turning to FIGS. 9A and 9B, the pouch 114 may be provided in the form of a "pouch assembly" including one or more layers of fabric or material (e.g., one or more distinct layers of fabric or material, one or more sublayers of fabric or material that constitute one or more layers of fabric or material, etc.). Additionally, or alternatively, the pouch 114 may be provided as a "moisture-absorbent zone" or "moisture-adsorbent zone" that includes at least two distinct layers of fabric or material (e.g., at least two layers, at least three layers, at least four layers, etc.), such as at least one moisture-absorbent or moisture-adsorbent fabric layer and at least one moisture-resistant, water-resistant, moisture-impermeable, or water-impermeable fabric layer. In some such instances, the pouch 114 (or the fabric panels comprising the pouch 114) may include a first, moisture-absorbent layer, a second, water-resistant layer, and any number of additional fabric layers positioned between or on either side of the first and second layers. The additional fabric layers may be adapted to absorb, adsorb, wick, or transport moisture away from the wearer's body.

The pouch assembly or pouch 114 may include the first panel 138*a*, the second panel 138*b* (e.g., the pouch 114 may consist of the first panel 138*a* and the second panel 138*b*). In addition, the description below accompanying FIGS. 9A-13 may apply equally to the first panel 138*a* and/or the second panel 138*b*. For example, the first panel 138*a* and the second panel 138*b* may in some instances be provided in a substantially similar form or may be substantially similar to one another in one or more aspects. However, in certain cases, the first panel 138*a* and the second panel 138*b* may be provided in different forms. For example, the first panel 138*a* may be provided in the form discussed with reference to FIG. 12 while the second panel 138*b* may be provided in the form discussed with reference to FIG. 11.

In some instances, the first panel 138*a* and/or the second panel 138*b* may be provided in the form of a moisture-absorbent or moisture-adsorbent layer, or may be provided in the form of a moisture-resistant, water-resistant, urine-resistant, moisture-impermeable, or water-impermeable layer Additionally, the pouch 114 (e.g., the first panel 138*a* and/or the second panel 138*b*) may be adapted to facilitate absorbing moisture, adsorbing moisture, or wicking or transporting moisture away from the wearer's body.

In some instances, the first panel 138*a* and/or the second panel 138*b* may each be provided in the form of a single layer of fabric or material. However, in other instances, one or both of the first panel 138*a* and the second panel 138*b* may include two or more layers of fabric or material that together constitute the first panel 138*a* or the second panel 138*b*, as described in further detail below with reference to FIG. 9A. For example, the first panel 138*a* and/or the second panel 138*b* may include at least two layers, at least three layers, at least four layers, or any other number of layers of fabric or material.

It is to be understood that, in some cases, any moisture-resistant, water-resistant, moisture-impermeable, or water-impermeable layer provided in the pouch 114 may allow for permeation of water vapor or other gases through the layer, thereby allowing for the dispersion of moisture out of the garment 100 while also partially, substantially completely, or completely preventing the movement of liquids through the layer. In other instances, any moisture-resistant or water-resistant layers provided in the pouch 114 may facilitate the movement of liquids across and/or through the layer, thereby spreading the liquids over a larger surface area and/or volume, which in turn may facilitate the evaporation of the liquids and help prevent the wearer from perceiving the layer as being "wet."

The droplets and arrow in FIGS. 9A and 9B schematically represent how moisture may be introduced to the pouch 114 (e.g., introduced to the first panel 138*a*, the second panel 138*b*, and/or other portions of the pouch 114) when the garment 100 is worn in the intended configuration. For example, as the wearer of the garment 100 sweats, moisture may move away from the wearer's body and contact the first pouch layer 140 before being provided to the second pouch layer 142 and/or other fabric layers provided in the pouch 114. However, in other implementations, the fabric layers of the pouch 114, or the fabric layers of the first panel 138*a* and/or the second panel 138*b*, may be arranged in a different configuration than described herein.

The composition of the fabric layers of the pouch 114, the arrangement of the fabric layers in the construction of the pouch 114, the position of the pouch 114 with respect to the garment 100, and/or other aspects of the pouch 114 may be selected to optimize moisture management. Additionally, or alternatively, the composition of the fabric layers of the pouch 114, the arrangement of the fabric layers in the construction of the pouch 114, and other aspects of the pouch 114 may be selected to optimize in-wear comfort. For example, the use of fabric layers comprising polyester, nylon, or similar synthetic materials may allow for the construction of a pouch 114 that is thinner and lighter in weight than, for example, undergarment-like diaper or incontinence products.

The first panel 138*a*, the second panel 138*b*, and/or other portions of the pouch 114 may be provided in the form of a fabric and/or materials selected to improve moisture absorption, moisture-adsorption, moisture wicking, moisture transport, and/or other moisture management-related properties, such as odor control, antibacterial properties, or other properties. For example, the inclusion of certain fabrics and materials, such as cotton, bamboo, wool, linen, hemp, silver, and the like in the pouch 114 may impart the pouch 114 with increased odor control and/or antibacterial properties.

In addition, one or more portions of the pouch 114 (e.g., the first panel 138*a*, the second panel 138*b*, and/or other portions of the pouch 114) may include a fabric comprising hydrophobic yarns or materials, hydrophilic yarns or materials, or a combination thereof. Generally, hydrophilic yarns and fibers, such as cotton yarns and fibers, absorb water, while hydrophobic yarns and fibers, such as polyester yarns and fibers, repel water. The yarns and fibers of the pouch 114 may also be chemically treated or modified (e.g., laminated or treated with a durable, water-resistant agent) to increase or decrease hydrophobicity or hydrophilicity of the fibers and/or to provide the pouch 114 with other moisture management benefits, such as odor control (e.g., via antibacterial agents, such as silver). One or more portions of the pouch 114 or of the first panel 138*a* and/or the second panel 138*b* may include a fabric that has one or more laminated surfaces (e.g., a hydrophobic film such as a thermoplastic film). One or more portions of the pouch 114 may include a fabric that has been treated or impregnated with an agent that provides odor control, stain release or repellency, moisture repellency, hygiene, wicking, softness, and/or moisture absorbency. In some instances, the agent may be selected to increase a wicking distance and/or wicking rate of the pouch 114 (or of a portion thereof). The agent may generally be provided in the form of a gel, a liquid, a powder, or any other form that may be applied to the fabric by any number of well-known methods such as padding, exhaust, application of heat, application of pressure, and the like.

FIG. 9A depicts a first example construction of the first panel 138*a* and/or the second panel 138*b*. As shown, in some instances, the first panel 138*a* and/or the second panel 138*b* may be provided in the form of two layers including a first fabric layer or a first pouch layer 140 and a second fabric layer or a second pouch layer 142 positioned adjacent to the first pouch layer 140. The first pouch layer 140 may be provided in the form of a wearer-facing, moisture-absorbent or moisture-adsorbent layer. In other words, the first pouch layer 140 may be arranged to be adjacent to or in contact with the body of a wearer when the garment 100 is worn in its intended configuration and may be designed to facilitate the wicking or transport of moisture away from the wearer's body. The second pouch layer 142 may be arranged opposite the wearer's body with respect to the first pouch layer 140 and may be provided in the form of a water-resistant or moisture-resistant layer. For example, the second pouch layer 142 may be formed from a water-resistant or at least partially hydrophobic material, may be laminated with a hydrophobic film, and/or may be treated with a hydrophobic agent or substance such that the second pouch layer 142 is imparted with hydrophobic properties.

The first and second pouch layers 140, 142 may each be provided in the form of a single layer of fabric or may each include two or more distinct or independent sublayers of fabric. For example, the first pouch layer 140 may include a first wearer-facing sublayer 150 and a first outward-facing sublayer 152, and the second pouch layer 142 may include a second wearer-facing sublayer 154 and a second outward-facing sublayer 156. In some instances, the first wearer-facing sublayer 150 constitutes the technical face of the first pouch layer 140 and the first outward-facing sublayer 152 constitutes the technical back of the first pouch layer 140 (e.g., the first wearer-facing sublayer 150 and the first outward-facing sublayer 152 may be provided as a composite layer of fabric or material forming the first pouch layer 140), and the second wearer-facing sublayer 154 may constitute the technical back of the second pouch layer 142 and the second outward-facing sublayer 156 may constitute the technical face of the second pouch layer 142 (e.g., the second wearer-facing sublayer 154 and the second outward-facing sublayer 156 may be provided as a composite layer of fabric or material forming the second pouch layer 142). However, in other instances, the sublayers 150, 152, 154, 156 may each be provided in the form of distinct or independent layers of fabric or material, each of which may include its own technical face and technical back.

In some instances, the first and second pouch layers 140, 142 may be arranged in an opposite orientation relative to one another such that the first outward-facing sublayer 152 (e.g., the technical back of the first pouch layer 140) is adjacent to or in contact with the second wearer-facing sublayer 154 (e.g., the technical back of the second pouch layer 142). In such instances, the first wearer-facing sublayer 150 of the first pouch layer 140 may constitute the wearer-facing surface 146 of the pouch 114 (see FIG. 7), and the second outward-facing sublayer 156 of the second pouch layer 142 may constitute the outward-facing surface 144 of the pouch 114 (see FIG. 8). In other instances, the first pouch layer 140, the second pouch layer 142, and/or additional layers or portions of the pouch 114 may be arranged in any suitable configuration and any surface of any layer of the pouch 114 may be provided as the outward-facing surface 144 or the wearer-facing surface 146.

In some instances, the second pouch layer 142 may comprise a jersey knit fabric constructed from cotton yarn, where the cotton yarn comprises up to about 100% cotton fibers (or up to 100% cotton fibers). In some cases, the second pouch layer 142 may comprise up to about 100% synthetic fibers or fabrics. In other cases, the second pouch layer 142 may comprise a blend of synthetic fabrics, e.g., a polyester-spandex blend. In further cases, the second pouch layer 142 may comprise a blend of natural and synthetic fabrics, e.g., a blend of cotton, polyester, and spandex. In other instances, the second pouch layer 142 may also comprise a rib, interlock, and/or jacquard fabric composed of a natural, synthetic, or semi-synthetic fabric (including blends thereof). In some instances, the second pouch layer 142 has substantially the same composition as that of other portions of the garment 100 (e.g., the body 102).

FIG. 9B depicts a second construction of the first panel 138*a* and/or the second panel 138*b* including at least one additional layer of fabric or material. For clarity, the sublayers of the first and second pouch layers 140, 142 (and/or the sublayers of a third fabric layer or a third pouch layer 141) are not depicted in FIG. 9B. As shown, in some instances, the first panel 138*a* and/or the second panel 138*b* may include the first pouch layer 140, the second pouch layer 142, and a third pouch layer 141 positioned between the first and second pouch layers 140, 142. In some instances, the third pouch layer 141 may be substantially similar to the first pouch layer 140 and may be configured to facilitate the wicking or transport of moisture away from the wearer's body. However, in other instances, the third pouch layer 141 may be substantially similar to the second pouch layer 142 or may be provided in a different form as compared to the first and second pouch layers 140, 142. As shown in FIG. 9B, the first, second, and third pouch layers 140, 142, 141 may consist of a single layer of fabric or material; however, in other instances, the first, second, and/or third pouch layers 140, 142, 141 may include two or more sublayers as described above with respect to FIG. 9A.

In some instances in which the first, second, and third pouch layers 140, 142, 141 are provided in the form of a single layer of fabric or material, each layer of the pouch 114 may include a technical face and a technical back. For example, the first pouch layer 140 may include a technical face 140*a* and a technical back 140*b*, the second pouch layer 142 may include a technical face 142*a* and a technical back 142*b*, and the third pouch layer 141 may include a technical face 141*a* and a technical back 141*b*. In some instances, the first and third pouch layers 140, 141 may be provided in a first orientation, and the second pouch layer 142 may be provided in a second orientation opposite to the first orientation. For example, the technical face 140*a* of the first pouch layer 140 and the technical face 141*a* of the third pouch layer 141 may face in a first direction (e.g., in a direction of a wearer when the garment 100 is worn in its intended configuration), whereas the technical face 142*a* of the second pouch layer 142 may face in a second direction (e.g., in an outward-facing direction relative to a wearer when the garment 100 is worn in its intended configuration). In other words, the technical face 140*a* of the first pouch layer 140 may be adjacent to the technical face 141*a* of the third pouch layer 141, and the technical back 141*b* of the third pouch layer 141 may be adjacent to the technical back 142*b* of the second pouch layer 142. However, in other instances, the first pouch layer 140, the second pouch layer 142, the third pouch layer 141, and/or other layers or portions of the pouch 114 may be provided in any suitable orientation relative to one another.

In addition to the examples depicted in FIGS. 9A and 9B, the first panel 138*a* and/or the second panel 138*b* (e.g., the first panel 138*a* and/or second panel 138*b* of the first pouch 114*a*, the second pouch 114*b*, and/or any other pouch 114 described herein) may be provided in other forms not specifically described herein. For example, one or both of the first panel 138*a* and the second panel 138*b* may include any number of fabric layers in addition to or in lieu of the first, second, and third pouch layers 140, 142, 141 described above, and the layers of the of the first panel 138*a* and/or the second panel 138*b* may be provided in any suitable form (e.g., formed from any suitable material). For example, the first, second, and/or third pouch layers 140, 142, 141 may each comprise nylon, wool, bamboo, modal fabrics, mesh, and/or any other natural or synthetic fiber or material.

Figure 10A:
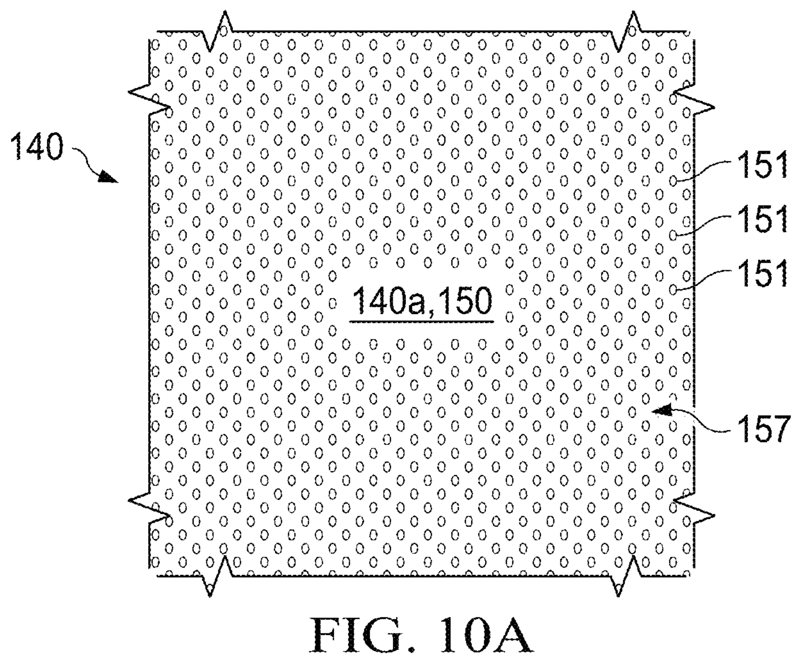
FIG. 10A is a close-up, elevational view of a technical face of a portion of a fabric layer of a pouch as depicted in any of FIGS. 1-8.
Figure 10B:
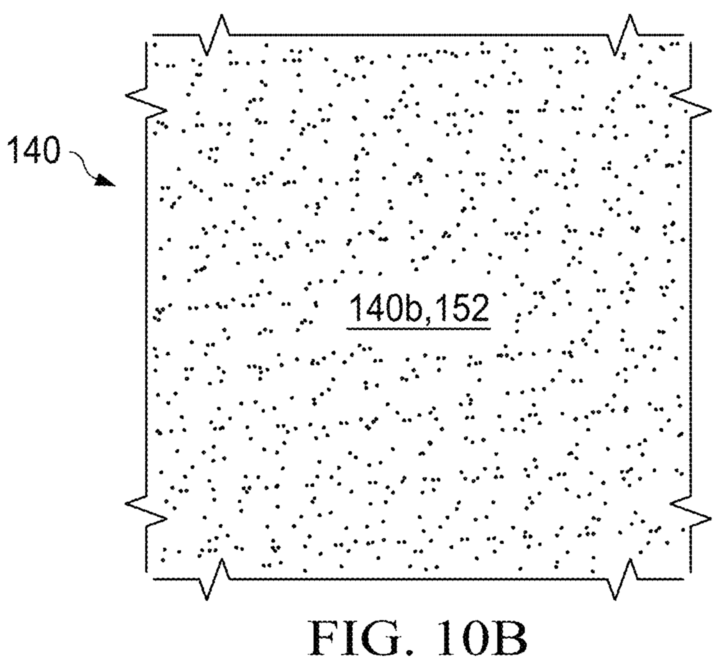
FIG. 10B is a close-up, elevational view of a technical back of a portion of a fabric layer of a pouch as depicted in any of FIGS. 1-8.

FIGS. 10A and 10B depict opposing surfaces of the first pouch layer 140. For example, FIG. 10A depicts a portion of the technical face 140*a* of the first pouch layer 140 (or a portion of the first wearer-facing sublayer 150 as seen from an interior of the garment 100 when the garment 100 is worn in its intended configuration), and FIG. 10B depicts a portion of the technical back 140*b* of the first pouch layer 140 (or a portion of the first outward-facing sublayer 152 as seen from an exterior of the garment 100 when the garment 100 is worn in its intended configuration and the first pouch layer 140 is exposed). The technical face 140*a* of the first pouch layer 140 (or the first wearer-facing sublayer 150) may be imparted with a first texture, and the technical back 140*b* of the first pouch layer 140 (or the first outward-facing sublayer 152) may be imparted with a second texture. In some instances, the first and second textures may be substantially similar; however, in other instances, the first and second textures may be different.

For example, the first texture of the technical face 140*a* of the first pouch layer 140 may include one or more features configured to facilitate absorption, adsorption, and/or transport of moisture such as one or more pores 151. Thus, in some instances, the technical face 140*a* may be provided in the form of an absorbent mesh and/or adsorbent mesh. In some instances, the technical face 140*a* of the first pouch layer 140 may include a plurality of pores 151 positioned thereon in a standardized pattern (e.g., a grid pattern, rows and columns, etc.), although the pores 151 need not be provided in a pattern.

In the example of FIG. 10A, the pores 151 may be substantially circular or ovoid in shape. However, in other instances, the pores may be imparted with other shapes; for example, the pores 151 may be imparted with a triangular shape, polygonal shape, rectangular shape, or other shape. Additionally, the pores 151 may be provided in any suitable size to facilitate moisture management. For example, in some instances, the pores 151 may be provided in the form of nanometer-scale pores 151 (e.g., less than 1 micron in width or diameter) or macroscopic pores 151 (e.g., greater than 1 millimeter in width or diameter), or may be provided in any other suitable size, including sizes between the nanometer and macroscopic scales referred to herein. The pores 151 are not drawn to scale in the figures and may be imparted with any suitable size; for example, the pores 151 may be imperceptible to the human eye.

Furthermore, in certain instances, a porosity (e.g., a number of pores 151 in a given surface area and/or the size of the pores 151) of the technical face 140*a* of the first pouch layer 140 may be adjusted to provide the desired moisture management properties. For example, the porosity of the first texture may be adjusted by modifying one or more characteristics of the pores 151 or other features of the technical face 140*a*. Such an adjustment may include, but is not limited to, adjusting the ratio between the portion of the technical face 140*a* occupied by pores 151 and the remainder of the technical face 140*a*. For example, in some instances, a ratio of a first surface area corresponding to a void space 157 (e.g., a portion of the surface area of the technical face 140*a* that does not contain pores 151) to a second surface area corresponding to the total surface area (or substantially all of the surface area) of the technical face 140*a* may be imparted with a value of up to about 50%. For example, the ratio of the first surface area of the void space 157 to the second surface area of the technical face 140*a* may be imparted with a value of up to about 5%, or up to about 10%, or up to about 15%, or up to about 20%, or up to about 25%, or up to about 30%, or up to about 35%, or up to about 40%, or up to about 45%, or up to about 50%. Alternatively, the ratio of the first surface area of the void space 157 to the second surface area of the technical face 140*a* may be imparted with a value of up to 50%. For example, the ratio of the first surface area of the void space 157 to the second surface area of the technical face 140*a* may be imparted with a value of up to 5%, or up to 10%, or up to 15% or up to 20%, or up to 25%, or up to 30%, or up to 35%, or up to 40%, or up to 45%, or up to 50%. In other instances, the ratio of the first surface area of the void space 157 to the second surface area of the technical face 140*a* may be imparted with a value of at least about 50%. For example, the ratio of the first surface area of the void space 157 to the second surface area of the technical face 140*a* may be imparted with a value of at least about 5%, or at least about 10%, or at least about 15%, or at least about 20%, or at least about 25%, or at least about 30%, or at least about 35%, or at least about 40%, or at least about 45%, or at least about 50%. Alternatively, the ratio of the first surface area of the void space 157 to the second surface area of the technical face 140*a* may be imparted with a value of at least 50%. For example, the ratio of the first surface area of the void space 157 to the second surface area of the technical face 140*a* may be imparted with a value of at least 50%, or at least 55%, or at least 60%, or at least 65%, or at least 70%, or at least 75%, or at least 80%, or at least 85%, or at least 90%, or at least 95%, or at least 100%. However, in other instances, the ratio of the first surface area of the void space 157 to the second surface area of the technical face 140*a* may be imparted with a value that is somewhat less or even greater than the values listed above.

In further instances, the pores 151 may be omitted and the technical face 140*a* of the first pouch layer 140 may include one or more other features configured to facilitate moisture management by absorbing, adsorbing, or transporting moisture. For example, in some instances, the technical face 140*a* may include a mesh structure including interconnected strands or fibers that enable moisture to pass therethrough. In such instances, the size, thickness, geometry, arrangement, and/or other aspects of the strands or fibers of the mesh structure may be modified to provide the desired moisture management properties. In other instances, the technical face 140*a* may include one or more (e.g., a plurality) other features configured to wick, absorb, adsorb, or otherwise transport moisture including, but not limited to, channels, grooves, gradient structures, capillary structures, absorbent coatings, and the like. In certain instances, the technical back 140*b* of the first pouch layer 140 may also include pores, a mesh structure, and/or other aspects designed to help facilitate the movement of moisture from the technical face 140*a* to the technical back 140*b* via capillary action. For example, the technical back 140*b* may include pores (not depicted) of a smaller size than the pores of the technical face 140*a* and/or the technical back 140*b* may be constructed of threads with a different denier than the technical face 140*a*. It is to be understood that the technical face 140*a* and the technical back 140*b* are not limited to the structures or forms explicitly described herein.

Without being bound to a particular theory, it is believed that the difference in the textures and/or features of the technical face 140*a* and the technical back 140*b* of the first and third pouch layers 140, 141 may facilitate the transport of moisture from one surface of the first and third pouch layers 140, 141 to an opposite surface of the first and third pouch layers 140, 141. For example, the technical face 140*a* of the first pouch layer 140 may be designed to draw moisture away from the wearer when the first pouch layer

140 is provided in the pouch 114 and arranged next to the wearer's body. As the wearer perspires, the first pouch layer 140 may transport moisture away from the wearer via capillary action. The moisture may move toward the technical back 140*b* of the first pouch layer 140. After the moisture is provided to the technical back 140*b* of the first pouch layer 140, other layers of the pouch 114 (e.g., the third pouch layer 141, if provided, or the second pouch layer 142) may draw the moisture away from the first pouch layer 140 and thus away from the wearer. Eventually, the moisture may reach the second pouch layer 142, which may be provided as the outermost layer of the pouch 114. The second pouch layer 142 may retain the moisture and/or transport the moisture across surfaces of the second pouch layer 142 and/or throughout a volume of the second pouch layer 142 until the moisture ultimately evaporates and is dispersed from the garment 100.

By contrast, the technical back 140*b* of the first pouch layer 140 may be imparted with the second texture, which may be substantially flat and untextured, as shown in FIG. 10B. In other words, in some instances, the technical back 140*b* of the first pouch layer 140 may not include pores 151 or other features as described above with reference to FIG. 10A. However, in other instances, the technical back 140*b* of the first pouch layer 140 may include pores 151, other features, or may be provided in any other suitable form.

In certain instances, such as when the first panel 138*a* and/or the second panel 138*b* include more than two fabric layers, the third pouch layer 141 may be provided in substantially the same form as the first pouch layer 140 as depicted and described with reference to FIGS. 9A and 9B. In other instances, the first pouch layer 140 and the third pouch layer 141 may be provided in different forms.

Turning to FIGS. 11-14, several potential configurations or constructions of a portion of the pouch 114 are depicted. More particularly, FIGS. 11-14 provide several example layering configurations for the first panel 138*a* and/or the second panel 138*b*. In general, the pouch 114 may include the first pouch layer 140 and the second pouch layer 142. For example, the first and second pouch layers 140, 142 of FIGS. 11-14 may correspond to (and may, in some instances, be substantially similar to) the first panel 138*a* and the second panel 138*b* of the pouch 114, respectively (see, e.g., FIGS. 1 and 3). In some instances, such as in FIG. 11, the pouch 114 may consist of the first and second pouch layers 140, 142. However, in other instances, the pouch 114 may include one or more additional layers such as the third pouch layer 141 positioned between or on either side of the first and second pouch layers 140, 142 (see FIG. 14).

Figure 11:
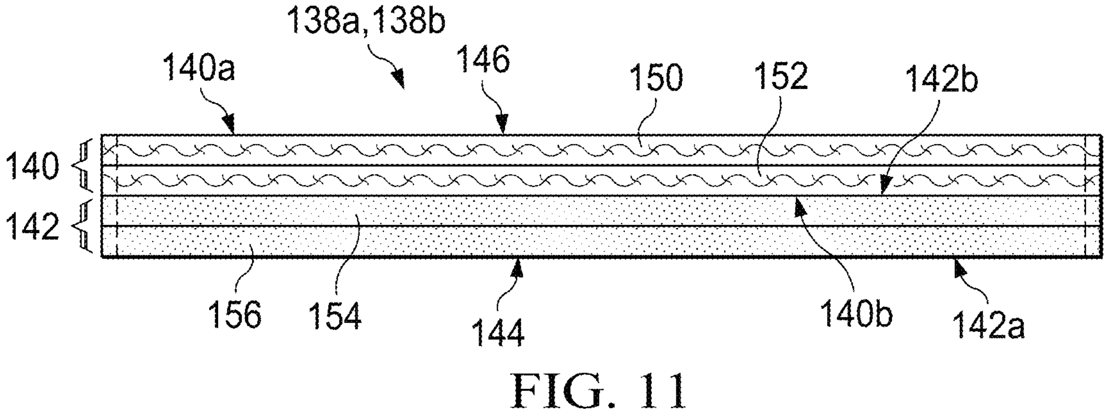
FIG. 11 is a schematic representation of fabric layers of a portion of a panel of an example pouch as depicted in any of FIGS. 1-8.

Referring first to FIG. 11, in some instances, the pouch 114 may be provided in the form of the first pouch layer 140 and the second pouch layer 142, in which the first pouch layer 140 includes the wearer-facing layer (e.g., a wearer-facing surface or sublayer) and the second pouch layer 142 is disposed opposite the wearer's body with respect to the first pouch layer 140. The first and second pouch layers 140, 142 may each include a technical face (e.g., the technical face 140*a*, 142*a*) and a technical back (e.g., technical back 140*b*, 142*b*). Thus, as shown in FIG. 11, the technical face 140*a* of the first pouch layer 140 may constitute the wearer-facing surface 146 (see FIG. 8), the technical face 140*a* of the second pouch layer 142 may constitute the outward-facing surface 144 (see FIG. 7), and the technical back 140*b* of the first pouch layer 140 may be adjacent to (or may be arranged to face) the technical back 142*b* of the second pouch layer 142. In certain instances, one or more additional layers of moisture-absorbent or moisture-adsorbent fabrics and/or one or more additional layers of moisture-resistant or moisture-repellant fabrics may be positioned between or on either side of the first and second pouch layers (see, e.g., FIG. 14).

In some instances, the first and second pouch layers 140, 142 (in addition to additional layers of the pouch 114) may each be provided in the form of a single layer of fabric or material. However, in other instances, each of the first and second pouch layers 140, 142 (in addition to additional layers of the pouch 114) may include two or more distinct sublayers of fabric or material that together constitute the first pouch layer 140 and/or the second pouch layer 142. In the examples depicted in FIGS. 11-14, the first and second pouch layers 140, 142 are each provided in the form of two distinct fabric layers. The first pouch layer 140 may include the first wearer-facing sublayer 150 and the first outward-facing sublayer 152, and the second pouch layer 142 may include the second wearer-facing sublayer 154 and the second outward-facing sublayer 156. However, in other instances, the first and second pouch layers 140, 142 (and/or additional fabric layers of the pouch 114) may include any number of distinct sublayers of fabric or material that may be provided in any suitable form.

The first and second pouch layers 140, 142 (or, alternatively, the first panel 138*a* and/or the second panel 138*b*) may comprise substantially similar materials or different materials. In some instances, the first and second pouch layers 140, 142 may be provided as a natural fabric, a synthetic fabric, a semi-synthetic fabric, and/or combinations thereof. For example, the first pouch layer 140 may comprise polyester, cotton, nylon, spandex, viscose, modal, lyocell, rayon, other materials, or a combination thereof. In some instances, the first pouch layer 140 and/or the second pouch layer 142 may comprise a fabric provided in the form of a double knit semi-jacquard construction comprising a hydrophobic (e.g., 100% polyester 75/72) microfiber filament yarn. As an additional example, the second pouch layer 142 may comprise polyester, cotton, nylon, spandex, viscose, modal, lyocell, rayon, other materials, or a combination thereof. Additionally, in some instances, the first pouch layer 140 and/or the second pouch layer 142 may be provided in a knit, double knit, jersey knit, rib, interlock, and/or jacquard or other suitable construction.

Figure 12:
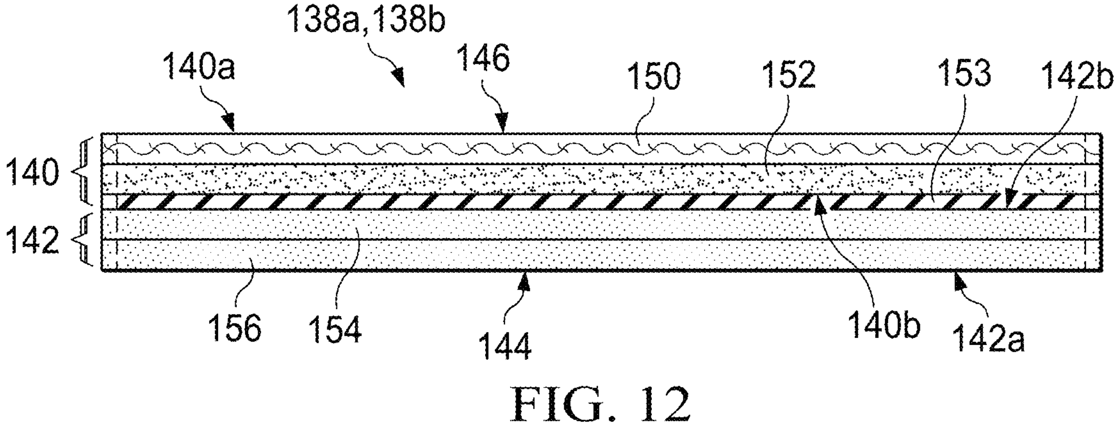
FIG. 12 is a schematic representation of fabric layers of a portion of a panel of another example pouch as depicted in any of FIGS. 1-8.
Figure 13:
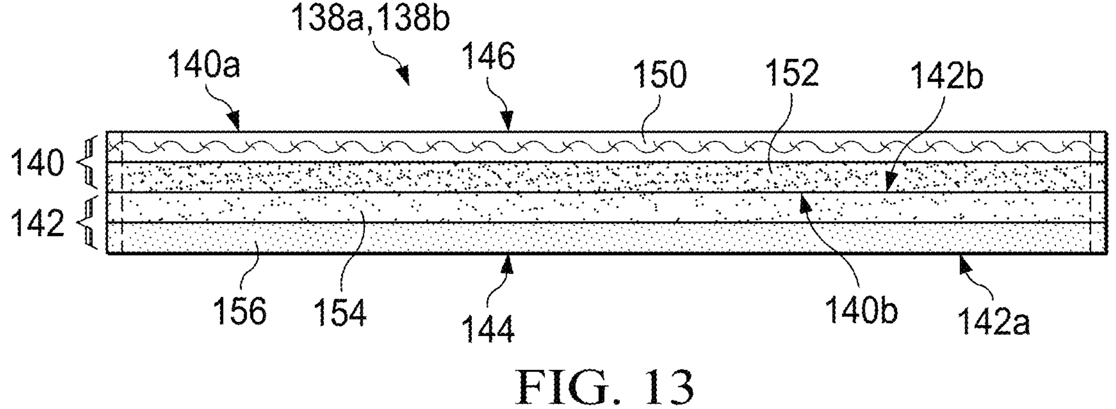
FIG. 13 is a schematic representation of fabric layers of a portion of a panel of a further example pouch as depicted in any of FIGS. 1-8.

Furthermore, the first wearer-facing sublayer 150 and the first outward-facing sublayer 152 of the first pouch layer 140 may be provided in substantially the same form (see, e.g., FIG. 11) or may be provided in different forms (see, e.g., FIGS. 12 and 13). Likewise, the second wearer-facing sublayer 154 and the second outward-facing sublayer 156 of the second pouch layer 142 may be provided in substantially the same form (see, e.g., FIGS. 11, 12, and 14) or may be provided in different forms (see, e.g., FIG. 13). The first pouch layer 140 (e.g., including the first wearer-facing sublayer 150 and/or the first outward-facing sublayer 152) may comprise fabrics or materials having different compositions (e.g., synthetic materials, natural materials, blended materials, chemical treatments, chemical modifications, and the like) and different constructions (e.g., woven fabrics, knitted fabrics, and the like).

The first and second pouch layers 140, 142 may comprise substantially similar materials or different materials. In some instances, the first and second pouch layers 140, 142 may be provided in the form of a natural fabric, a synthetic fabric, a semi-synthetic fabric, and/or combinations thereof. For example, the first pouch layer 140 may comprise polyester, cotton, nylon, spandex, viscose, modal, lyocell, rayon, other materials, or a combination thereof. In some instances, the first pouch layer 140 and/or the second pouch layer 142 may comprise a fabric provided in the form of a double knit semi-jacquard construction comprising a hydrophobic (e.g., 100% polyester 75/72) microfiber filament yarn. As an additional example, the second pouch layer 142 may comprise polyester, cotton, nylon, spandex, viscose, modal, lyocell, rayon, other materials, or a combination thereof. Additionally, in some instances, the first pouch layer 140 and/or the second pouch layer 142 may be provided in a knit, double knit, jersey knit, rib, interlock, and/or jacquard or other suitable construction.

In some instances, at least a portion of the first pouch layer 140 (e.g., the first wearer-facing sublayer 150 and/or the first outward-facing sublayer 152) may be provided in the form of a moisture-absorbent or moisture-adsorbent fabric comprising an elastic material (e.g., a material that is stretchable to some degree such as rubber, latex, silicone, elastane, recycled elastane, organic materials with elastic core, and the like). Thus, the moisture-absorbent or moisture-adsorbent fabric of the first pouch layer 140 may include at least about 0% elastic material to at least about 50% elastic material, or at least about 1% elastic material to at least about 25% elastic material, although the first pouch layer 140 may also be comprised of a percentage of elastic material that is somewhat greater than these values. For example, the moisture-absorbent or moisture-adsorbent fabric of the first pouch layer 140 may include at least about 1% elastic material, or at least about 2% elastic material, or at least about 3% elastic material, or at least about 4% elastic material, or at least about 5% elastic material, or at least about 6% elastic material, or at least about 7% elastic material, or at least about 8% elastic material, or at least about 9% elastic material, or at least about 10% elastic material, or at least about 12% elastic material, or at least about 14% elastic material, or at least about 16% elastic material, or at least about 18% elastic material, or at least about 20% elastic material, or at least about 22% elastic material, or at least about 24% elastic material, or at least about 26% elastic material, or at least about 28% elastic material, or at least about 30% elastic material, or at least about 35% elastic material, or at least about 40% elastic material, or at least about 45% elastic material, or at least about 50% elastic material. Alternatively, the moisture-absorbent or moisture-adsorbent fabric of the first pouch layer 140 may include at least 0% elastic material to at least 50% elastic material, or at least 1% elastic material to at least 25% elastic material, although the first pouch layer 140 may also be comprised of a percentage of elastic material that is somewhat greater than these values. For example, the moisture-absorbent or moisture-adsorbent fabric of the first pouch layer 140 may include at least 1% elastic material, or at least 2% elastic material, or at least 3% elastic material, or at least 4% elastic material, or at least 5% elastic material, or at least 6% elastic material, or at least 7% elastic material, or at least 8% elastic material, or at least 9% elastic material, or at least 10% elastic material, or at least 12% elastic material, or at least 14% elastic material, or at least 16% elastic material, or at least 18% elastic material, or at least 20% elastic material, or at least 22% elastic material, or at least 24% elastic material, or at least 26% elastic material, or at least 28% elastic material, or at least 30% elastic material, or at least 35% elastic material, or at least 40% elastic material, or at least 45% elastic material, or at least 50% elastic material.

In some instances, at least a portion of the first pouch layer 140 (e.g., the first wearer-facing sublayer 150 and/or the first outward-facing sublayer 152) may comprise at least about 50% to at least about 100% polyester fibers, or at least about 75% to at least about 100% polyester fibers, although the first pouch layer 140 may also be comprised of a percentage of polyester fibers that is somewhat less than these values. For example, the first pouch layer 140 may comprise at least about 50% polyester fibers, or at least about 60% polyester fibers, or at least about 75% polyester fibers, or at least about 80% polyester fibers, or at least about 81% polyester fibers, or at least about 82% polyester fibers, or at least about 83% polyester fibers, or at least about 84% polyester fibers, or at least about 85% polyester fibers, or at least about 86% polyester fibers, or at least about 87% polyester fibers, or at least about 88% polyester fibers, or at least about 89% polyester fibers, or at least about 90% polyester fibers, or at least about 91% polyester fibers, or at least about 92% polyester fibers, or at least about 93% polyester fibers, or at least about 94% polyester fibers, or at least about 95% polyester fibers, or at least about 96% polyester fibers, or at least about 97% polyester fibers, or at least about 98% polyester fibers, or at least about 99% polyester fibers, or at least about 100% polyester fibers. In certain instances, at least a portion of the first pouch layer 140 may comprise up to about 100% polyester fibers. Alternatively, at least a portion of the first pouch layer 140 may comprise at least 50% to at least 100% polyester fibers, or at least 75% to at least 100% polyester fibers, although the first pouch layer 140 may also be comprised of a percentage of polyester fibers that is somewhat less than these values. For example, the first pouch layer 140 may comprise at least 50% polyester fibers, or at least 60% polyester fibers, or at least 75% polyester fibers, or at least 80% polyester fibers, or at least 81% polyester fibers, or at least 82% polyester fibers, or at least 83% polyester fibers, or at least 84% polyester fibers, or at least 85% polyester fibers, or at least 86% polyester fibers, or at least 87% polyester fibers, or at least 88% polyester fibers, or at least 89% polyester fibers, or at least 90% polyester fibers, or at least 91% polyester fibers, or at least 92% polyester fibers, or at least 93% polyester fibers, or at least 94% polyester fibers, or at least 95% polyester fibers, or at least 96% polyester fibers, or at least 97% polyester fibers, or at least 98% polyester fibers, or at least 99% polyester fibers, or at least 100% polyester fibers. In certain instances, at least a portion of the first pouch layer 140 may comprise up to 100% polyester fibers.

In other instances, at least a portion of the first pouch layer 140 (e.g., the first wearer-facing sublayer 150 and/or the first outward-facing sublayer 152) may comprise a blend of polyester and spandex. In such instances, at least a portion of the first pouch layer 140 may comprise at least about 0% spandex to at least about 25% spandex, although the first pouch layer 140 may also be comprised of a percentage of spandex that is somewhat greater than these values. For example, the first pouch layer 140 may comprise at least about 1% spandex, or at least about 3% spandex, or at least about 5% spandex, or at least about 6% spandex, or at least about 7% spandex, or at least about 8% spandex, or at least about 9% spandex, or at least about 10% spandex, or at least about 11% spandex, or at least about 12% spandex, or at least about 13% spandex, or at least about 14% spandex, or at least about 15% spandex, or at least about 16% spandex, or at least about 17% spandex, or at least about 18% spandex, or at least about 19% spandex, or at least about 20% spandex, or at least about 23% spandex, or at least about 25% spandex. Alternatively, at least a portion of the first pouch layer 140 may comprise at least 0% spandex to at least 25% spandex, although the first pouch layer 140 may also be comprised of a percentage of spandex that is somewhat greater than these values. For example, at least a portion of the first pouch layer 140 may comprise at least 1% spandex, or at least 3% spandex, or at least 5% spandex, or at least 6% spandex, or at least 7% spandex, or at least 8% spandex, or at least 9% spandex, or at least 10% spandex, or at least 11% spandex, or at least 12% spandex, or at least 13% spandex, or at least 14% spandex, or at least 15% spandex, or at least 16% spandex, or at least 17% spandex, or at least 18% spandex, or at least 19% spandex, or at least 20% spandex, or at least 23% spandex, or at least 25% spandex. However, in other instances, the first pouch layer 140 may comprise a percentage a spandex that is somewhat less or even greater than these values.

In addition to the examples provided above, the first pouch layer 140 (or portions thereof) may comprise any percentage of polyester fibers that falls within a range bounded by any minimum value and any maximum value as described above. Likewise, in some cases, the first pouch layer 140 (or portions thereof) may comprise any percentage of spandex that falls within a range bounded by any minimum value and any maximum value as described above. In still other instances, the first pouch layer 140 may comprise materials other than those explicitly described herein.

In some instances, at least a portion of the first pouch layer 140 (e.g., the first wearer-facing sublayer 150 and/or the first outward-facing sublayer 152) may comprise a double-knit fabric constructed from a polyester yarn, where the polyester yarn comprises up to about 100% polyester fibers (or up to 100% polyester fibers). For example, the first pouch layer 140 may comprise a 100% polyester double knit (e.g., weft knit). In other instances, the first pouch layer 140 may also comprise a rib, interlock, and/or jacquard fabric composed of a natural, synthetic, or semi-synthetic fabric (including blends thereof). The technical face 140*a* of the first pouch layer 140 may be imparted with a texture (e.g., a geometric or other pattern, a plurality of pores 151 or other features, etc.) to provide a soft, plush texture against the wearer's skin and/or to facilitate moisture absorbance, adsorbance, and/or transport (see FIG. 10A). By contrast, the technical face 142*a* of the second pouch layer 142 may be substantially flat and untextured (see FIG. 7). Among other things, a substantially flat and untextured fabric surface may be more conducive to further modification, such as lamination. In other instances, however, the second pouch layer 142 may be imparted with any suitable texture or surface features.

In some instances, at least a portion of the second pouch layer 142 (e.g., the second wearer-facing sublayer 154 and/or the second outward-facing sublayer 156) may comprise polyester, viscose, linen, lyocell, hemp, or other cellulosic fabrics. In certain instances, at least a portion of the second pouch layer 142 may comprise up to about 100% cotton fibers. For example, at least a portion of the second pouch layer 142 may comprise about 0% to about 100% cotton fibers, or about 50% to about 100% cotton fibers, although the second pouch layer 142 may also be comprised of a percentage of cotton fibers that is somewhat less than these values. For example, the second pouch layer 142 may comprise at least about 0% cotton fibers, or at least about 10% cotton fibers, or at least about 20% cotton fibers, or at least about 30% cotton fibers, or at least about 40% cotton fibers, or at least about 50% cotton fibers, or at least about 60% cotton fibers, or at least about 70% cotton fibers, or at least about 80% cotton fibers, or at least about 90% cotton fibers, or no more than about 100% cotton fibers. In certain instances, at least a portion of the second pouch layer 142 may comprise about 100% cotton fibers. Alternatively, at least a portion of the second pouch layer 142 may comprise 0% to 100% cotton fibers, or 50% to 100% cotton fibers, although the second pouch layer 142 may also be comprised of a percentage of cotton fibers that is somewhat less than these values. For example, at least a portion of the second pouch layer 142 may comprise at least 0% cotton fibers, or at least 10% cotton fibers, or at least 20% cotton fibers, or at least 30% cotton fibers, or at least 40% cotton fibers, or at least 50% cotton fibers, or at least 60% cotton fibers, or at least 70% cotton fibers, or at least 80% cotton fibers, or at least 90% cotton fibers, or no more than 100% cotton fibers. In certain instances, at least a portion of the second pouch layer 142 may comprise 100% cotton fibers.

In other instances, at least a portion of the second pouch layer 142 (e.g., the second wearer-facing sublayer 154 and/or the second outward-facing sublayer 156) may comprise a blend of a natural material (e.g., cotton, wool, linen, hemp, and the like) and an elastic material (e.g., a material that is stretchable to some degree such as rubber, latex, silicone, elastane, recycled elastane, organic materials with elastic core, and the like). In such instances, at least a portion of the second pouch layer 142 may include at least about 1% elastic material to at least about 25% elastic material, although the second pouch layer 142 may also be comprised of a percentage of elastic material that is somewhat greater than these values. For example, at least a portion of the second pouch layer 142 may include at least about 1% elastic material, or at least about 2% elastic material, or at least about 3% elastic material, or at least about 4% elastic material, or at least about 5% elastic material, or at least about 6% elastic material, or at least about 7% elastic material, or at least about 8% elastic material, or at least about 9% elastic material, or at least about 10% elastic material, or at least about 12% elastic material, or at least about 14% elastic material, or at least about 16% elastic material, or at least about 18% elastic material, or at least about 20% elastic material, or at least about 22% elastic material, or at least about 24% elastic material, or at least about 25% elastic material. Alternatively, at least a portion of the second pouch layer 142 may include at least 1% elastic material to at least 25% elastic material, although the second pouch layer 142 may also be comprised of a percentage of elastic material that is somewhat greater than these values. For example, at least a portion of the second pouch layer 142 may include at least 1% elastic material, or at least 2% elastic material, or at least 3% elastic material, or at least 4% elastic material, or at least 5% elastic material, or at least 6% elastic material, or at least 7% elastic material, or at least 8% elastic material, or at least 9% elastic material, or at least 10% elastic material, or at least 12% elastic material, or at least 14% elastic material, or at least 16% elastic material, or at least 18% elastic material, or at least 20% elastic material, or at least 22% elastic material, or at least 24% elastic material, or at least 25% elastic material.

In some instances, at least a portion of the second pouch layer 142 (e.g., the second wearer-facing sublayer 154 and/or the second outward-facing sublayer 156) may comprise a natural material (e.g., cotton) in an amount of at least about 0% to at least about 100%, although the second pouch layer 142 may also be comprised of a percentage of a natural material such as cotton that is somewhat less than these values. For example, at least a portion of the second pouch layer 142 may comprise at least about 0% natural material, or at least about 10% natural material, or at least about 20% natural material, or at least about 30% natural material, or at least about 40% natural material, or at least about 50% natural material, or at least about 60% natural material, or at least about 70% natural material, or at least about 80% natural material, or at least about 90% natural material, or no more than about 100% natural material. Alternatively, at least a portion of the second pouch layer 142 may comprise a natural material (e.g., cotton) in an amount of at least 0% to at least 100%, although the second pouch layer 142 may be comprised of a percentage of a natural material such as cotton that is somewhat less than these values. For example, at least a portion of the second pouch layer 142 may comprise at least 0% natural material, or at least 10% natural material, or at least 20% natural material, or at least 30% natural material, or at least 40% natural material, or at least 50% natural material, or at least 60% natural material, or at least 70% natural material, or at least 80% natural material, or at least 90% natural material, or no more than 100% natural material.

In other instances, at least a portion of the second pouch layer 142 (e.g., the second wearer-facing sublayer 154 and/or the second outward-facing sublayer 156) may comprise a blend of polyester and spandex. In such instances, at least a portion of the second pouch layer 142 may comprise at least about 1% spandex to at least about 25% spandex, although the second pouch layer 142 may be comprised of a percentage of spandex that is somewhat greater than these values. For example, at least a portion of the second pouch layer 142 may comprise at least about 1% spandex, or at least about 2% spandex, or at least about 3% spandex, or at least about 4% spandex, or at least about 5% spandex, or at least about 6% spandex, or at least about 7% spandex, or at least about 8% spandex, or at least about 9% spandex, or at least about 10% spandex, or at least about 12% spandex, or at least about 14% spandex, or at least about 16% spandex, or at least about 18% spandex, or at least about 20% spandex, or at least about 22% spandex, or at least about 24% spandex, or at least about 25% spandex. Alternatively, at least a portion of the second pouch layer 142 may comprise at least 1% spandex to at least 25% spandex, although the second pouch layer 142 may be comprised of a percentage of spandex that is somewhat greater than these values. For example, at least a portion of the second pouch layer 142 may comprise at least 1% spandex, or at least 2% spandex, or at least 3% spandex, or at least 4% spandex, or at least 5% spandex, or at least 6% spandex, or at least 7% spandex, or at least 8% spandex, or at least 9% spandex, or at least 10% spandex, or at least 12% spandex, or at least 14% spandex, or at least 16% spandex, or at least 18% spandex, or at least 20% spandex, or at least 22% spandex, or at least 24% spandex, or at least 25% spandex.

In further instances, the second pouch layer 142 (e.g., the second wearer-facing sublayer 154 and/or the second outward-facing sublayer 156) may comprise other materials such as any natural, synthetic, or semi-synthetic fabric (including blends thereof).

In certain instances, a first material may be used to impart the garment 100 with moisture management properties. For example, in instances in which the first pouch layer 140 and/or the second pouch layer 142 include a synthetic material such as polyester (e.g., polyester yarns, fabrics comprising polyester, etc.), the polyester may be imparted with a fabric weight selected for desired moisture-management properties. The first material may be imparted with a fabric weight of at least about 135 grams per square meter (gsm) to at least about 185 gsm (or at least about 135 gsm to at least about 185 gsm), although the first material may be imparted with a fabric weight less than or greater than these values. For example, in some instances, the first material may be imparted with a weight of at least about 135 gsm, or at least about 140 gsm, or at least about 143 gsm, or at least about 146 gsm, or at least about 148 gsm, or at least about 150 gsm, or at least about 152 gsm, or at least about 154 gsm, or at least about 156 gsm, or at least about 158 gsm, or at least about 160 gsm, or at least about 162 gsm, or at least about 164 gsm, or at least about 166 gsm, or at least about 168 gsm, or at least about 170 gsm, or at least about 172 gsm, or at least about 174 gsm, or at least about 176 gsm, or at least about 178 gsm, or at least about 180 gsm, or no more than about 185 gsm. Alternatively, the first material may be imparted with a weight of least 135 gsm, or at least 140 gsm, or at least 143 gsm, or at least 146 gsm, or at least 148 gsm, or at least 150 gsm, or at least 152 grams per square meter, or at least 154 gsm, or at least 156 gsm, or at least 158 gsm, or at least 160 gsm, or at least 162 gsm, or at least 164 gsm, or at least 166 gsm, or at least 168 gsm, or at least 170 gsm, or at least 172 gsm, or at least 174 gsm, or at least 176 gsm, or at least 178 gsm, or at least 180 gsm, or no more than 185 gsm.

In other instances, a second material may be provided as the first pouch layer 140 and/or the second pouch layer 142. The second material may, for example, provide enhanced moisture-management properties to the wearer. In certain instances, the second material may be a synthetic material (e.g., polyester) imparted with a weight of at least about 230 gsm to at least about 295 gsm (or at least 230 gsm to at least 290 gsm), although the second material may be imparted with a weight somewhat less or even greater than these values. For example, the second material may be imparted with a weight of at least about 240 gsm, or at least about 242 gsm, or at least about 245 gsm, or at least about 250 gsm, or at least about 255 gsm, or at least about 260 gsm, or at least about 265 gsm, or at least about 270 gsm, or at least about 275 gsm, or at least about 280 gsm, or at least about 285 gsm, or at least about 290 gsm, or no more than about 295 gsm. Alternatively, the second material may be imparted with a weight of at least 240 gsm to at least 295 gsm. For example, the second material may be imparted with a weight of at least 240 gsm, or at least 242 gsm, or at least 245 gsm, or at least 250 gsm, or at least 255 gsm, or at least 260 gsm, or at least 265 gsm, or at least 270 gsm, or at least 275 gsm, or at least 280 gsm, or at least 285 gsm, or at least 290 gsm, or no more than 295 gsm. In some instances, the second material may be imparted with a greater surface area as compared to the first material (e.g., due to surface texture or other aspects of the material) such that the second material is capable of trapping, capturing, and/or transporting more moisture than the first material.

In yet other instances, one or more layers of the pouch 114 (e.g., the first panel **138*a*, the second panel 138*b*, or one or more layers or sublayers thereof) may be constructed of a fabric having a weight falling within any of the values or ranges recited above with respect to the first and second materials. Alternatively, one or more layers of the pouch 114 (e.g., the first panel 138*a***, the cover may be constructed of a fabric having a weight that is different from any of the values or ranges provided herein.

In some instances, the fabric weights listed above may only apply to the fabrics comprising the first pouch layer 140 (e.g., the first wearer-facing sublayer 150 and/or the first outward-facing sublayer 152) and/or the second pouch layer 142 (e.g., the second wearer-facing sublayer 154 and/or the second outward-facing sublayer 156) and may not include the weights of any additional substances applied to the fabrics (e.g., a laminated film). However, in other instances, one or more layers of the pouch 114 may include a hydrophobic film, as described in further detail below with reference to FIG. 12, and the fabric weights listed above may include the film.

In some instances, the second wearer-facing sublayer 154 of the second pouch layer 142 may be substantially the same as the second outward-facing sublayer 156 of the second pouch layer. However, in other instances, the second wearer-facing sublayer 154 and the second outward-facing sublayer 156 may be provided in different forms. Further, as shown in FIGS. 11 and 12, the second pouch layer 142, namely one or both of the second wearer-facing sublayer 154 and the second outward-facing sublayer 156, may be treated with an agent that enhances the ability of the second pouch layer 142 to repel moisture, such as a durable water repellent ("DWR"). For example, the second pouch layer 142 may be treated with HeiQ Eco-Dry, a non-polyfluorinated chemical ("PFC") available from HeiQ Materials AG (Zurich, Switzerland), or the second pouch layer 142 may be treated with other suitable water-repellent or water-resistant agents. Without being bound to a particular theory, it is believed that the application of a DWR treatment to a fabric may modify the surface energy properties of the fabric, such as reducing the surface tension of the fabric surface, which thereby reduces the adhesion of water droplets to the fabric surface such that water droplets roll or disperse off the fabric surface. It is to be understood that the DWR treatments described herein may be applied to any fabric or fabric layer comprising the garment 100.

In certain instances, a first agent may be applied to the first pouch layer 140 and a second agent may be applied to the second pouch layer 142. For example, as shown in FIG. 12, the first agent may be applied to the first outward-facing sublayer 152 of the first pouch layer 140 and the second agent may be applied to the second wearer-facing sublayer 154 and the second outward-facing sublayer 156 of the second pouch layer 142. Both the first agent and the second agent may be selected from the group consisting of a water-repellant agent, a water-resistant agent, a hygiene agent, an odor control agent, an antimicrobial agent, and combinations thereof. In some such instances, the first agent and the second agent may be different, or the first agent and the second agent may be the same.

As shown in FIG. 12, in some instances, the pouch 114 may include a hydrophobic film 153 (e.g., the first panel 138*a* and/or the second panel 138*b* may include a hydrophobic film 153). For example, the hydrophobic film 153 may be positioned on the first pouch layer 140 and/or the second pouch layer 142 (e.g., the first pouch layer 140 and/or the second pouch layer 142 may be laminated with, bonded to, or otherwise coupled to the hydrophobic film 153). The hydrophobic film 153 may be configured to be substantially water-impermeable while enabling water vapor to pass therethrough. As shown in FIG. 12, in some instances, the hydrophobic film 153 may be provided as a component of the first pouch layer 140 and may be positioned between the first outward-facing sublayer 152 and the second wearer-facing sublayer 154. For example, the hydrophobic film 153 may be laminated or otherwise coupled to the technical back 140*b* of the first pouch layer 140. However, in other instances, the hydrophobic film 153 may be incorporated into or arranged on any of the layers of the pouch 114 and/or may be coupled to a technical face or a technical back of any of the layers or sublayers of the pouch 114.

In some instances, the hydrophobic film 153 may be provided in the form of a thermoplastic film formed from thermoplastic polyurethane (TPU). However, other suitable thermoplastic films may comprise polyolefin, polyurethane, and the like. Alternatively, the hydrophobic film 153 may comprise silicone or any other suitable material. In some instances, the first pouch layer 140 may be treated with a wicking agent that enhances the ability of the first pouch layer 140 to wick moisture, a soil release agent that enhances the ability of the first pouch layer 140 to repel soils/stains, an odor control agent, and/or a hygiene agent. For example, in some instances, the first pouch layer 140 may be treated with a hygiene agent configured to impart the first pouch layer 140 with antibacterial properties. In certain instances, a single agent, such as Agion® (available from Sciessent, Beverly, MA, USA) or another comparable agent may provide both odor control and hygiene (e.g., antibacterial) benefits. It is to be understood that the garment 100, including the pouch 114, may omit the hydrophobic film 153, wicking agents, and/or any other treatments described herein. It is also to be understood that the hydrophobic film 153, wicking agents, and/or any other treatments described herein may be applied to any of the fabrics or fabric layers comprising the garment 100.

Depending on the desired characteristics of the pouch 114, the first and second pouch layers 140, 142 may comprise a single type of fabric or material (e.g., including fabrics that comprise a blend of materials), or the first and second pouch layers 140, 142 may include two or more distinct types of fabric or material. For example, as shown in FIG. 11, the first wearer-facing sublayer 150 and the first outward-facing sublayer 152 of the first pouch layer 140 may be provided in substantially the same form, and the second wearer-facing sublayer 154 and the second outward-facing sublayer 156 of the second pouch layer 142 may be provided in substantially the same form. However, in other instances, the first wearer-facing sublayer 150 and the first outward-facing sublayer 152 of the first pouch layer 140 may be provided in different forms, as shown in FIGS. 11 and 12.

Additionally, in some instances, the second wearer-facing sublayer 154 and the second outward-facing sublayer 156 of the second pouch layer 142 may be provided in different forms. For example, as shown in FIG. 13, the first wearer-facing sublayer 150, the first outward-facing sublayer 152, the second wearer-facing sublayer 154, and/or the second outward-facing sublayer 156 may be imparted with different properties relative to one another. In some such instances, as shown in FIG. 13, the first outward-facing sublayer 152, the second wearer-facing sublayer 154, and/or the second outward-facing sublayer 156 may be treated with a first agent, a second agent, and a third agent, respectively. Each of the first, second, third agent may be selected from the group consisting of a water-repellant agent, a water-resistant agent, a hygiene agent, an odor control agent, an antimicrobial agent, and combinations thereof. In some such instances, the first agent, the second agent, and the third agent may be different, or at least one of the first agent, the second agent, and the third agent may be the same as the other agents. In addition, in some cases, the fabric or material of the first outward-facing sublayer 152 may be imparted with a first weight, the fabric or material of the second wearer-facing sublayer 154 may be imparted with a second weight, and the fabric or material of the second outward-facing sublayer 156 may be imparted with a third weight. Alternatively, the first outward-facing sublayer 152, the second wearer-facing sublayer 154, and/or the second outward-facing sublayer 156 may differ with regard to one or more other properties or attributes.

Figure 14:
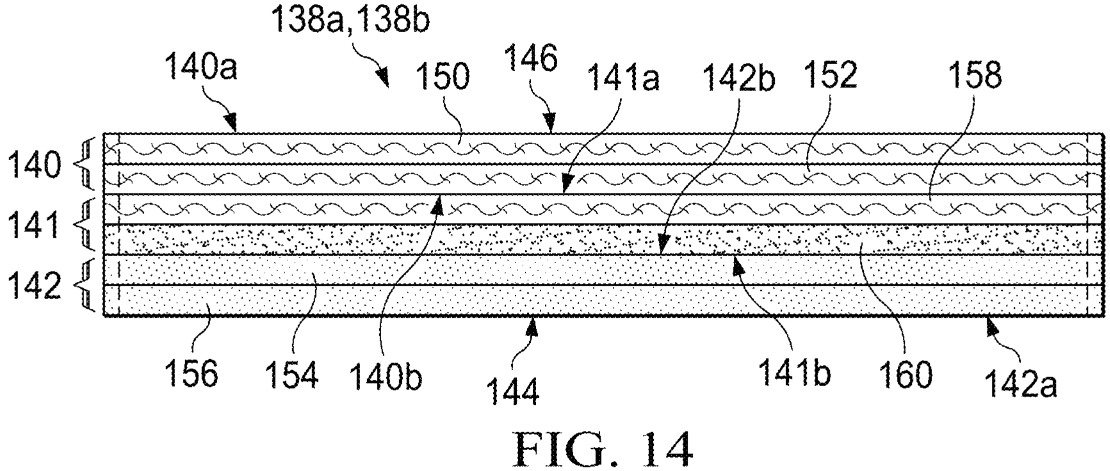
FIG. 14 is a schematic representation of fabric layers of a portion of a panel of yet another example pouch as depicted in any of FIGS. 1-8.

Turning to FIG. 14, in some instances, the pouch 114 may be provided in the form of three fabric layers including the first pouch layer 140, the second pouch layer 142, and the third pouch layer 141. The third pouch layer 141 may be positioned between the first and second pouch layers 140, 142, or the third pouch layer 141 may be positioned on either side of the first and/or second pouch layers 140, 142. Additionally, in some instances, the pouch 114 may include additional layers of fabric or material provided in substantially the same form or in a different form as compared to the third pouch layer 141 (e.g., a fourth pouch layer, a fifth pouch layer, etc.). The various fabric layers of the pouch 114 may be made of the same materials or different materials. In addition, a hydrophobic film, wicking agents, and/or any other treatments described herein may be applied to any of the various fabric layers of the pouch 114 (e.g., the third pouch layer 141, a fourth pouch layer, a fifth pouch layer, etc.).

In some instances, the first pouch layer 140 may be the wearer-facing layer, and the second pouch layer 142 may be visible from an exterior of the garment 100 when the garment 100 is worn in its intended configuration. In such instances, the third pouch layer 141 may be disposed between the first outward-facing sublayer 152 and the second wearer-facing sublayer 154 (or between the technical back 140*b* of the first pouch layer 140 and the technical back 142*b* of the second pouch layer 142). Alternatively, the third pouch layer 141 may be provided as the wearer-facing layer or may be visible from an exterior of the garment 100. Like the first and second pouch layers 140, 142, the third pouch layer 141 may include one or more layers of fabric or material.

In the example of FIG. 14, the third pouch layer 141 includes a third wearer-facing sublayer 158 and a third outward-facing sublayer 160, and the third wearer-facing sublayer 158 and the third outward-facing sublayer 160 are provided in substantially the same form relative to one another. However, in other instances, the third pouch layer 141 may include more or fewer sublayers, and one or more of the sublayers of the third pouch layer 141 may be provided in substantially the same form or in different forms. For example, the first and third pouch layers 141 may in some instances be substantially similar and the first wearer-facing sublayer 150, the first outward-facing sublayer 152, the third wearer-facing sublayer 158, and/or the third outward-facing sublayer 160 may comprise substantially the same materials.

Like the first and second panels 138*a*, 138*b* of FIGS. 12 and 13, in some instances, one or more agents may be applied to the layers comprising the first and second panels 138*a*, 138*b* of FIG. 14. For instance, as depicted in FIG. 14, the third outward-facing sublayer 160 of the third pouch layer 141 may be treated with a first agent and the second agent may be applied to the second wearer-facing sublayer 154 and the second outward-facing sublayer 156 of the second pouch layer 142. Both the first agent and the second agent may be selected from the group consisting of a water-repellant agent, a water-resistant agent, a hygiene agent, an odor control agent, an antimicrobial agent, and combinations thereof. In some such instances, the first agent and the second agent may be different, or the first agent and the second agent may be the same.

Like the first and second pouch layers 140, 142, the third pouch layer 141 may include a technical face 141*a* (e.g., the third wearer-facing sublayer 158) and a technical back 141*b* (e.g., the third outward-facing sublayer 160). In some instances, the third pouch layer 141 may be oriented such that the technical face 141*a* of the third pouch layer 141 is adjacent to the technical back 140*b* of the first pouch layer 140 and the technical back 141*b* of the third pouch layer 141 is adjacent to the technical back 142*b* of the second pouch layer 142.

The third pouch layer 141 (e.g., the third wearer-facing sublayer 158 and/or the third outward-facing sublayer 160) may comprise substantially similar materials or different materials as compared to the first and second pouch layers 140, 142. For example, in some instances, at least a portion of the third pouch layer 141 may be provided in the form of a moisture-absorbent or moisture-adsorbent fabric comprising an elastic material (e.g., a material that is stretchable to some degree such as rubber, latex, silicone, elastane, recycled elastane, organic materials with elastic core, and the like). Thus, the moisture-absorbent or moisture-adsorbent fabric of the third pouch layer 141 may include at least about 1% to at least about 50% elastic material, or at least about 1% to at least about 25% elastic material, although the third pouch layer 141 may be comprised of a percentage of elastic material that is somewhat greater than these values. For example, the moisture-absorbent or moisture-adsorbent fabric of the third pouch layer 141 may include at least about 1% elastic material, or at least about 2% elastic material, or at least about 3% elastic material, or at least about 4% elastic material, or at least about 5% elastic material, or at least about 6% elastic material, or at least about 7% elastic material, or at least about 8% elastic material, or at least about 9% elastic material, or at least about 10% elastic material, or at least about 12% elastic material, or at least about 14% elastic material, or at least about 16% elastic material, or at least about 18% elastic material, or at least about 20% elastic material, or at least about 22% elastic material, or at least about 24% elastic material, or at least about 25% elastic material. Alternatively, the moisture-absorbent or moisture-adsorbent fabric of the third pouch layer 141 may include at least 1% to at least 50% elastic material, or at least 1% to at least 25% elastic material, although the third pouch layer 141 may be comprised of a percentage of elastic material that is somewhat greater than these values. For example, the moisture-absorbent or moisture-adsorbent fabric of the third pouch layer 141 may include at least 1% elastic material, or at least 2% elastic material, or at least 3% elastic material, or at least 4% elastic material, or at least 5% elastic material, or at least 6% elastic material, or at least 7% elastic material, or at least 8% elastic material, or at least 9% elastic material, or at least 10% elastic material, or at least 12% elastic material, or at least 14% elastic material, or at least 16% elastic material, or at least 18% elastic material, or at least 20% elastic material, or at least 22% elastic material, or at least 24% elastic material, or at least 25% elastic material.

In some instances, at least a portion of the third pouch layer 141 (e.g., the third wearer-facing sublayer 158 and/or the third outward-facing sublayer 160) may comprise at least about 0% polyester fibers to at least about 100% polyester fibers, or at least about 50% polyester fibers to at least about 100% polyester fibers, although the third pouch layer 141 may also be comprised of a percentage of polyester fibers that is somewhat less than these values. For example, at least a portion of the third pouch layer 141 may comprise at least about 0% polyester fibers, or at least about 10% polyester fibers, or at least about 20% polyester fibers, or at least about 30% polyester fibers, or at least about 40% polyester fibers, or at least about 50% polyester fibers, or at least about 60% polyester fibers, or at least about 70% polyester fibers, or at least about 80% polyester fibers, or at least about 90% polyester fibers, or no more than about 100% polyester fibers. In certain instances, at least a portion of the third pouch layer 141 may comprise up to about 100% polyester fibers. Alternatively, at least a portion of the third pouch layer 141 may comprise at least 0% polyester fibers to at least 100% polyester fibers, or at least 50% polyester fibers to at least 100% polyester fibers, although the third pouch layer 141 may be comprised of a percentage of polyester fibers that is somewhat less than these values. For example, at least a portion of the third pouch layer 141 may comprise at least 10% polyester fibers, or at least 20% polyester fibers, or at least 30% polyester fibers, or at least 40% polyester fibers, or at least 50% polyester fibers, or at least 60% polyester fibers, or at least 70% polyester fibers, or at least 80% polyester fibers, or at least 90% polyester fibers, or no more than 100% polyester fibers. In certain instances, at least a portion of the third pouch layer 141 may comprise up to 100% polyester fibers.

In some instances, at least a portion of the third pouch layer 141 (e.g., the third wearer-facing sublayer 158 and/or the third outward-facing sublayer 160) may comprise a blend of polyester and spandex. In such instances, at least a portion of the third pouch layer 141 may comprise at least about 1% spandex to at least about 25% spandex, with the remainder of the third pouch layer 141 comprising polyester, although the third pouch layer 141 may also be comprised of a percentage of spandex that is somewhat greater than these values. For example, the third pouch layer 141 may comprise at least about 1% spandex, or at least about 2% spandex, or at least about 3% spandex, or at least about 4% spandex, or at least about 5% spandex, or at least about 6% spandex, or at least about 7% spandex, or at least about 8% spandex, or at least about 9% spandex, or at least about 10% spandex, or at least about 12% spandex, or at least about 14% spandex, or at least about 16% spandex, or at least about 18% spandex, or at least about 20% spandex, or at least about 22% spandex, or at least about 24% spandex, or at least about 25% spandex. Alternatively, at least a portion of the third pouch layer 141 may comprise at least 1% spandex to at least 25% spandex, although the third pouch layer 141 may also be comprised of a percentage of spandex that is somewhat greater than these values. For example, at least a portion of the third pouch layer 141 may comprise at least 1% spandex, or at least 2% spandex, or at least 3% spandex, or at least 4% spandex, or at least 5% spandex, or at least 6% spandex, or at least 7% spandex, or at least 8% spandex, or at least 9% spandex, or at least 10% spandex, or at least 12% spandex, or at least 14% spandex, or at least 16% spandex, or at least 18% spandex, or at least 20% spandex, or at least 22% spandex, or at least 24% spandex, or at least 25% spandex. However, in other instances, the third pouch layer 141 may comprise a percentage a spandex that is somewhat less or even greater than these values.

While not depicted in FIG. 14, in some instances, the pouch 114 may include additional layers (e.g., additional moisture-absorbent or moisture-adsorbent layers) positioned between or on either side of the first and second pouch layers 140, 142, and the further layers may be provided in a substantially similar form or a different form as compared to the third pouch layer 141.

In some instances, the rear panel 126 may also be provided with one or more portions or fabric layers to impart moisture management properties. In these instances, the above discussion with regard to FIGS. 11-14 also applies to the rear panel 126, which may be substantially similar to the front panel 121 or the pouch 114. For example, in some instances, the rear panel 126 may be imparted with similar surface areas, materials, fabric layers, dimensions, and/or other characteristics as compared to the pouch 114. However, in certain instances, the rear panel 126 may be substantially similar to the pouch 114 in some respects but may have a different shape and/or different dimensions as compared to the pouch 114 (e.g., the rear panel 126 may be larger than the pouch 114).

It is to be understood that any of the agents or treatments described herein may be applied to any of the technical faces, technical backs, or sublayers of the fabrics described herein (e.g., the wearer-facing sublayer 150, the first outward-facing sublayer 152, the second wearer-facing sublayer 154, the second outward-facing sublayer 156, the third wearer-facing sublayer 158 and the third outward-facing sublayer 160 of FIGS. 11-14). In addition, the same agent or treatment need not be applied to each of the technical faces, technical backs, or sublayers of the fabrics described herein (e.g., different agents or treatments may be applied to different technical faces, technical backs, or sublayers of the fabrics).

Figure 15:
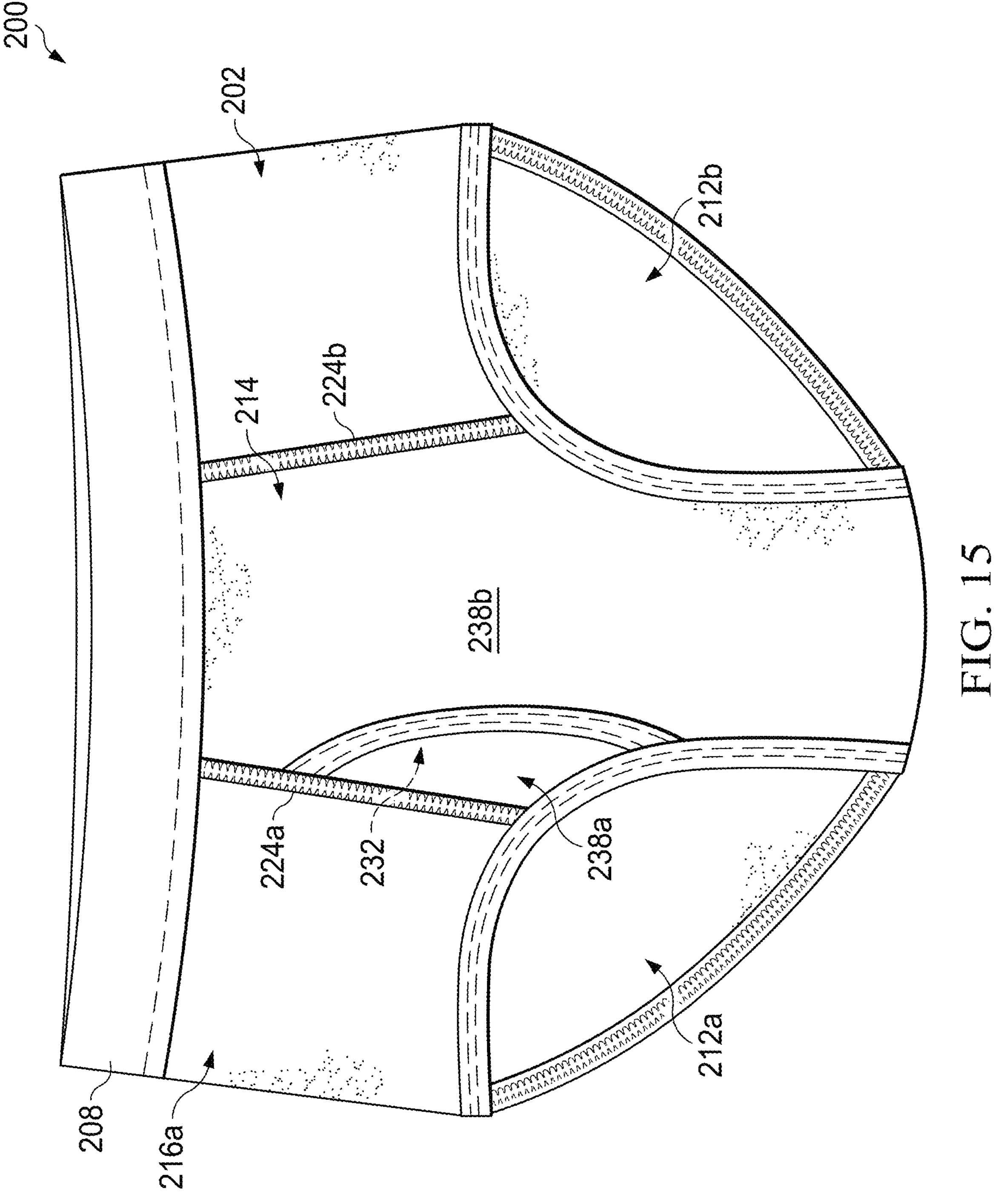
FIG. 15 is a front elevational view of another moisture management garment constructed according to the teachings herein.
Figure 16:
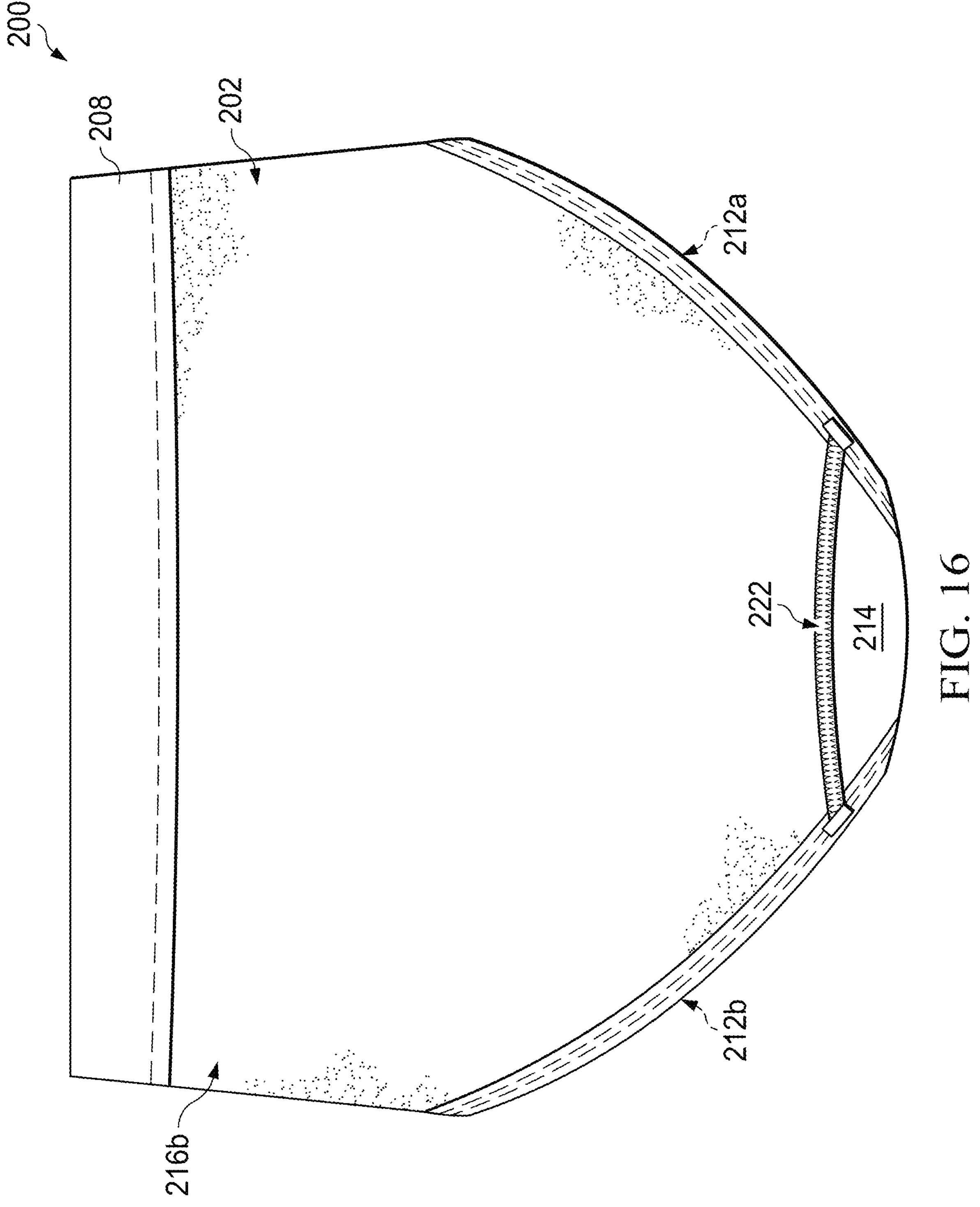
FIG. 16 is a rear elevational view of the moisture management garment of FIG. 15.

FIGS. 15 and 16 illustrate an additional, non-limiting example of the garment 200 (e.g., the lower torso garment 200) that may include one or more moisture management portions (e.g., a pouch) constructed in accordance with the present disclosure. The reference numbers used to identify different features of FIGS. 15 and 16 are similar to the reference numbers used throughout the disclosure. The garment 200 shown in FIGS. 15 and 16 may be substantially similar to the garment 100 as described above with reference to FIGS. 1-14 and may also provide moisture management benefits to the wearer. In various instances, elements of the garment 200 having similar names and/or reference numbers as features of the garment 100 may be provided in substantially the same form as the features described with reference to the garment 100. For example, as described above, the garment 200 may include a pouch (e.g., a pouch 214) that, in use or wear, is positioned near the wearer's external genitals and is configured to provide moisture management properties.

Like the garment 100, the garment 200 may be provided in the form of a body 202 that includes a waistband 208, left and right leg openings 212*a*, 212*b*, and the pouch 214. The pouch 214 may include a first panel 238*a* and a second panel 238*b* which at least partially define a fly opening 232. However, in some instances the fly opening 232 may be omitted (e.g., the garment 200 may include one of the first and second panels 238*a*, 238*b*, but the other of the first and second panels 238*a*, 238*b* may be omitted). In some instances, the body 202 may be provided in the form of a front lower torso portion 216*a* (see FIG. 15) and a rear lower torso portion 216*b* (see FIG. 16). One or more pouch seams 224, such as a first pouch seam 224*a* and a second pouch seam 224*b*, may at least partially define the shape of the pouch 214. Additionally, in some instances, the garment 200 may include a rear seam 222 (e.g., arranged to be adjacent to a rear portion of a wearer's body when the garment 200 is worn in its intended configuration) which may define at least a portion or an edge of the pouch 214. In other instances, the garment 200 may include additional or alternative components not specifically depicted and described herein.

In some instances, the garment 200 may not include a gusset (e.g., a gusset analogous to the gusset 118 of the garment 100). Instead, at least a portion of the pouch 214 may be positioned on the front lower torso portion 216*a* while another portion of the pouch 214 may extend to the rear lower torso portion 216*b*. For example, the pouch 214 may be coupled to the rear lower torso portion 216*b* via a rear seam 222 of the garment 200. In other instances, the pouch 214 may be provided in any suitable form and may be located on any suitable portion of the garment 100.

Unlike the instances of the garment 100 illustrated in FIGS. 1-8, in some instances, the garment 200 may be provided in the form of briefs. In such instances, the garment 200 may not include leg portions (e.g., the leg portions 110 as described with reference to FIG. 1 may be omitted). In addition, the shape of the pouch 214 may be different than the shape of the first pouch 114*a* (e.g., see FIG. 1) and/or the second pouch 114*b* (e.g., see FIG. 3). However, the pouch 214 may in some instances be imparted with a substantially similar shape as either of the first and second pouches 114*a*, 114*b*. The pouch 214 may also differ from the pouch 114 in one or more other respects. While the garment 200 may in some instances be provided in the form of briefs, the garment 200 may be provided in other forms such as pants, leggings, joggers, tights, stockings, bicycle shorts, a liner for another garment, and/or other forms of lower torso garments.

Figure 17:
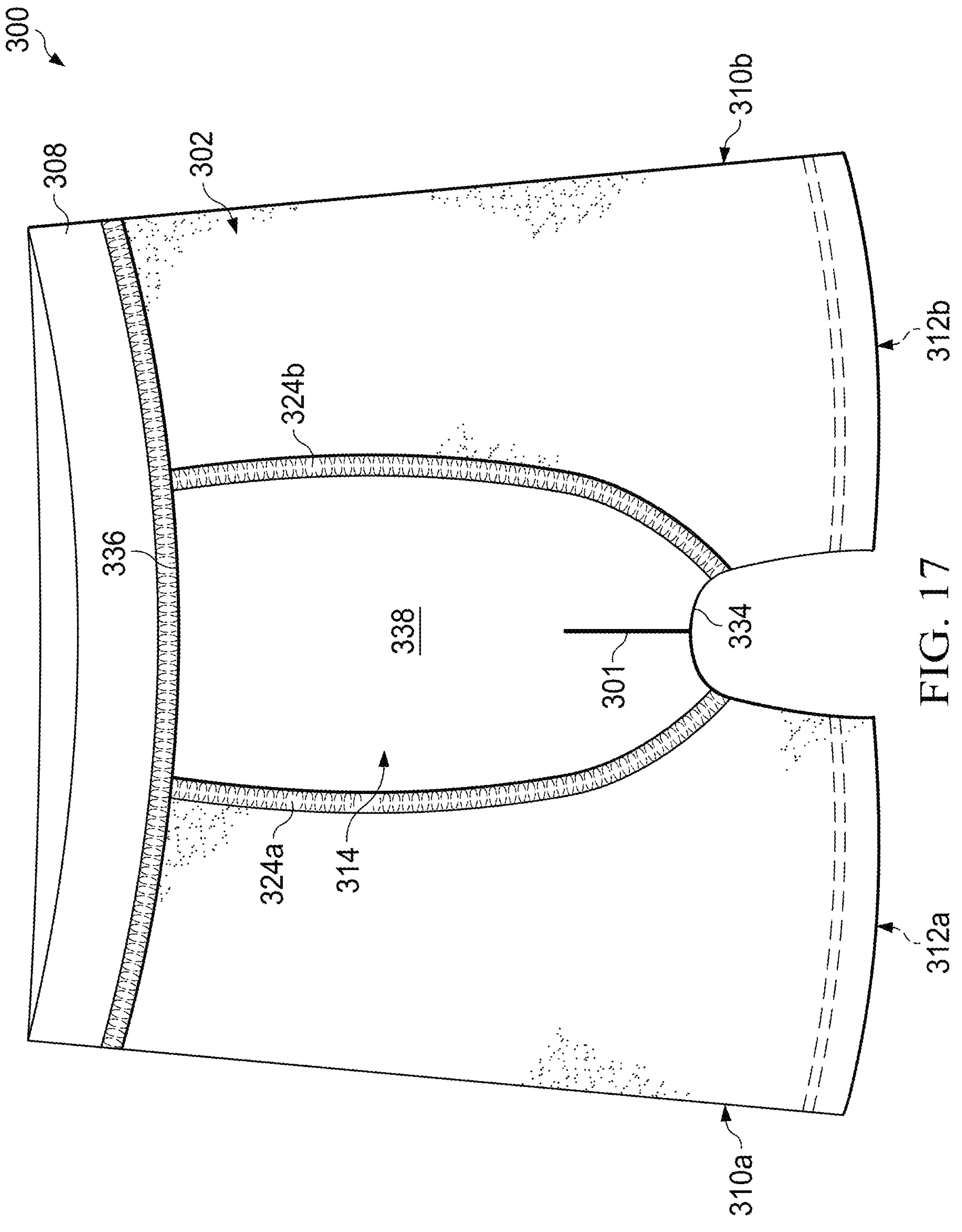
FIG. 17 is a front elevational view of a further moisture management garment constructed according to the teachings herein.
Figure 18B:
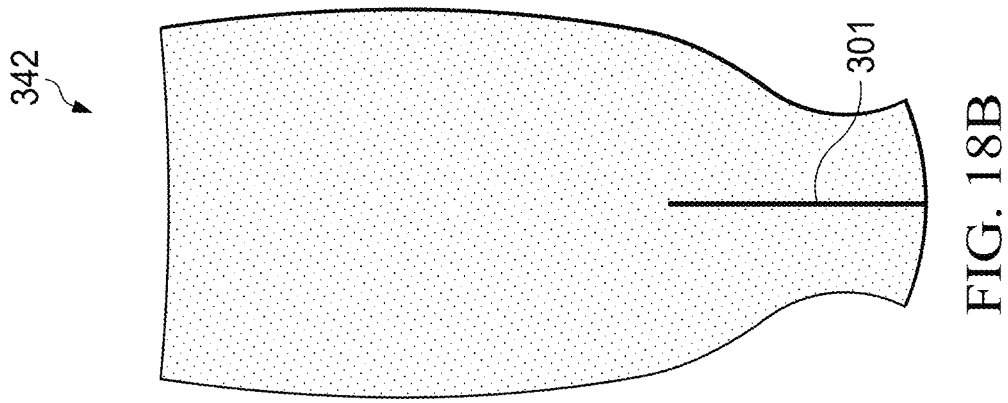
FIG. 18B is a front elevational view of a second portion of a panel of the garment of FIG. 17.

FIGS. 17-18B depict a further, non-limiting example of a garment 300 (e.g., a lower torso garment 300) that may include one or more moisture management portions (e.g., a pouch) constructed in accordance with the present disclosure. The reference numbers used to identify different features of FIGS. 17-18B are similar to the reference numbers used throughout the disclosure. The garment 300 of FIGS. 17-18B may be substantially similar to the garment 100 and/or the garment 200 as described above with reference to FIGS. 1-16 and may also provide moisture management benefits to the wearer. In various instances, elements of the garment 300 having similar names and/or reference numbers as features of the garment 100 and/or the garment 200 may be provided in substantially the same form as the corresponding features described with respect to the garments 100, 200. For example, as described above, the garment 300 may include a pouch (e.g., a pouch 314) that, in use or wear, is positioned near the wearer's external genitals and is configured to provide moisture management properties. In the example of FIGS. 17-18B, the garment 300 may be provided in the form of a boxer brief. However, in other instances, the garment 300 may be provided in other forms such as a brief, boxer shorts, leggings, base layer, and/or other forms of lower torso garments or undergarments.

Like the garments 100, 200, the garment 300 may be provided in the form of a body 302 that includes a waistband 308, left and right leg portions 310*a*, 310*b*, left and right leg openings 312*a*, 312*b*, and the pouch 314. In some instances, the pouch 314 may be substantially similar to the pouches 114, 214 in one or more respects; however, the pouch 314 may differ from the pouches 114, 214 in that the pouch 314 may not include a fly opening (e.g., the fly opening 132 of the garment 100 shown in, for example, FIG. 1 may be omitted). Thus, in some configurations, the pouch 314 of the garment 300 may include a single panel 338 as opposed to including first and second panels that correspond to the first and second panels 138*a*, 138*b* of the garment 100 and first and second panels 238*a*, 238*b* of the garment 200. In some instances, one or more pouch seams 324, such as a first pouch seam 324*a* and a second pouch seam 324*b*, may at least partially define the shape of the pouch 314. In other instances, the garment 300 may include additional or alternative components not specifically described herein.

In some instances, the panel 338 of the pouch 314 may be provided in a substantially similar form as the first panel 138*a* and/or the second panel 138*b*, as described above with reference to the garment 100 (see, e.g., FIGS. 9A and 9B). For example, the panel 338 may be provided with the construction and/or arrangement of materials or layers of fabric or material depicted in any of FIGS. 9A, 9B, 11-14. The pouch 314 may be defined by a pouch first end 334 and a pouch second end 336 opposing the pouch first end 334. In some instances, the pouch 314 may be imparted with a substantially ovoid shape, may be substantially U-shaped, or may be imparted with other shapes. For example, the first and second pouch seams 324*a*, 324*b* may each include a substantially linear portion proximate to the pouch second end 336 and a substantially rounded portion proximate to the pouch first end 334. In this way, in some instances, a width of the pouch 314 may narrow from the pouch second end 336 to the pouch first end 334. In other instances, however, the first and second pouch seams 324*a*, 324*b* and the pouch 314 may be imparted with any suitable shape or structure.

In certain instances, the pouch 314 may be coupled to a gusset (not depicted) provided in the garment 300. In other instances, the gusset may be omitted from the garment 300. In such instances, the pouch 314 may be coupled to a rear panel or a rear portion of the body 302 (not depicted). In some cases, the pouch 314 may only be provided on a front portion of the garment 300, although in other cases the pouch 314 may extend onto the rear portion of the garment 300.

In some instances, the panel 338 of the pouch 314 may include a feature 301 (e.g., a seam, a region including stitching, etc.) positioned proximate to the pouch first end 334. For example, the feature 301 may be provided in the form of a dart designed to increase a volume of the pouch 314. However, in other instances, the feature 301 may be provided in a different form or the feature 301 may be omitted.

Figure 18A:
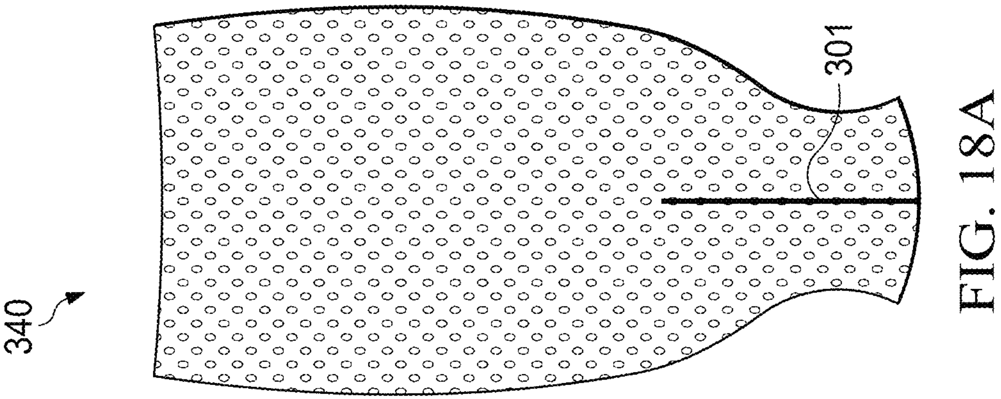
FIG. 18A is a front elevational view of a first portion of a panel of the garment of FIG. 17.

The panel 338 may include one or more fabric layers. For example, the panel 338 may comprise a single layer of fabric or material, or the panel 338 may include two, three, four, or any other number of layers of fabric or material. As shown in FIGS. 18A and 18B, in some instances, the panel 338 may include a first pouch layer 340 (FIG. 18A) and a second pouch layer 342 (FIG. 18B). For example, the first pouch layer 340 may be provided in the form of a moisture-absorbent or moisture-adsorbent layer and may be substantially similar to the first pouch layer 140 in one or more respects, and the second pouch layer 342 may be imparted with moisture-resistant properties and may be substantially similar to the second pouch layer 142 in one or more respects. However, in other instances, the first and second pouch layers 340, 342 may be provided in any suitable form and may differ from the first and second pouch layers 140, 142 in one or more respects (e.g., construction, position, materials, dimensions, etc.). Further, in some instances, the panel 338 may only include a single layer of fabric or material. For example, the second pouch layer 342 may be omitted in certain instances, and the pouch 314 may consist of the moisture-absorbent or moisture-adsorbent material of the first pouch layer 340. In other instances, the panel 338 may include any number of layers of fabric or material (e.g., two layers, three layers, four layers, etc.).

The first and second pouch layers 340, 342 may be provided in substantially the same shape, although the shape of the first and second pouch layers 340, 342 may also be different from each other. As shown in FIGS. 18A, 18B, the first and second pouch layers may each be provided in the form of an hourglass shape or wineglass shape, although the first and second pouch layers 340, 342 can be provided in a virtually limitless number of shapes. In addition, when the first and second pouch layers 340, 342 are coupled together and/or provided in the garment 300, the second pouch layer 342 may overlay the first pouch layer 340. Alternatively, the first and second pouch layers 340, 342 may be offset from each other when coupled together and/or provided in the garment 300.

In certain instances, any of the moisture management pouches (e.g., the pouch 114, 214, 314) and garments (e.g., the garments 100, 200, 300) described herein with reference to FIGS. 1-18B may retain their moisture management properties after being laundered. For example, the moisture-management pouches of FIGS. 1-18B may partially, substantially completely, or completely retain their moisture-management properties after being washed in a washing machine and/or dried in a dryer. In certain instances, the moisture-management pouches and garments of FIGS. 1-18B may partially, substantially completely, or completely retain their moisture-management properties after undergoing about 1 to about 50 laundry cycles (or 1 to 50 laundry cycles), although the moisture-management pouches may also retain the moisture-management properties after even more laundry cycles. For example, the moisture-management pouches and garments of FIGS. 1-18B may partially, substantially completely, or completely retain their moisture-management properties after undergoing at least about 1 laundry cycle, or at least about 3 laundry cycles, or at least about 5 laundry cycles, or at least about 7 laundry cycles, or at least about 10 laundry cycles, or at least about 15 laundry cycles, or at least about 20 laundry cycles, or at least about 25 laundry cycles, or at least about 30 laundry cycles, or at least about 40 laundry cycles, or at least about 50 laundry cycles. As an additional example, the moisture-management pouches and garments of FIGS. 1-18B may partially, substantially completely, or completely retain their moisture-management properties after undergoing at least 1 laundry cycle, or at least 3 laundry cycles, or at least 5 laundry cycles, or at least 7 laundry cycles, or at least 10 laundry cycles, or at least 15 laundry cycles, or at least 20 laundry cycles, or at least 25 laundry cycles, or at least 30 laundry cycles, or at least 40 laundry cycles, or at least 50 laundry cycles.

As used herein, "washing machine" and "dryer" may refer to any current or future machines that are designed to clean and/or dry clothing items. In addition, as used herein, a "laundry cycle" may refer to a washing of a garment only, or both a washing and drying of the garment.

Additionally, as used herein, boxers, boxer briefs, briefs, pants, shorts, compression tights, joggers, and the like may be collectively described as "lower torso garments."

Various properties of the garments of FIGS. 1-18B were described with reference to one or more values or one or more ranges of values. It is to be understood that each property described herein with reference to numerical values or ranges may be imparted with a discrete value, or a range of values, consistent with all values recited with reference to said property. In addition, each property described herein with reference to numerical values or ranges may be imparted with a discrete value, or a range of values, falling within any minimum and maximum value or range recited with reference to said property.

The present disclosure also relates to a method of manufacturing a moisture management garment. The method may include a step of providing one or more of a body, a pair of optional leg portions, and a pouch, where the pouch comprises a first panel and a second panel each including a first, wearer-facing fabric layer and a coextensive second fabric layer disposed beneath the first, wearer-facing fabric layer. The first, wearer-facing fabric layer may adsorb and/or absorb moisture, and the second fabric layer may repel moisture. The method may further include the step(s) of coupling at least a portion of the first, wearer-facing fabric layer, the coextensive second fabric layer, the first and second panels, the body, and the pair of leg portions (if the leg portions are provided) along perimeter edges of the first panel and the second panel. Alternatively, the method may include providing a pouch that comprises a first panel assembly, a second panel assembly, and/or one or more additional panels or panel assemblies. The first panel assembly may include a first fabric layer (e.g., a wearer-facing panel assembly) that may include a first wearer-facing sublayer and a first outward-facing sublayer. Likewise, the second panel assembly (e.g., an outward-facing panel assembly) may include a second wearer-facing sublayer and a second outward-facing sublayer. The first wearer-facing sublayer of the first panel assembly may absorb, adsorb, or transport moisture, and at least a portion of the second panel assembly may be imparted with moisture-resistant properties. In other instances, the method may include additional or alternative steps not specifically described herein. Moreover, in certain instances, one or more of the steps described above may be omitted from the method.

It will be appreciated by those skilled in the art that while the above disclosure has been described above in connection with particular instances and examples, the above disclosure is not necessarily so limited, and that numerous other instances, examples, uses, modifications and departures from the instances, examples and uses are intended to be encompassed by the claims attached hereto. The entire disclosure of each patent and publication cited herein is incorporated by reference, as if each such patent or publication were individually incorporated by reference herein. Various features and advantages of the above disclosure are set forth in the following claims.

We claim:

1. A lower torso garment comprising:

a body provided in the form of a front lower torso portion and a rear lower torso portion coupled together to define a waist opening;

a pouch disposed at least partially in the front lower torso portion and imparted with moisture-management properties, the pouch including:

a fly panel assembly arranged to be adjacent to a body of a wearer when the lower torso garment is worn in an intended configuration, a cover panel assembly positioned adjacent to the fly panel assembly, wherein the fly panel assembly and the cover panel assembly each include a technical face and a technical back, wherein the technical face of the fly panel assembly is imparted with a first texture to facilitate moisture transport, and wherein the technical back of the fly panel assembly is imparted with a second texture different from the first texture, and a fly opening at least partially defined by the fly panel assembly and the cover panel assembly.

2. The lower torso garment of claim 1, wherein a portion of the fly panel assembly is decoupled from the lower torso garment, and wherein a portion of the cover panel assembly is decoupled from the lower torso garment.

3. The lower torso garment of claim 1, wherein:

the pouch is coupled to the body via a first pouch seam, a second pouch seam, and a third pouch seam, the first pouch seam and the second pouch seam couple two or more fabric layers of the pouch together, the first pouch seam and the second pouch seam couple the fly panel assembly and the cover panel assembly to the front lower torso portion, and the third pouch seam couples the pouch to a gusset or the rear lower torso portion.

4. The lower torso garment of claim 1, wherein the fly panel assembly includes at least one fabric layer comprising a moisture-absorbent mesh and at least one fabric layer comprising a blend of hydrophobic and hydrophilic materials.

5. The lower torso garment of claim 1, wherein at least one of the fly panel assembly and the cover panel assembly is treated with one or more agents selected from a group consisting of a wicking agent, a soil release agent, an odor control agent, a water-repelling agent, a water-resistant agent, an antibacterial agent, an antimicrobial agent, a hygiene agent, and combinations thereof.

6. The lower torso garment of claim 1, wherein:

a first seam couples the fly panel assembly to the front lower torso portion, a second seam positioned opposite of the first seam couples a first fabric layer and a second fabric layer of the fly panel assembly, a third seam positioned opposite of the first seam couples the cover panel assembly to the front lower torso portion, the second seam is proximate to the fly opening.

7. The lower torso garment of claim 6, wherein the second seam is provided in the form of a fold-over seam, and the fold-over seam is coupled to the third seam.

8. The lower torso garment of claim 1, wherein the technical face of the fly panel assembly includes one or more pores designed to facilitate a transport of moisture.

9. The lower torso garment of claim 1, wherein the lower torso garment further includes a rear panel positioned on the rear lower torso portion, and the rear panel is imparted with moisture management properties.

10. The lower torso garment of claim 1, wherein:

the body comprises a first fabric, the fly panel assembly and the cover panel assembly each comprise a second fabric, wherein the first fabric and the second fabric are imparted with a same fabric blend; and the fly panel assembly and the cover panel assembly further comprise a third fabric.

11. The lower torso garment of claim 1, wherein a seam couples a first fabric layer and a second fabric layer of the fly panel assembly, and wherein the seam is provided in the form of one or more of a fold-over seam, a chainstitched seam, a flatlock seam, a lockstitch seam, or an overlock stitched seam.

12. The lower torso garment of claim 1, wherein a first fabric layer of the fly panel assembly is configured to transport moisture away from the body of the wearer.

13. A lower torso garment comprising:

a body provided in the form of a front lower torso portion and a rear lower torso portion coupled together to define a waist opening;

a pouch disposed at least partially in the front lower torso portion and imparted with moisture-management properties, the pouch including:

a fly panel assembly arranged to be adjacent to a body of a wearer when the lower torso garment is worn in an intended configuration, wherein the fly panel assembly includes a first fabric layer configured to transport moisture away from the body of the wearer, a second fabric layer positioned proximate to an exterior of the lower torso garment, and a third fabric layer positioned between the first and second fabric layers, the third fabric layer provided in substantially the same form as the first fabric layer, a cover panel assembly positioned adjacent to the fly panel assembly, and a fly opening at least partially defined by the fly panel assembly and the cover panel assembly.

14. The lower torso garment of claim 13, wherein one or more of the first fabric layer, the second fabric layer, or the third fabric layer of the fly panel assembly is laminated with a hydrophobic film.

15. The lower torso garment of claim 13, wherein the fly panel assembly includes a technical face that is imparted with one or more pores designed to facilitate transport of moisture.

16. The lower torso garment of claim 15, wherein the fly panel assembly includes a technical back, and wherein the technical back is imparted with a texture that is different than a texture of the technical face.

17. The lower torso garment of claim 13, wherein a first perimeter edge of the first fabric layer is coupled to a second perimeter edge of the second fabric layer by a seam.

18. The lower torso garment of claim 13, wherein the first fabric layer and the second fabric layer of the fly panel assembly are substantially coextensive.

19. A lower torso garment comprising:

a body provided in the form of a front lower torso portion and a rear lower torso portion coupled together to define a waist opening; and a pouch disposed at least partially in the front lower torso portion and imparted with moisture-management properties, the pouch including:

a fly panel assembly arranged to be adjacent to a body of a wearer when the lower torso garment is worn in an intended configuration;

a cover panel assembly positioned adjacent to the fly panel assembly;

a fly opening at least partially defined by the fly panel assembly and the cover panel assembly;

a first seam coupling the fly panel assembly to the front lower torso portion;

a second seam positioned opposite of the first seam, wherein the second seam couples a first fabric layer and a second fabric layer of the fly panel assembly and is positioned and located proximate to the fly opening; and a third seam positioned opposite of the first seam that couples the cover panel assembly to the front lower torso portion.

20. The lower torso garment of claim 19, wherein one or more of the first fabric layer and the second fabric layer of the fly panel assembly includes a textured technical face designed to draw moisture away from the wearer.

* * * * *